US011655835B2

(12) United States Patent
Lepper

(10) Patent No.: US 11,655,835 B2
(45) Date of Patent: May 23, 2023

(54) SERVICEABLE STUD-TO-TIE STRAP FASTENER

(71) Applicant: ILLINOIS TOOL WORKS INC., Glenview, IL (US)

(72) Inventor: Mark O. Lepper, Oak Park, IL (US)

(73) Assignee: Illinois Tool Works Inc., Glenview, IL (US)

(*) Notice: Subject to any disclaimer, the term of this patent is extended or adjusted under 35 U.S.C. 154(b) by 0 days.

(21) Appl. No.: 16/749,232

(22) Filed: Jan. 22, 2020

(65) Prior Publication Data

US 2020/0240450 A1 Jul. 30, 2020

Related U.S. Application Data

(60) Provisional application No. 62/837,265, filed on Apr. 23, 2019, provisional application No. 62/798,112, filed on Jan. 29, 2019, provisional application No. 62/798,108, filed on Jan. 29, 2019.

(51) Int. Cl.

| *F16B 2/10* | (2006.01) |
| *F16B 2/06* | (2006.01) |
| *F16L 3/10* | (2006.01) |
| *F16B 37/08* | (2006.01) |
| *A61B 17/70* | (2006.01) |
| *F16L 3/22* | (2006.01) |

(52) U.S. Cl.
CPC ............... *F16B 2/10* (2013.01); *F16B 2/065* (2013.01); *A61B 17/70* (2013.01); *F16B 37/0857* (2013.01); *F16B 37/0885* (2013.01); *F16L 3/10* (2013.01); *F16L 3/22* (2013.01)

(58) Field of Classification Search
CPC ........ F16B 2/10; F16B 2/065; F16B 37/0885; F16B 37/0857; F16B 7/00; F16L 3/10; F16L 3/22; E05D 7/10; E05D 5/10; A61B 17/70

See application file for complete search history.

(56) References Cited

U.S. PATENT DOCUMENTS

| 4,037,810 A * | 7/1977 | Pate ......................... F16L 3/222 |
| | | 248/68.1 |
| 4,172,578 A * | 10/1979 | Pate ...................... F16L 3/1075 |
| | | 248/74.3 |
| 5,653,411 A * | 8/1997 | Picco .................... F16L 3/2235 |
| | | 248/74.1 |
| 5,937,488 A * | 8/1999 | Geiger .................. F16L 3/1033 |
| | | 24/339 |
| 5,973,488 A * | 10/1999 | Fackler ..................... G05F 1/10 |
| | | 323/273 |
| 6,053,458 A | 4/2000 | Meyer |

(Continued)

FOREIGN PATENT DOCUMENTS

| CN | 108131495 A | 6/2018 | |
| EP | 1160402 A1 * | 12/2001 | ............ E05B 79/12 |

(Continued)

OTHER PUBLICATIONS

Extended European Search Report for European Patent Application No. 20153617.4, dated Jun. 3, 2020 (8 pages).

*Primary Examiner* — Tan Le
(74) *Attorney, Agent, or Firm* — Quarles & Brady LLP

(57) ABSTRACT

An example fastener includes a body and a clamp. The body includes a first resilient arm. The clamp is pivotably engaged with the body.

19 Claims, 62 Drawing Sheets

(56) References Cited

U.S. PATENT DOCUMENTS

| | | | |
|---|---|---|---|
| 6,565,049 B2* | 5/2003 | Hahn | B60R 16/0215 248/68.1 |
| 7,870,646 B2 | 1/2011 | Levey et al. | |
| 8,967,556 B2* | 3/2015 | Meyers | B60R 16/0215 248/74.1 |
| 9,297,479 B2* | 3/2016 | Kato | F16L 25/01 |
| 9,416,896 B1* | 8/2016 | Kato | F16L 3/222 |
| 2004/0005188 A1 | 1/2004 | Anscher | |
| 2004/0055158 A1* | 3/2004 | Izumi | B26B 19/046 30/43.92 |
| 2004/0076465 A1 | 4/2004 | Geiger | |
| 2005/0284989 A1* | 12/2005 | Mizukoshi | F16L 55/035 248/65 |
| 2012/0153095 A1* | 6/2012 | Child | F16L 55/035 248/68.1 |

FOREIGN PATENT DOCUMENTS

| | | | | |
|---|---|---|---|---|
| EP | 1870538 A1 | 12/2007 | | |
| EP | 2708762 A2 | 3/2014 | | |
| FR | 2776724 A1 * | 10/1999 | | F16C 1/223 |
| FR | 2855861 A1 * | 12/2004 | | B29C 45/0017 |
| GB | 1438598 A | 6/1976 | | |
| GB | 2129863 A | 5/1984 | | |
| JP | S60134985 U | 9/1985 | | |

\* cited by examiner

SERVICEABLE STUD-TO-TIE STRAP FASTENER

RELATED APPLICATIONS

The present application claims priority to U.S. Provisional Application Ser. No. 62/798,108 filed on Jan. 29, 2019, U.S. Provisional Application Ser. No. 62/798,112 filed on Jan. 29, 2019, and U.S. Provisional Application Ser. No. 62/837,265 filed on Apr. 23, 2019, which are incorporated by reference in their entireties herein.

FIELD OF THE DISCLOSURE

Embodiments of the present disclosure generally relate to a fastening system and, more particularly, to a fastener that is configured to serviceably connect a stud to a tie strap.

BACKGROUND

In recent years, fasteners have been developed to connect threaded stud and tie straps to one another. For example, automobiles include various wires and fluid lines that are bundled using tie straps. The tie straps are secured to threaded studs via a fastener.

Certain known fasteners include internal barbs. When the fastener is pushed onto a threaded stud, the internal barbs retainingly catch on external threads of the threaded stud.

However, these known fasteners are difficult for operators to remove from the threaded stud when servicing the vehicle. To reposition the wires and/or fluid lines, the operator cuts the tie strap to unscrew the fastener or pries the fastener off the threaded stud. Prying the fastener often damages the fastener. Thus, in either instance, the tie strap and/or the fastener is replaced.

Therefore, a need exists for a fastener that may be quickly assembled onto a stud, is easily removable, and is reusable.

SUMMARY

In one aspect, an example fastener is disclosed that includes a body and a clamp. The body includes a first resilient arm. The clamp is pivotably engaged with the body.

In another aspect, an example fastener is disclosed that includes clamp and a body. The clamp includes a first resilient arm. The body is pivotably engaged with the clamp.

In another aspect, an example fastener is disclosed that includes a body and a clamp. The body includes a resilient arm, a first hinge post, and a first hinge socket. The clamp includes a second hinge post and a second hinge socket. The second hinge post is pivotably engaged with the first hinge socket. The second hinge socket pivotably engages with the first hinge post.

In a further aspect, an example fastener is disclosed that includes a body and a clamp. The body includes a resilient arm, a hinge tongue, and a rear wall. The hinge tongue and the rear wall define a hinge pocket. The clamp includes a hinge post pivotably disposed in the hinge pocket and engaged with the hinge tongue and the rear wall.

Figure 1:
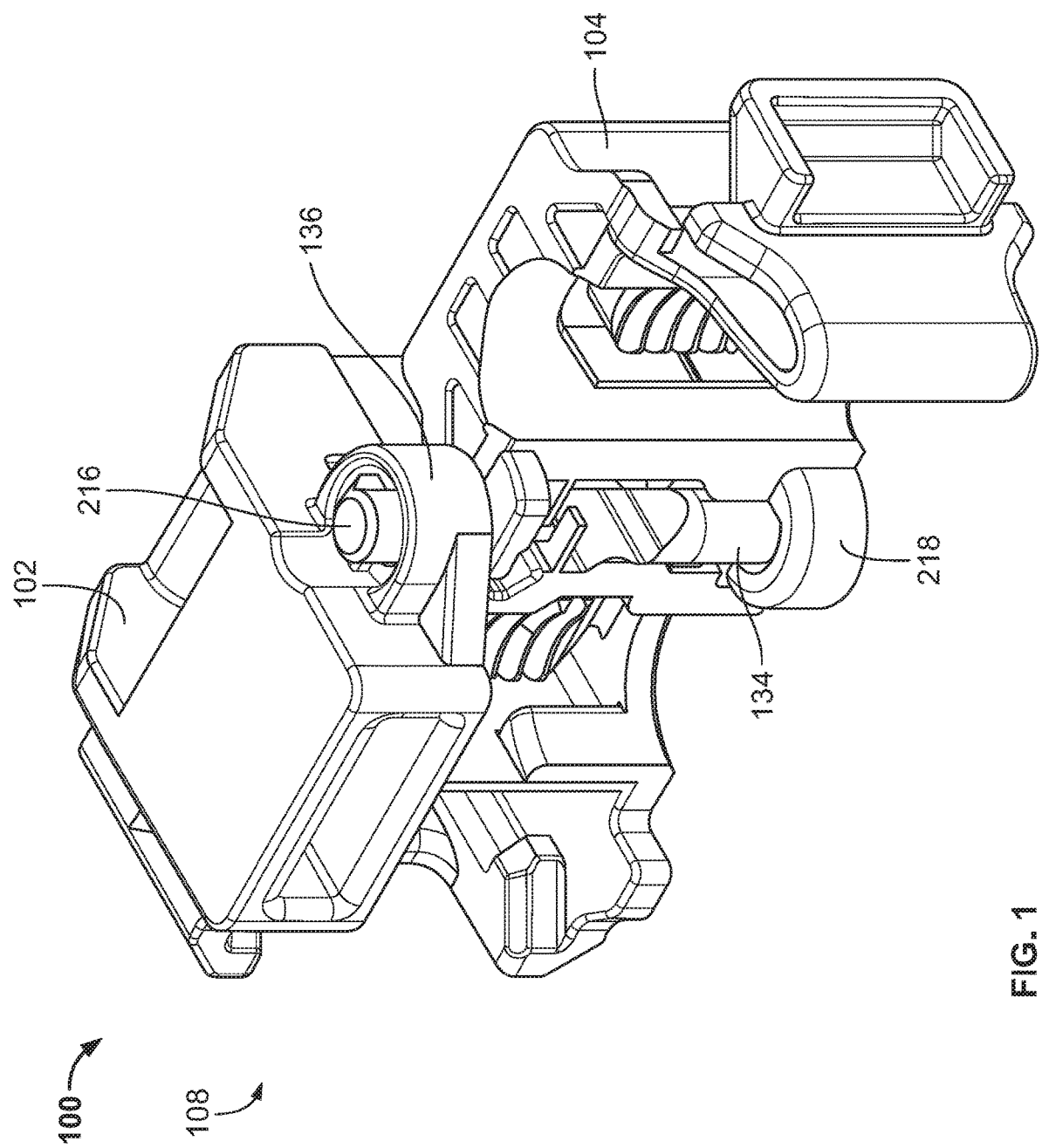
FIG. 1 is an isometric view of a first example fastener according to an embodiment of the present disclosure in an open state.

Before the embodiments of the disclosure are explained in detail, it is to be understood that the disclosure is not limited in its application to the details of construction and the arrangement of the components set forth in the following description or illustrated in the drawings. The disclosure is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION

Embodiments of the present disclosure provide a fastener that is reusable and has features that facilitate operators in quickly assembling the fastener onto a stud and easily removing the fastener from the stud.

Figure 13:
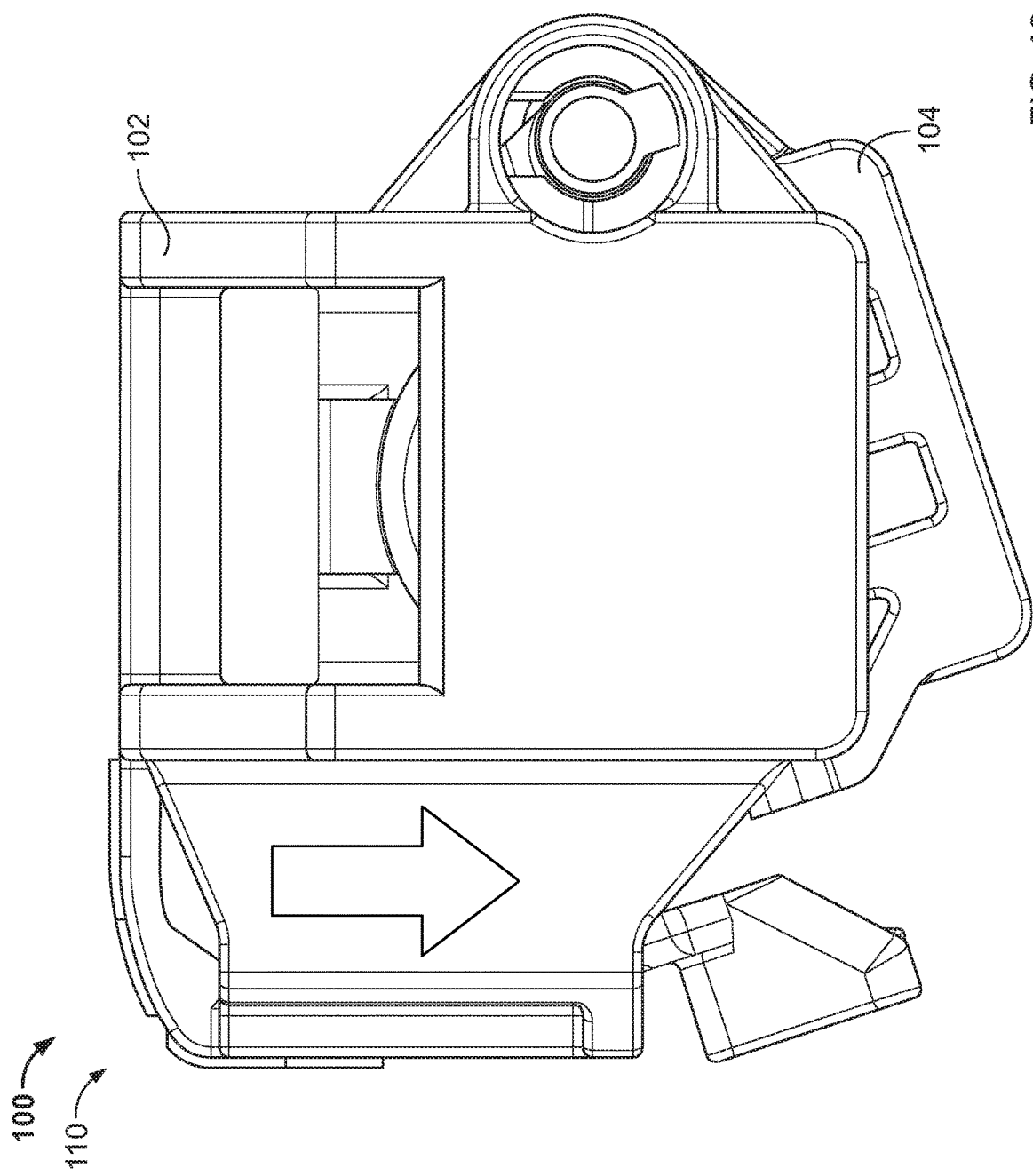
FIG. 13 is a top view of the first example fastener of FIGS. 1-7 in an intermediate state.
Figure 14:
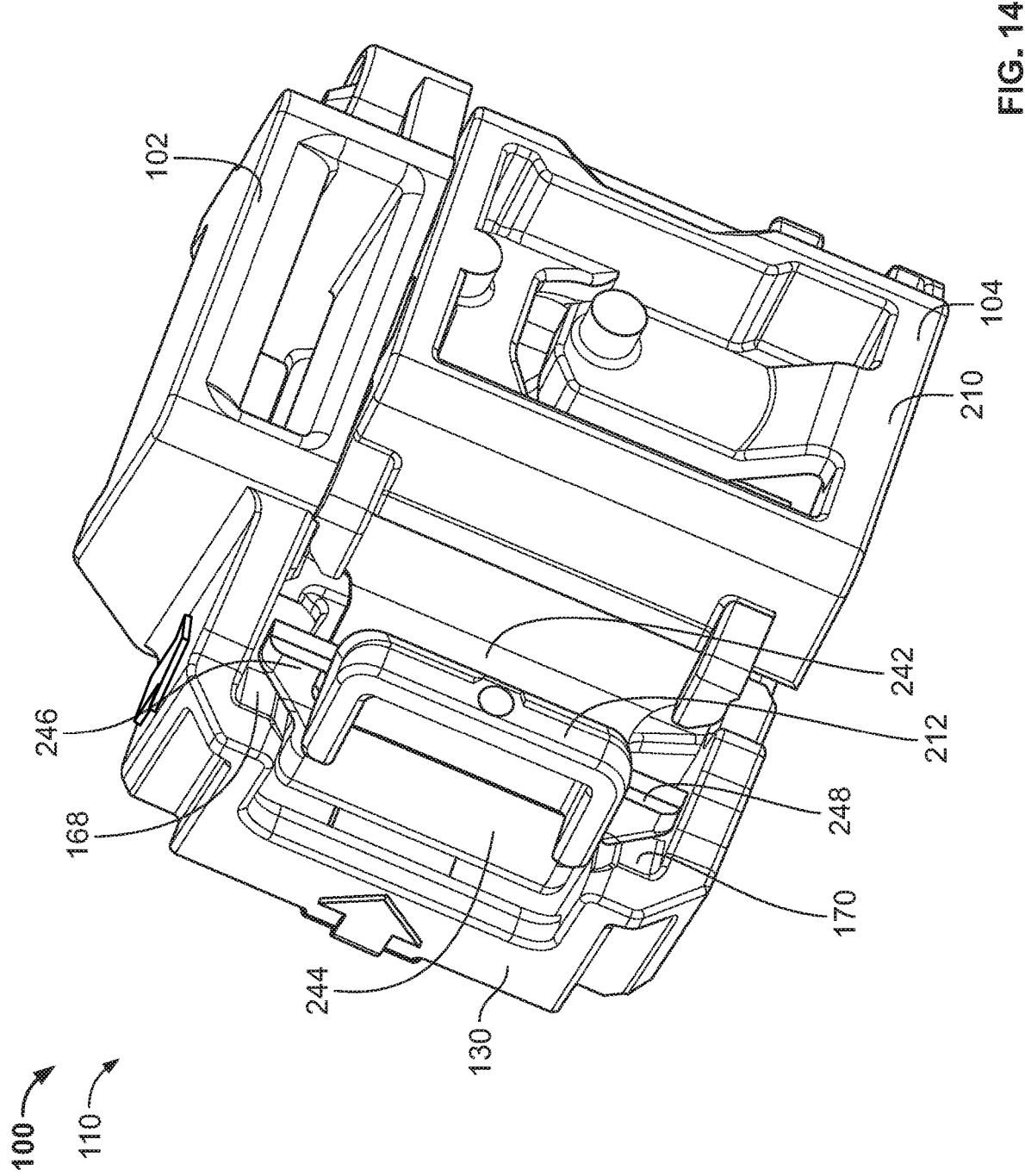
FIG. 14 is an isometric view of the first example fastener of FIGS. 1-7 and 13 in the intermediate state.
Figure 18:
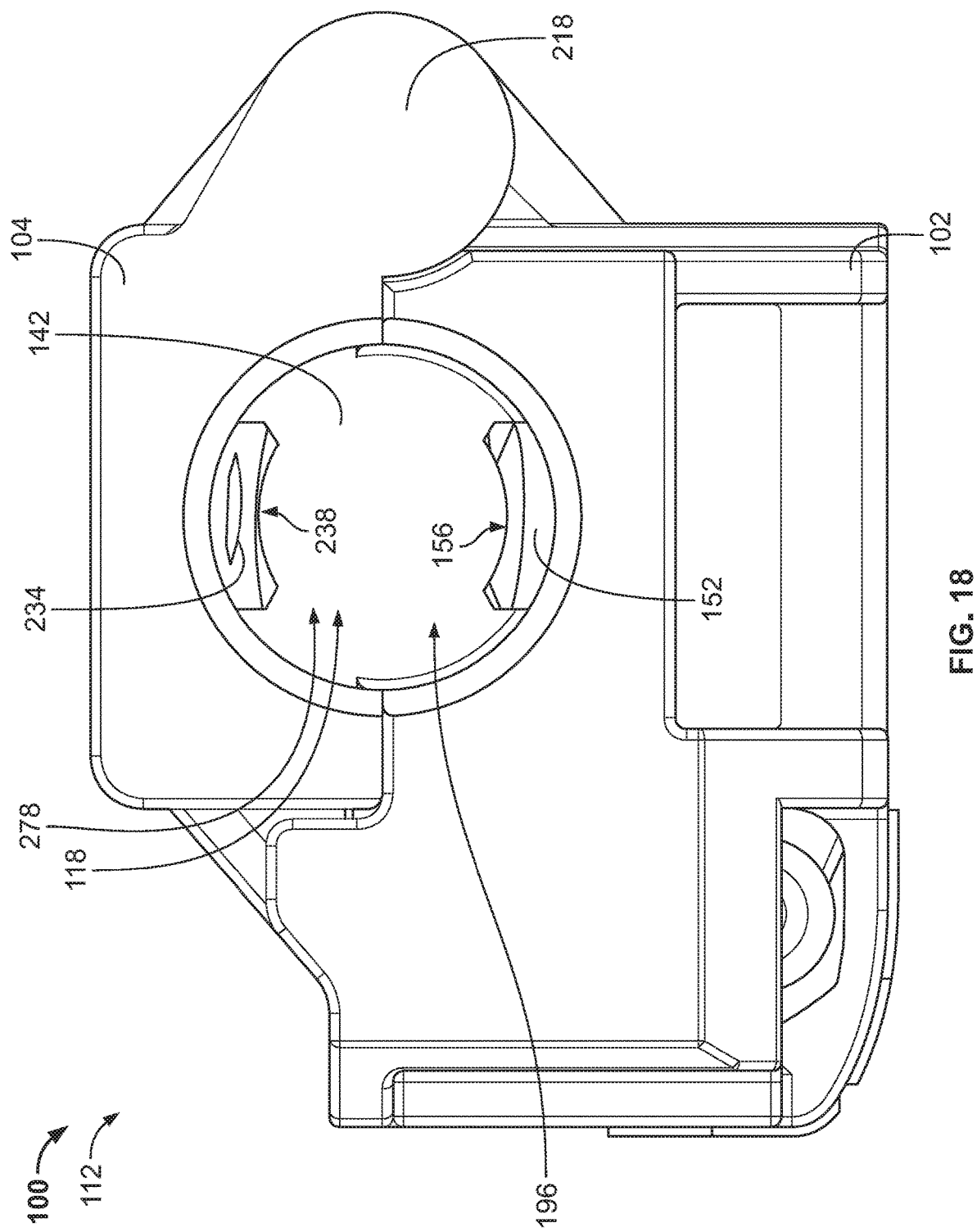
FIG. 18 is a bottom view of the first example fastener of FIGS. 1-7 and 13-17 in the closed state.
Figure 19:
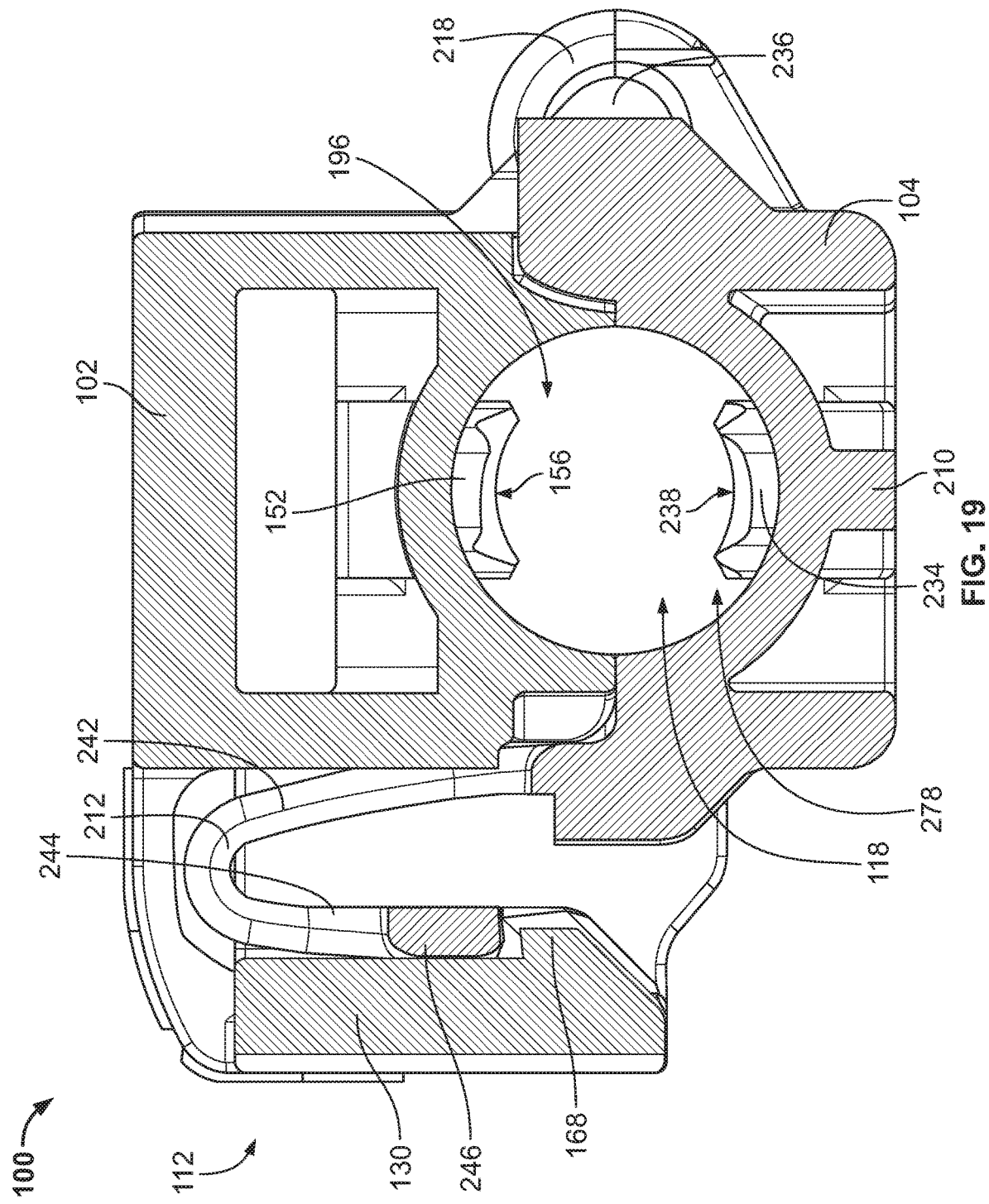
FIG. 19 is a cross-sectional view of the first example fastener of FIGS. 1-7 and 13-18 taken along line 19-19 of FIG. 16.
Figure 20:
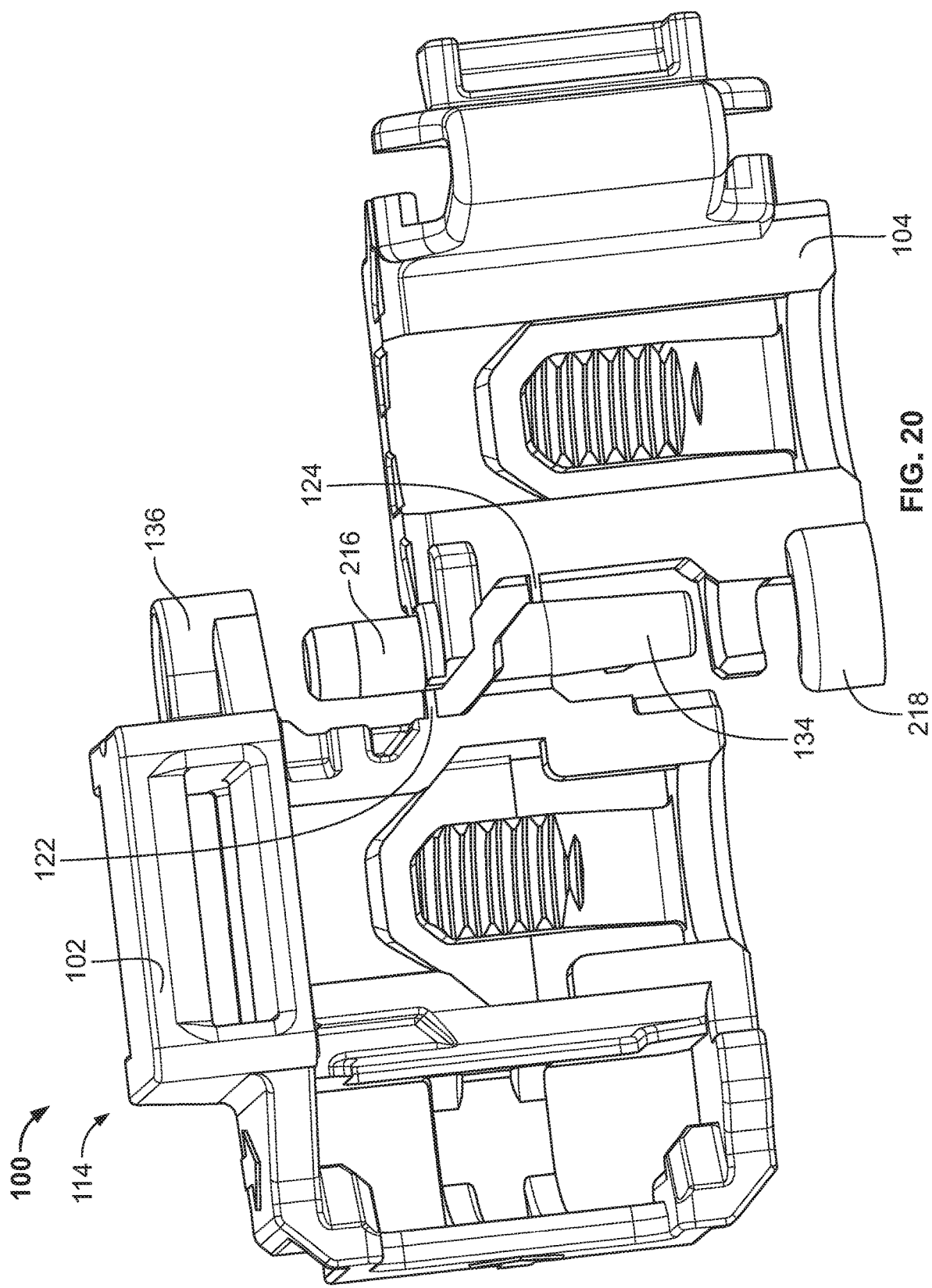
FIG. 20 is an isometric view of the first example fastener of FIGS. 1-7 and 13-19 in an as-molded state.

A first example fastener 100 according to an embodiment of the present disclosure is depicted in FIGS. 1-8 and 13-23. The first example fastener 100 includes a body 102 and a clamp 104. With reference to FIGS. 1-8, the first example fastener 100 is shown in an open state 108. With reference to FIGS. 13 and 14, the first example fastener 100 is shown in an intermediate state 110. With reference to FIGS. 15-19 and 21-23, the first example fastener 100 is shown in a closed state 112. With reference to FIG. 20, the first example fastener 100 is shown in an as-molded state 114.

With reference to FIGS. 13 and 14, the body 102 is pivotably connected to the clamp 104. Additionally, with reference to FIGS. 15-19 and 21-23, the clamp 104 selectively latchably secures in the body 102. With reference to FIGS. 15, 16, 18, 22, and 23, when the first example fastener 100 is in the closed state 112 with the clamp 104 latched in the body 102, the body 102 and the clamp 104 define a stud cavity 118.

With reference to FIG. 20, the first example fastener 100 may be made of a polymer plastic (e.g., polyamide (PA), polyoxymethylene (POM), Acrylonitrile butadiene styrene (ABS), etc.). In some embodiments, the first example fastener 100 is produced from a single mold. In such embodiments, the first example fastener 100 includes one or more of a first stabilizer 122 and a second stabilizer 124. The first stabilizer 122 and the second stabilizer 124 join the body 102 to the clamp 104. During assembly, the first stabilizer 122 and the second stabilizer 124 are broken to pivotably engage the body 102 with the clamp 104.

Figure 9:
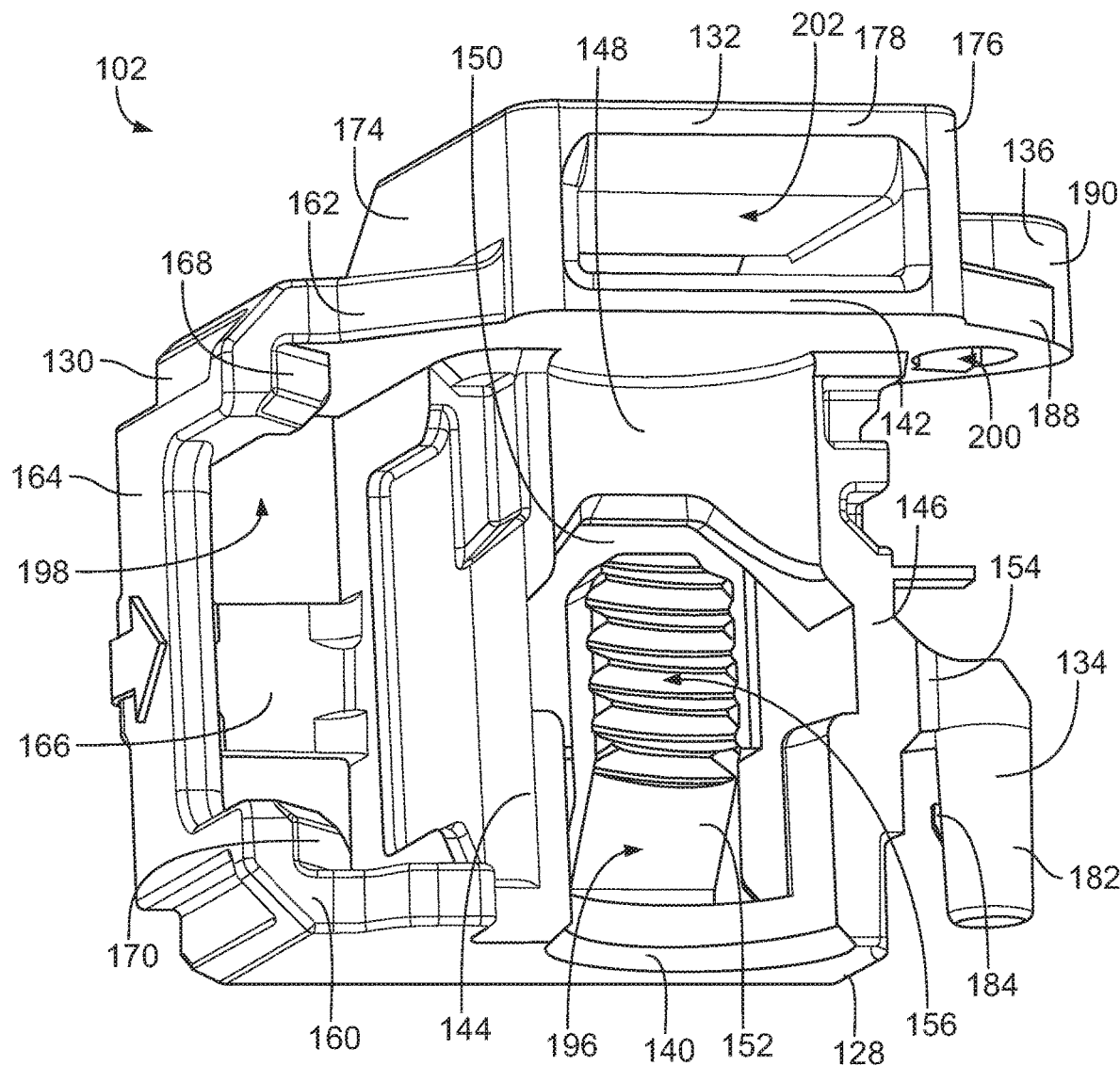
FIG. 9 is an isometric view of a body of the first example fastener of FIGS. 1-7.

With reference to FIG. 9, the body 102 includes a first stud receiver 128, a latch receiver 130, a loop 132, a first hinge post 134, and a first hinge socket 136. The latch receiver 130, the loop 132, the first hinge post 134, and the first hinge socket 136 are connected to the first stud receiver 128. The first stud receiver 128 is between the latch receiver 130 and the first hinge post 134. The first stud receiver 128 is between the latch receiver 130 and the first hinge socket 136.

With reference to FIG. 9, the first stud receiver 128 includes a first lower wall 140, a first upper wall 142, a first side wall 144, a second side wall 146, a first rear wall 148, a second rear wall 150, a first resilient arm 152, and a first hinge arm 154. The first resilient arm includes a first set of teeth 156. The first lower wall 140 is connected to the first side wall 144 and the second side wall 146. The first upper wall 142 is connected to the first side wall 144 and the second side wall 146. The first rear wall 148 is connected to the first side wall 144, the second side wall 146, and the first upper wall 142. The second rear wall 150 is connected to the first side wall 144 and the second side wall 146. The first resilient arm 152 is connected to and extends from the first lower wall 140 toward the first upper wall 142. The first set of teeth 156 extend inwardly. In other words, the first set of teeth extend away from the second rear wall 150. The first hinge arm 154 is connected to and extends from the second side wall 146.

With reference to FIG. 9, the latch receiver 130 includes a second lower wall 160, a second upper wall 162, a third side wall 164, a third rear wall 166, an upper shoulder 168, and a lower shoulder 170. The second lower wall 160 is connected to and extends from the first lower wall 140. The second upper wall 162 is connected to and extends from the first upper wall 142. The third side wall 164 is connected to and between the second lower wall 160 and the second upper wall 162. The upper shoulder 168 is connected to and extends from the second upper wall 162 and the third side wall 164. The lower shoulder 170 is connected to and extends from the third side wall 164 and the second lower wall 160. The third rear wall 166 is connected to and between the third side wall 164 and the first side wall 144.

With reference to FIG. 9, the loop 132 includes a fourth side wall 174, a fifth side wall 176, and a third upper wall 178. The third upper wall 178 is connected to and between the fourth side wall 174 and the fifth side wall 176. The fourth side wall 174 is connected to and extends from the first upper wall 142. The fifth side wall 176 is connected to and extends from the first upper wall 142.

With reference to FIG. 9, the first hinge post 134 includes a first pin 182 and a first snap lip 184. The first pin 182 is connected to the first hinge arm 154. The first snap lip 184 extends from the first pin 182. In some embodiments, the first snap lip 184 is trapezoidal in profile. In some embodiments, the first pin 182 is tapered to be partially conical.

Figure 3:
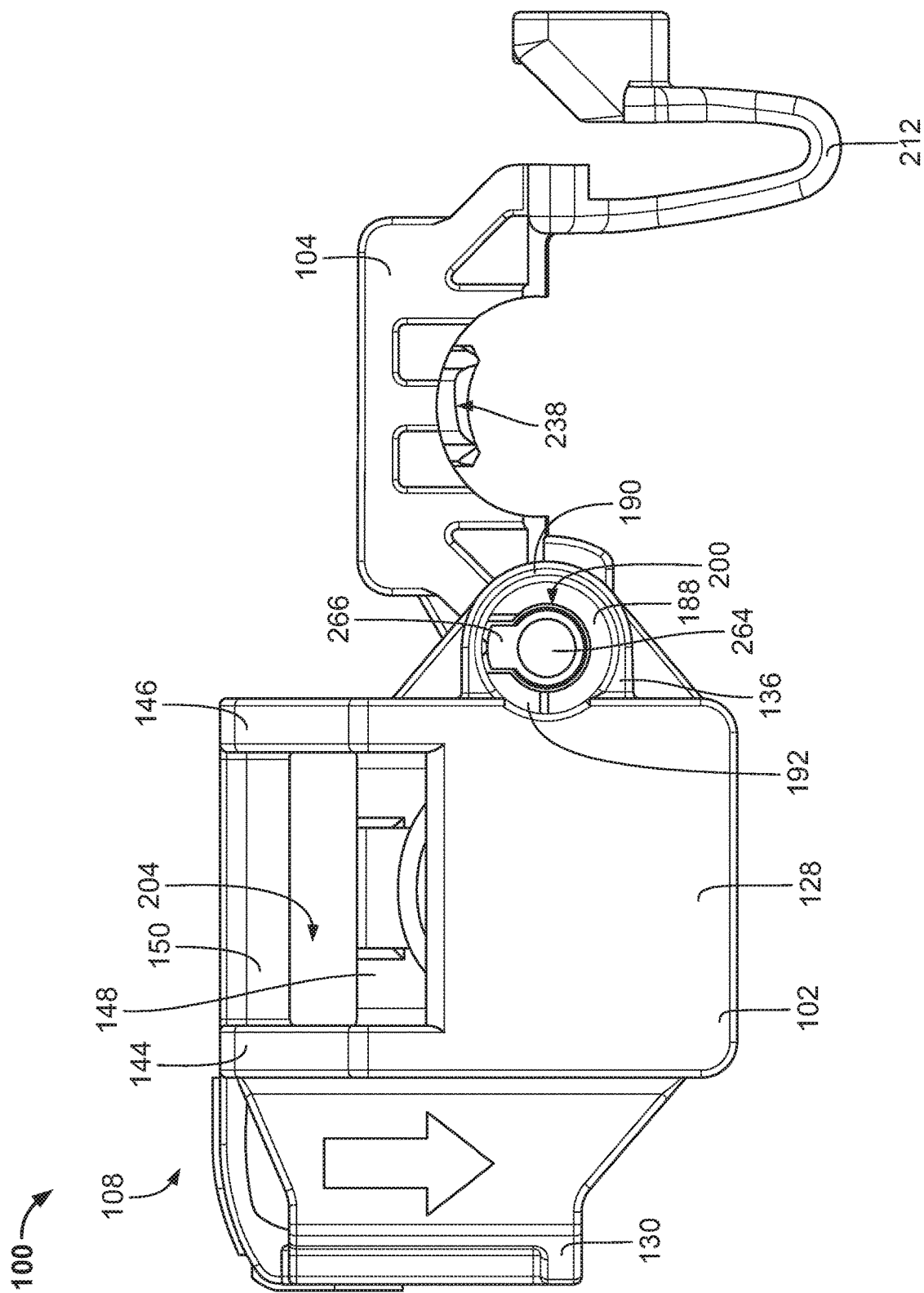
FIG. 3 is a top view of the first example fastener of FIGS. 1 and 2 in the open state.
Figure 4:
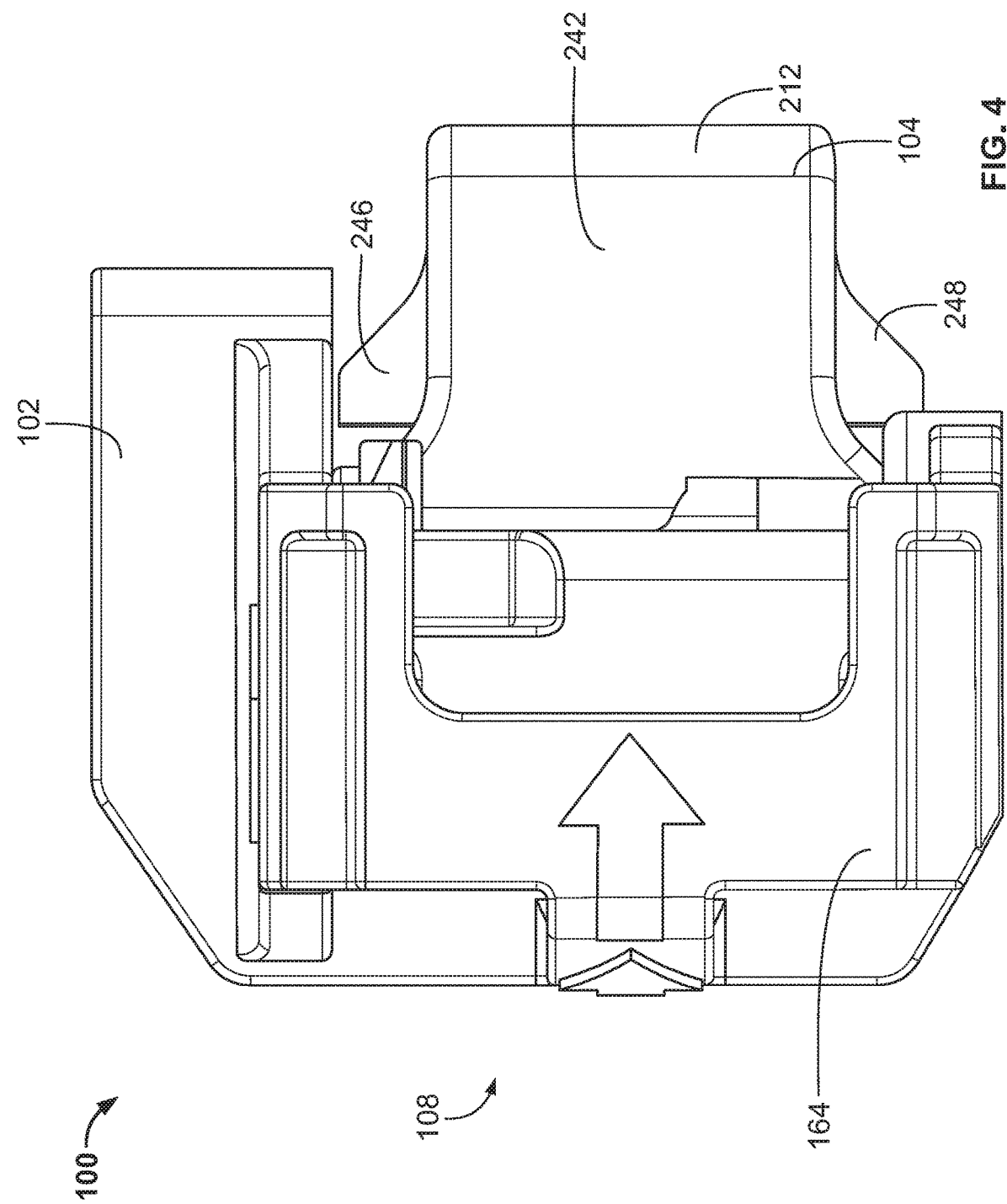
FIG. 4 is a side view of the first example fastener of FIGS. 1-3 in the open state.

With reference to FIG. 9, the first hinge socket 136 includes a fourth upper wall 188 and an extender wall 190. With reference FIG. 3, the first hinge socket 136 also includes a stop shoulder 192. Returning to FIG. 9, the fourth upper wall 188 is connected to and extends from first upper wall 142. The extender wall 190 is connected to and extends from the fourth upper wall 188 and the fifth side wall 176. With reference to FIG. 3, the stop shoulder 192 is connected to and extends from the fourth upper wall 188 and the extender wall 190. The stop shoulder 192 is disposed in the extender wall.

With reference to FIG. 9, the first stud receiver 128 defines a first stud pocket 196. More specifically, the first lower wall 140, the first upper wall 142, the first side wall 144, the second side wall 146, the first rear wall 148, and the first resilient arm 152 define the first stud pocket 196.

Figure 10:
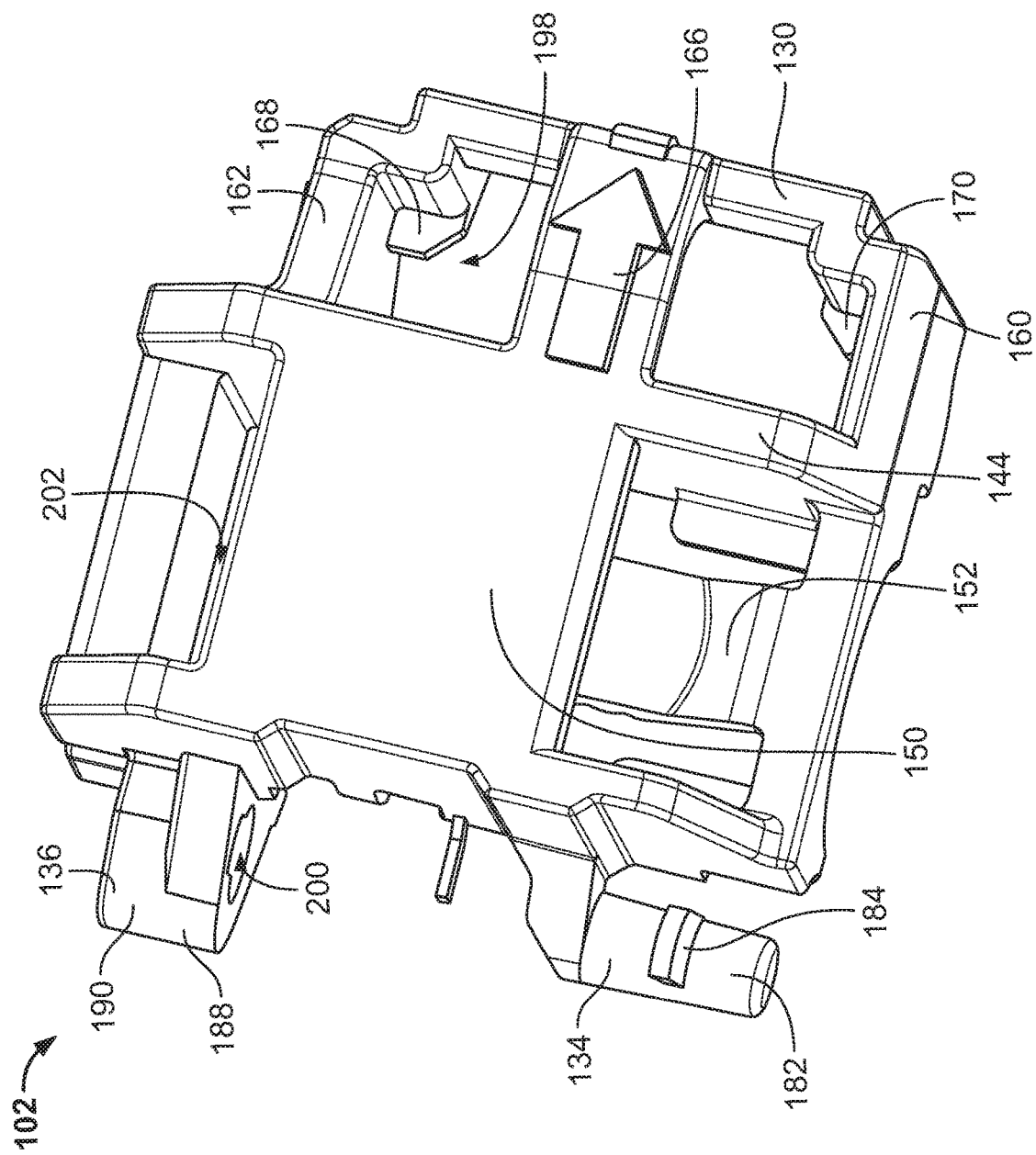
FIG. 10 is another isometric view of the body of FIG. 9.

With reference to FIGS. 9 and 10, the latch receiver 130 defines a latch pocket 198. More specifically, the second lower wall 160, the second upper wall 162, the third side wall 164, the third rear wall 166, the upper shoulder 168, and the lower shoulder 170 define the latch pocket 198.

With reference to FIG. 9, the first hinge socket 136 defines a first hinge opening 200. More specifically, the fourth upper wall 188 defines the first hinge opening 200. In some embodiments, the first hinge opening 200 is keyhole-shaped, as shown in FIG. 3.

With reference to FIG. 9, the loop 132 defines a first strap passage 202. More specifically, the fourth side wall 174, the fifth side wall 176, and the third upper wall 178 define the first strap passage 202. The first upper wall 142 further defines the first strap passage 202.

With reference to FIG. 3, the first stud receiver 128 also defines a second strap passage 204. More specifically, the first side wall 144, the second side wall 146, the first rear wall 148, and the second rear wall 150 define the second strap passage 204.

Figure 12:
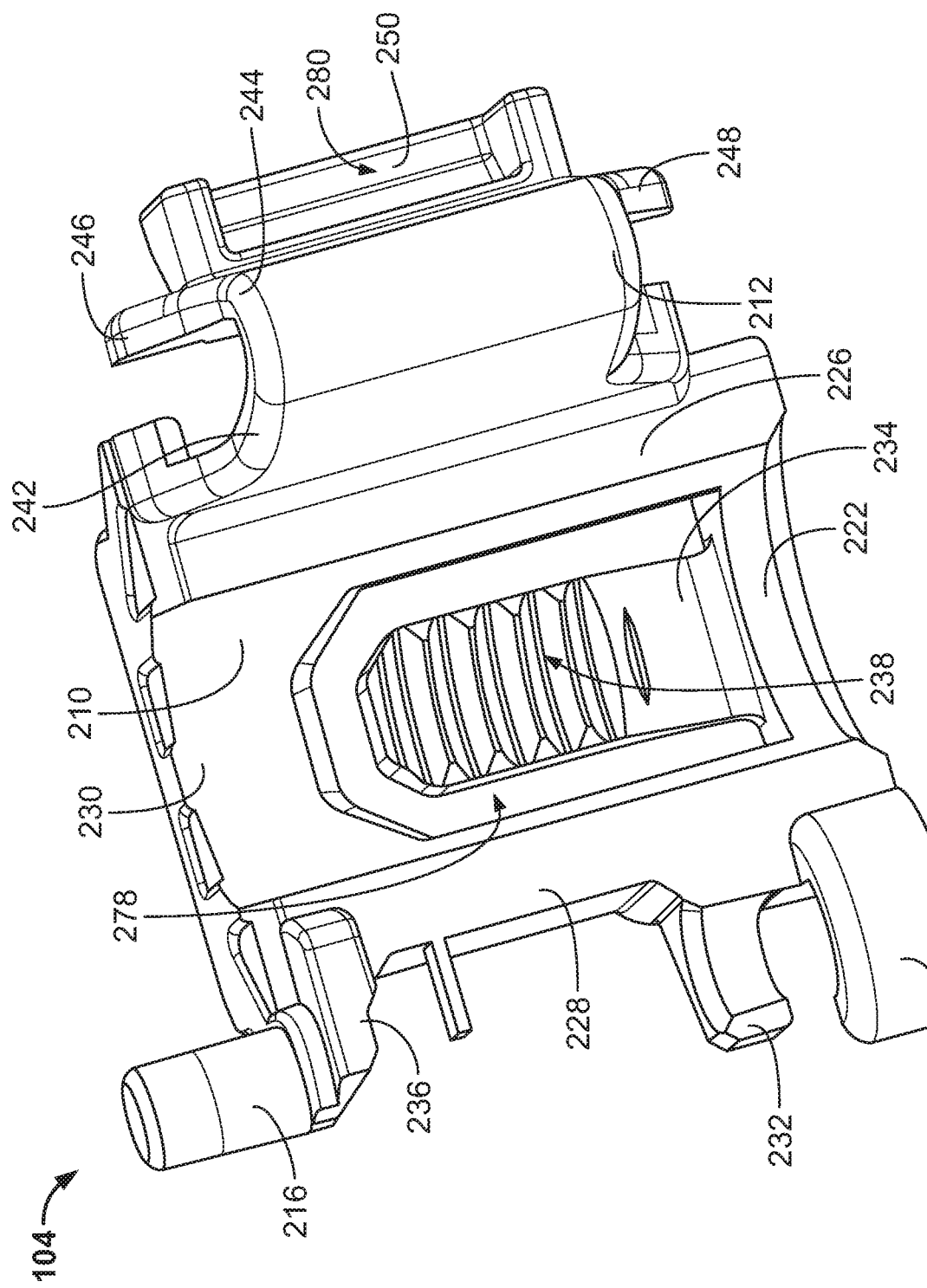
FIG. 12 is another isometric view of the clamp of FIG. 11.

With reference to FIG. 12, the clamp 104 includes a second stud receiver 210, a latch clip 212, a second hinge post 216, and a second hinge socket 218. The latch clip 212, the second hinge post 216, and the second hinge socket 218 are connected to and extend from the second stud receiver 210. The second stud receiver 210 is between the latch clip 212 and the second hinge post 216. The second stud receiver 210 is between the latch clip 212 and the second hinge socket 218.

With reference to FIG. 12, the second stud receiver 210 includes a third lower wall 222, a sixth side wall 226, a seventh side wall 228, a fourth rear wall 230, a pin hook 232, a second resilient arm 234, and a second hinge arm 236. The second resilient arm 234 includes a second set of teeth 238. The third lower wall 222 is connected to and between the sixth side wall 226 and the seventh side wall 228. The fourth rear wall 230 is connected to and between the sixth side wall 226 and the seventh side wall 228. In some embodiments, the fourth rear wall 230 is curved. The pin hook 232 is connected to and extends outwardly from the seventh side wall 228. The second resilient arm 234 is connected to and extends from the third lower wall 222.

Figure 5:
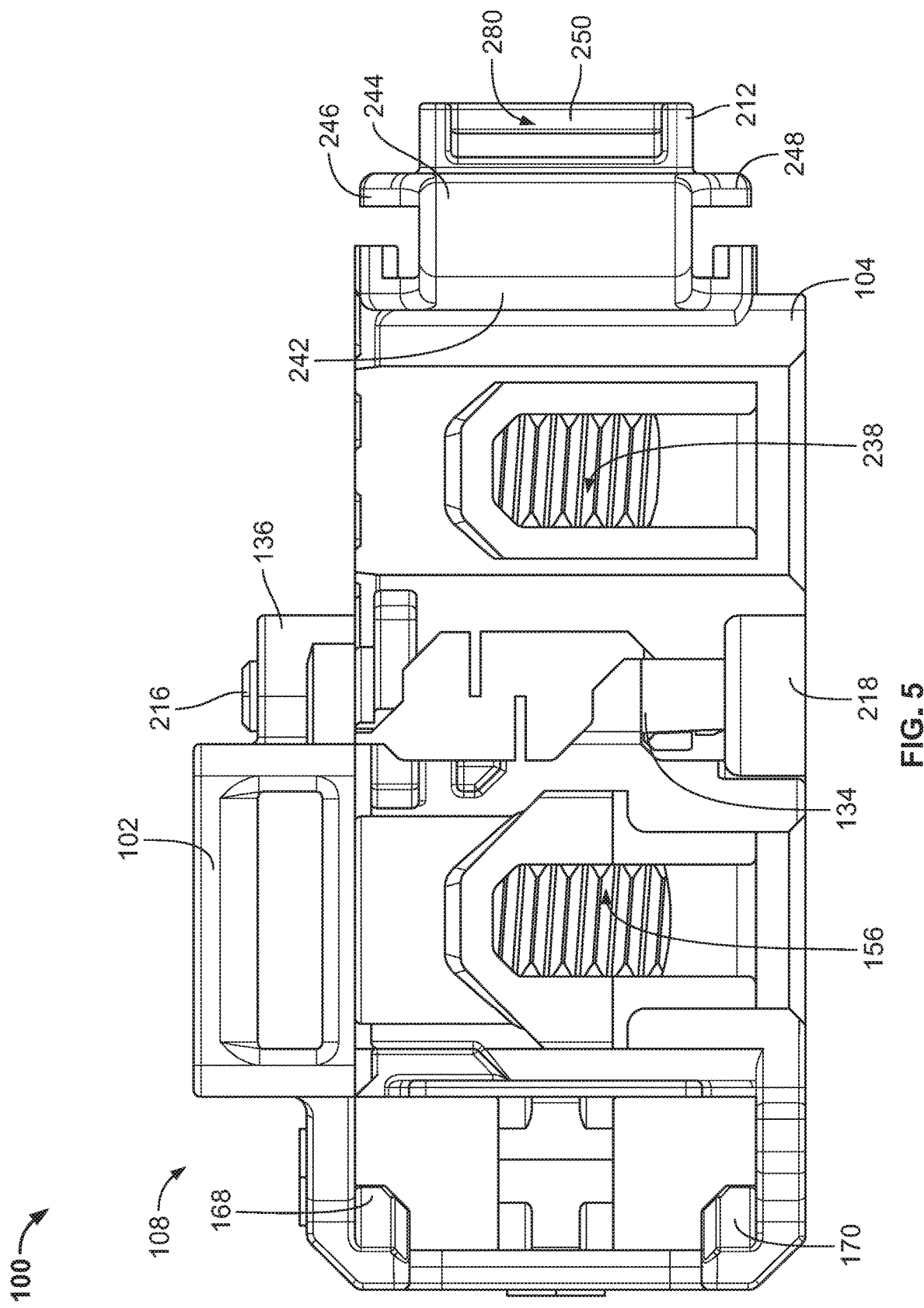
FIG. 5 is a front view of the first example fastener of FIGS. 1-4 in the open state.
Figure 6:
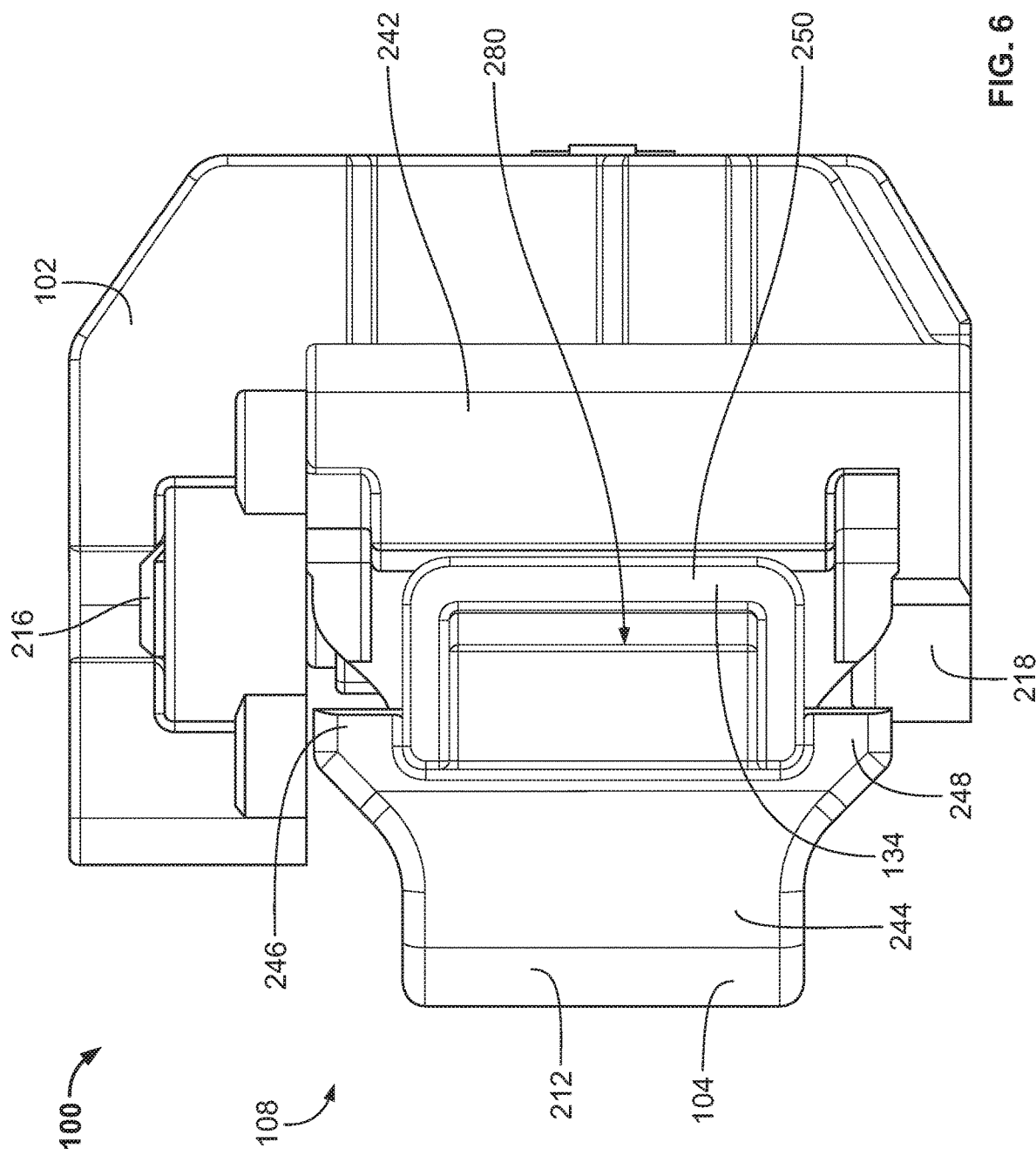
FIG. 6 is a another side view of the first example fastener of FIGS. 1-5 in the open state.

With reference to FIG. 12, the latch clip 212 includes a first resilient wall 242, a second resilient wall 244, an upper catch 246, a lower catch 248, and a release wall 250. The first resilient wall 242 is connected to the sixth side wall 226. The second resilient wall 244 is connected to the first resilient wall 242, the upper catch 246, the lower catch 248, and the release wall 250. The first resilient wall 242 and the second resilient wall 244 are transitionally connected to one another to form a rounded V shape, as shown in FIG. 3. With reference to FIG. 5, the upper catch 246 is opposite the lower catch 248. The release wall 250 is between the upper catch 246 and the lower catch 248. The release wall 250 is U-shaped. The upper catch 246 and the lower catch 248 are generally triangular. In other words, the upper catch 246 and the lower catch 248 are sloped relative to the second resilient wall 244 on one side.

Figure 11:
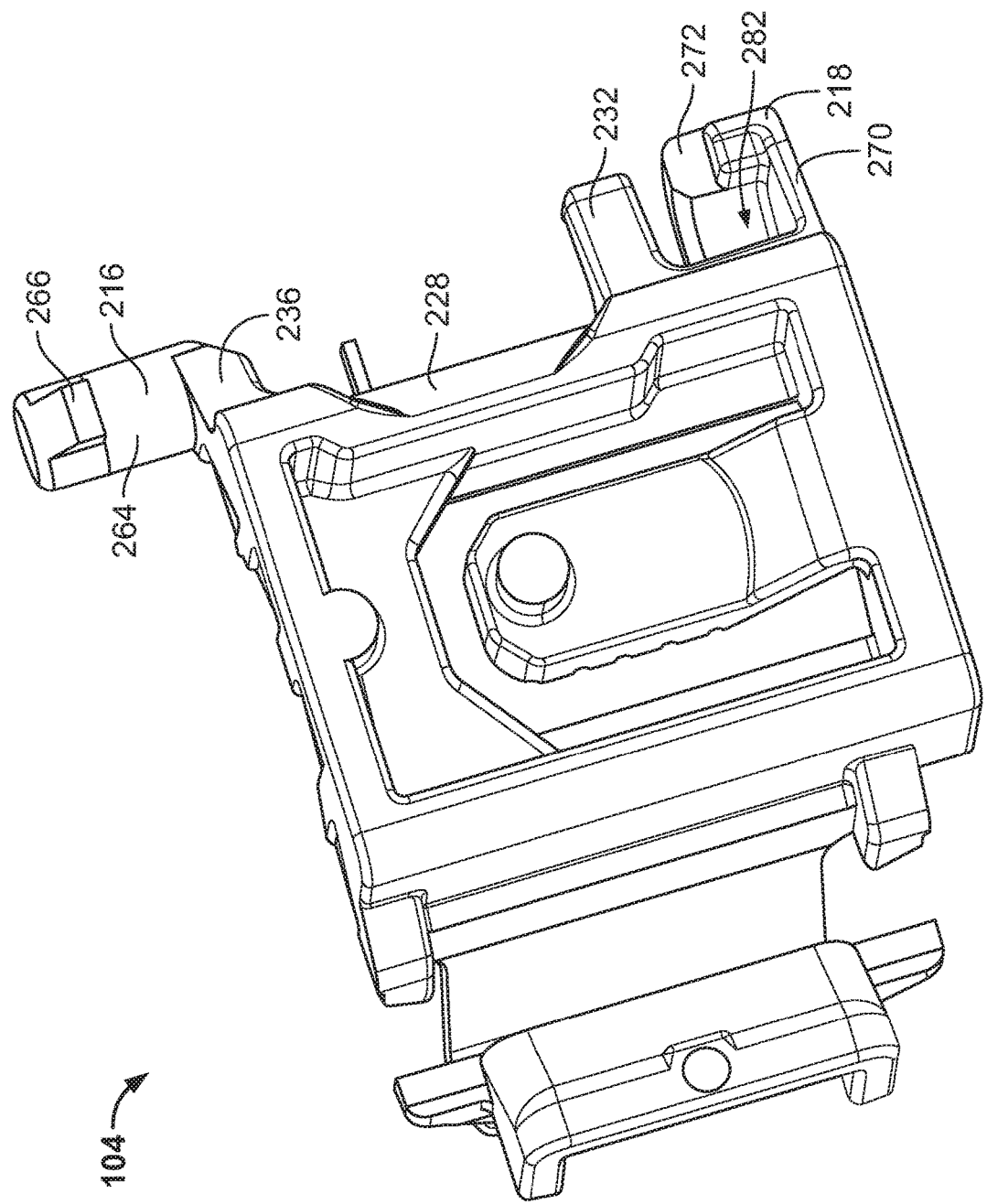
FIG. 11 is an isometric view of a clamp of the first example fastener of FIGS. 1-7.

With reference to FIG. 11, the second hinge post 216 includes a second pin 264 and a key 266. The second pin 264 is connected to the second hinge arm 236. The second pin 264 is generally cylindrical. The key 266 extends radially from the second pin 264. The key 266 is generally triangular. In other words, the key 266 is sloped relative to the second pin 264 on one side.

With reference to FIG. 11, the second hinge socket 218 includes a fourth lower wall 270 and a second extender wall 272. The second extender wall 272 is connected to the fourth lower wall 270 and extends toward the pin hook 232. The fourth lower wall 270 and the second extender wall 272 are connected to the seventh side wall 228. The second extender wall 272 is semi-cylindrical.

With reference to FIG. 12, the second stud receiver 210 defines a second stud pocket 278. More specifically, the third lower wall 222, the sixth side wall 226, the seventh side wall 228, the fourth rear wall 230, and the second resilient arm 234 define the second stud pocket 278. With reference to FIG. 18, when the clamp 104 is latched into the body 102 to place the first example fastener 100 in the closed state 112, the first stud pocket 196 and second stud pocket 278 are joined to form the stud cavity 118. Additionally, when the first example fastener 100 is in the closed state 112, the first set of teeth 156 is opposite the second set of teeth 238. In other words, when the first example fastener 100 is in the closed state 112, the first set of teeth 156 and the second set of teeth 238 face one another.

With reference to FIG. 12, the latch clip 212 defines a tool pocket 280. More specifically, the second resilient wall 244 and the release wall 250 define the tool pocket 280.

With reference to FIG. 11, the second hinge socket 218 defines a hinge well 282. More specifically, the fourth lower wall 270 and the second extender wall 272 define the hinge well 282.

Figure 2:
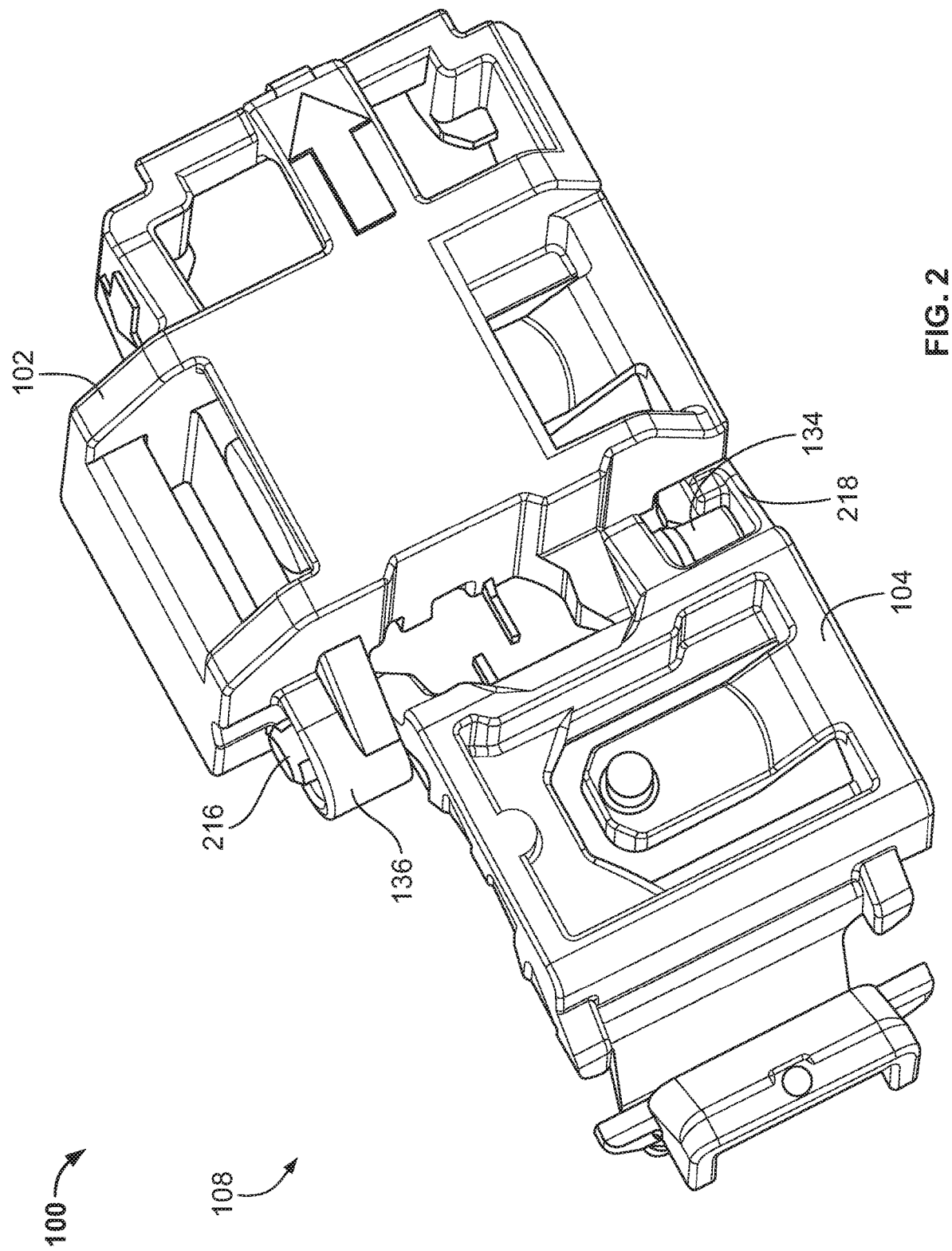
FIG. 2 is a second isometric view of the first example fastener of FIG. 1 in the open state.

With reference to FIG. 20, in operation, when the first example fastener 100 is produced the as-molded state 114, the clamp 104 and the body 102 are pushed toward one another to break the first stabilizer 122 and the second stabilizer 124. Further, the body 102 and the clamp 104 are pushed together to insert the first hinge post 134 into the second hinge socket 218, as shown in FIG. 2. Thus, the first hinge post 134 is pivotably disposed in the second hinge socket 218. Additionally, the body 102 and the clamp 104 are pushed together to insert the second hinge post 216 into the first hinge socket 136, as shown in FIG. 2. Thus, the second hinge post 216 is pivotably disposed in the first hinge socket 136.

Figure 7:
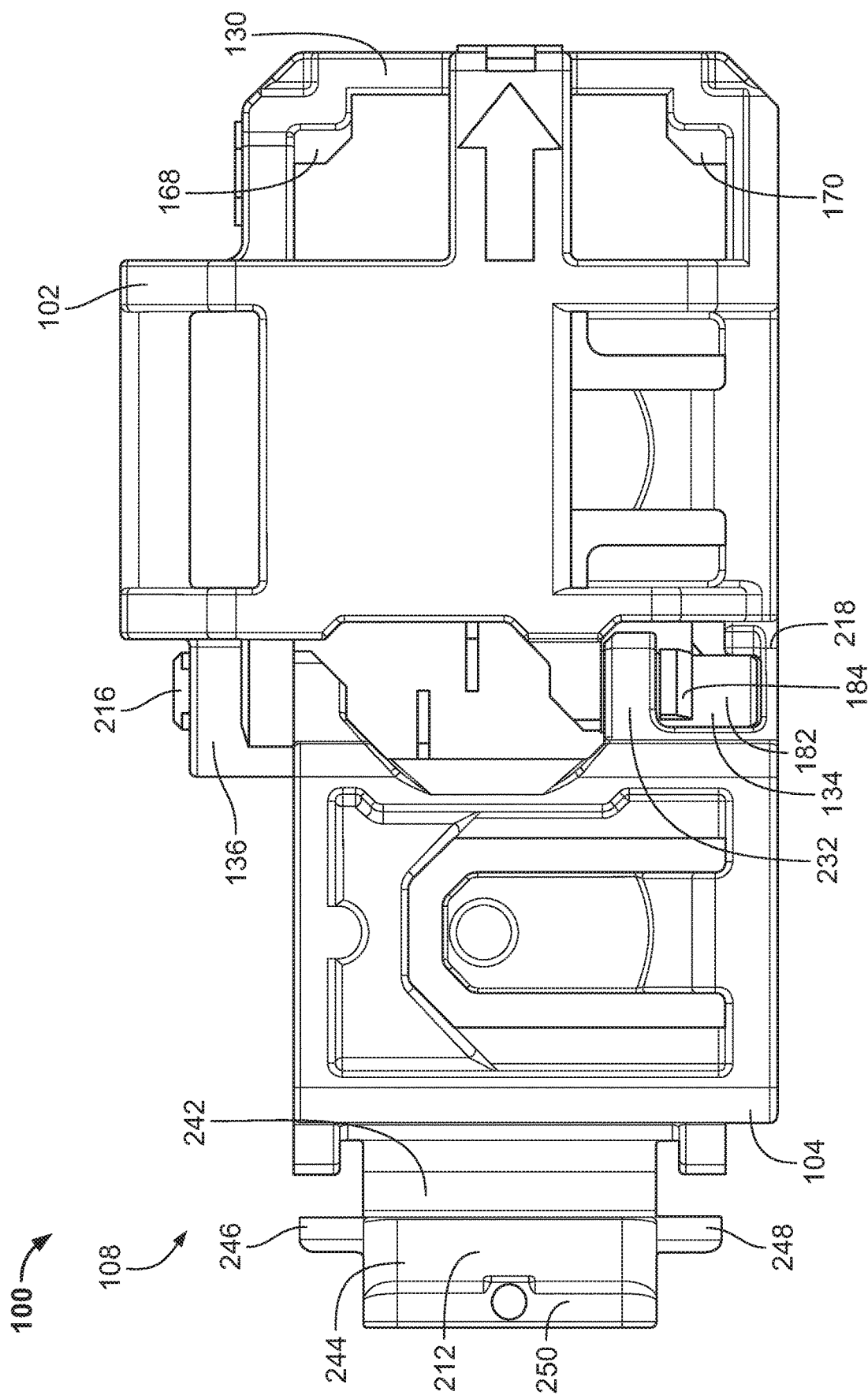
FIG. 7 is a rear view of the first example fastener of FIGS. 1-6 in the open state.
Figure 8:
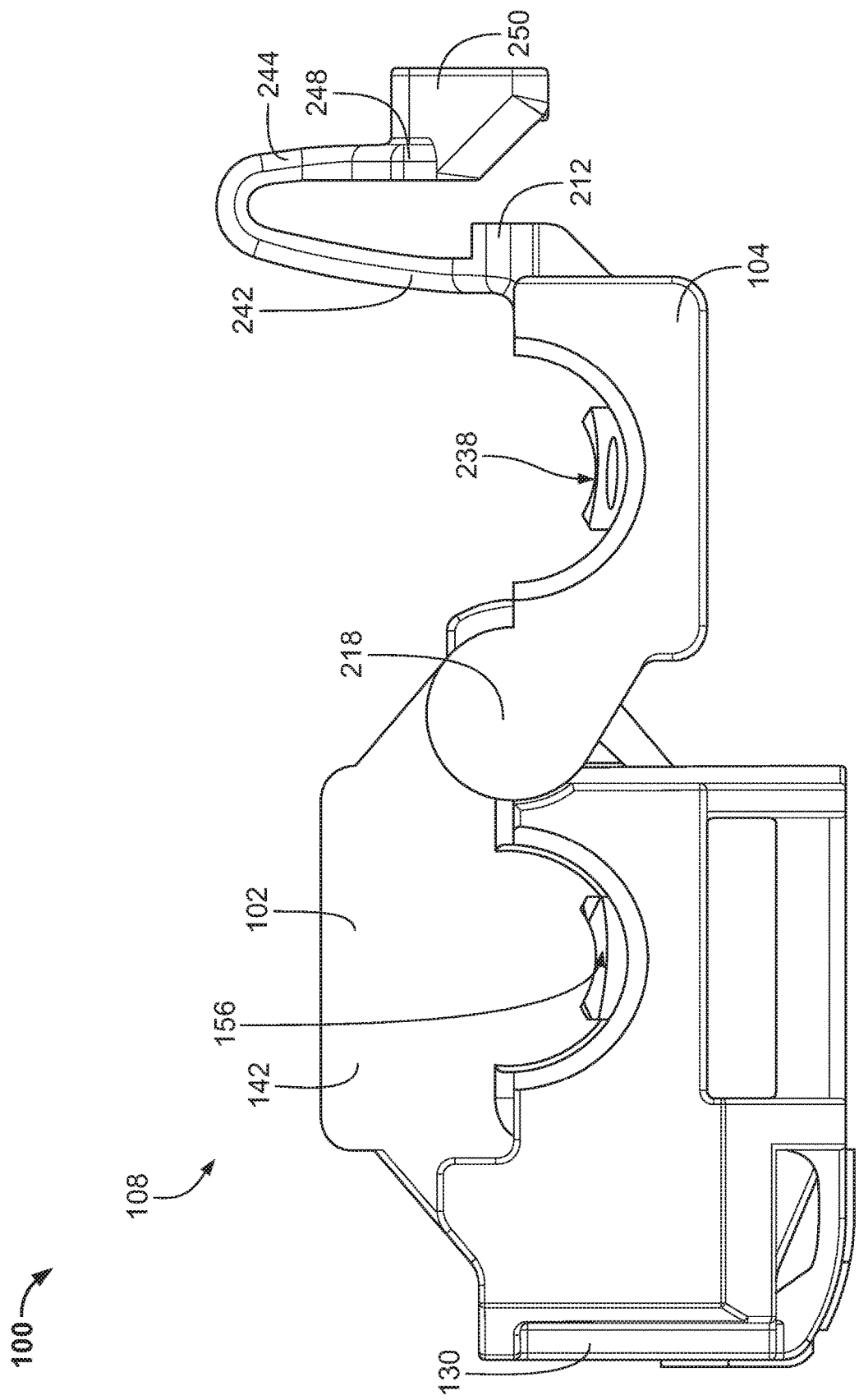
FIG. 8 is a bottom view of the first example fastener of FIGS. 1-7 in the open state.

With reference to FIG. 7, the clamp 104 is pivotably engaged with the body 102. More specifically, the first pin 182 is inserted into the hinge well 282 to pivotably engage the second hinge socket 218. Further, the first pin 182 is pivotably engaged with and stabilized by the pin hook 232. Additionally, as the first pin 182 is inserted into the second hinge socket 218, the first snap lip 184 snaps past the pin hook 232. Thus, the first snap lip 184 slidably and rotatably engages the pin hook 232 to retain the first pin 182 in the second hinge socket 218.

With reference to FIG. 3, to pivotably engage the clamp 104 with the body 102, the second pin 264 and the key 266 are inserted through the first hinge opening 200. The second pin 264 pivotably engages the fourth upper wall 188. Further, the key 266 slidably and rotatably engages the fourth upper wall 188 to retain the second pin 264 in the first hinge socket 136. The stop shoulder 192 provides a hard stop for the key 266 as the clamp 104 pivots relative to the body 102. Additionally, the stop shoulder 192 also ensures the latch clip 212 may be turned only toward the latch receiver 130 during initial assembly of the first example fastener 100.

With reference to FIG. 14, in operation, when the clamp 104 is pivoted relative to the body 102 to place the first example fastener 100 in the intermediate state 110, the latch clip 212 is inserted into the latch receiver 130. As the latch clip 212 is pushed into the latch receiver 130, the upper catch 246 slides against the upper shoulder 168 and the lower catch 248 slides against the lower shoulder 170. Further, as the upper catch 246 slides against the upper shoulder 168 and the lower catch 248 slides against the lower shoulder 170, the second resilient wall 244 resiliently flexes toward the first resilient wall 242. Additionally, as the upper catch 246 slides against the upper shoulder 168 and the lower catch 248 slides against the lower shoulder 170, the first resilient wall 242 resiliently flexes toward the second stud receiver 210.

Figure 15:
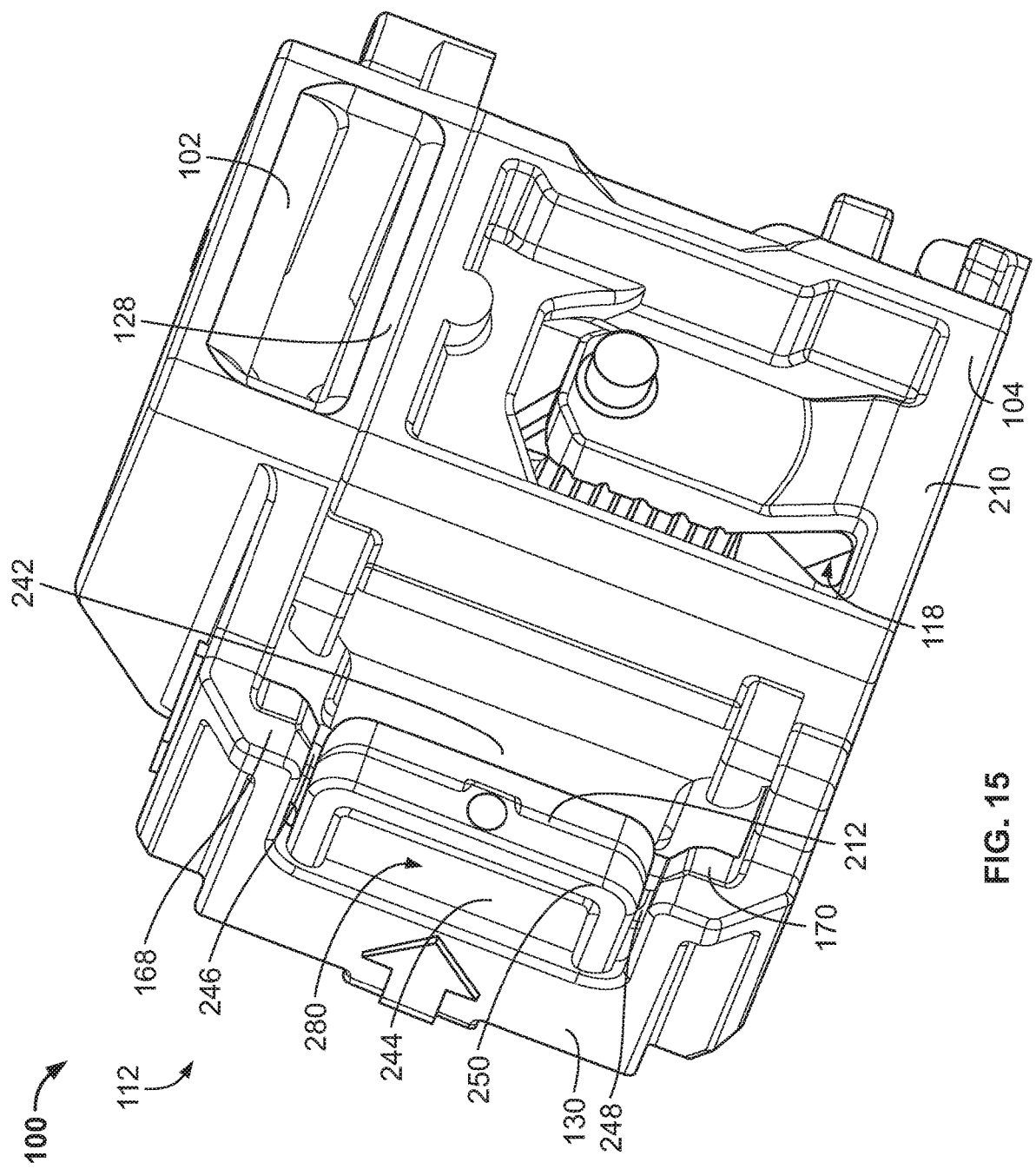
FIG. 15 is an isometric view of the first example fastener of FIGS. 1-7, 13, and 14 in a closed state.
Figure 16:
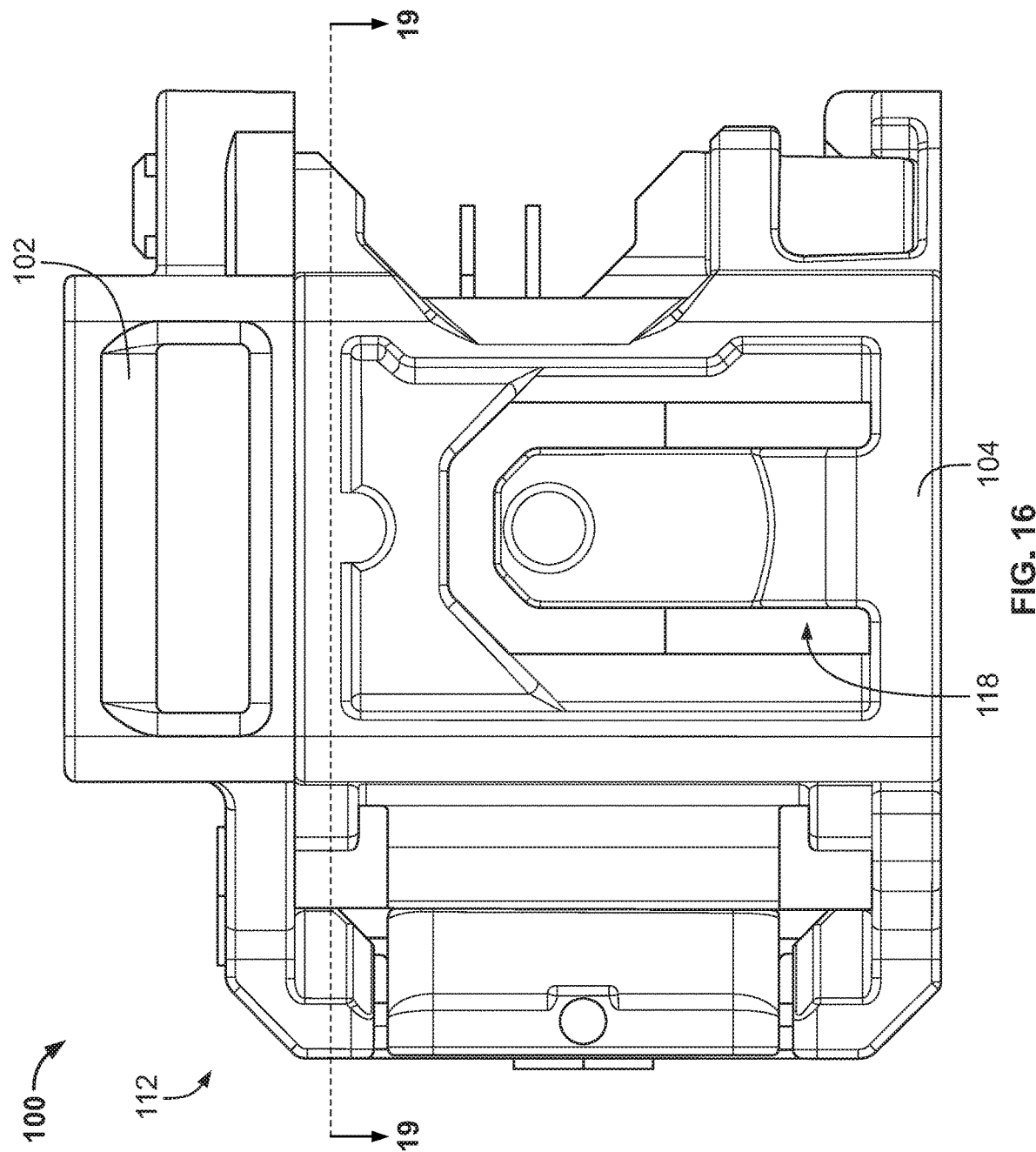
FIG. 16 is a front view of the first example fastener of FIGS. 1-7 and 13-15 in the closed state.
Figure 17:
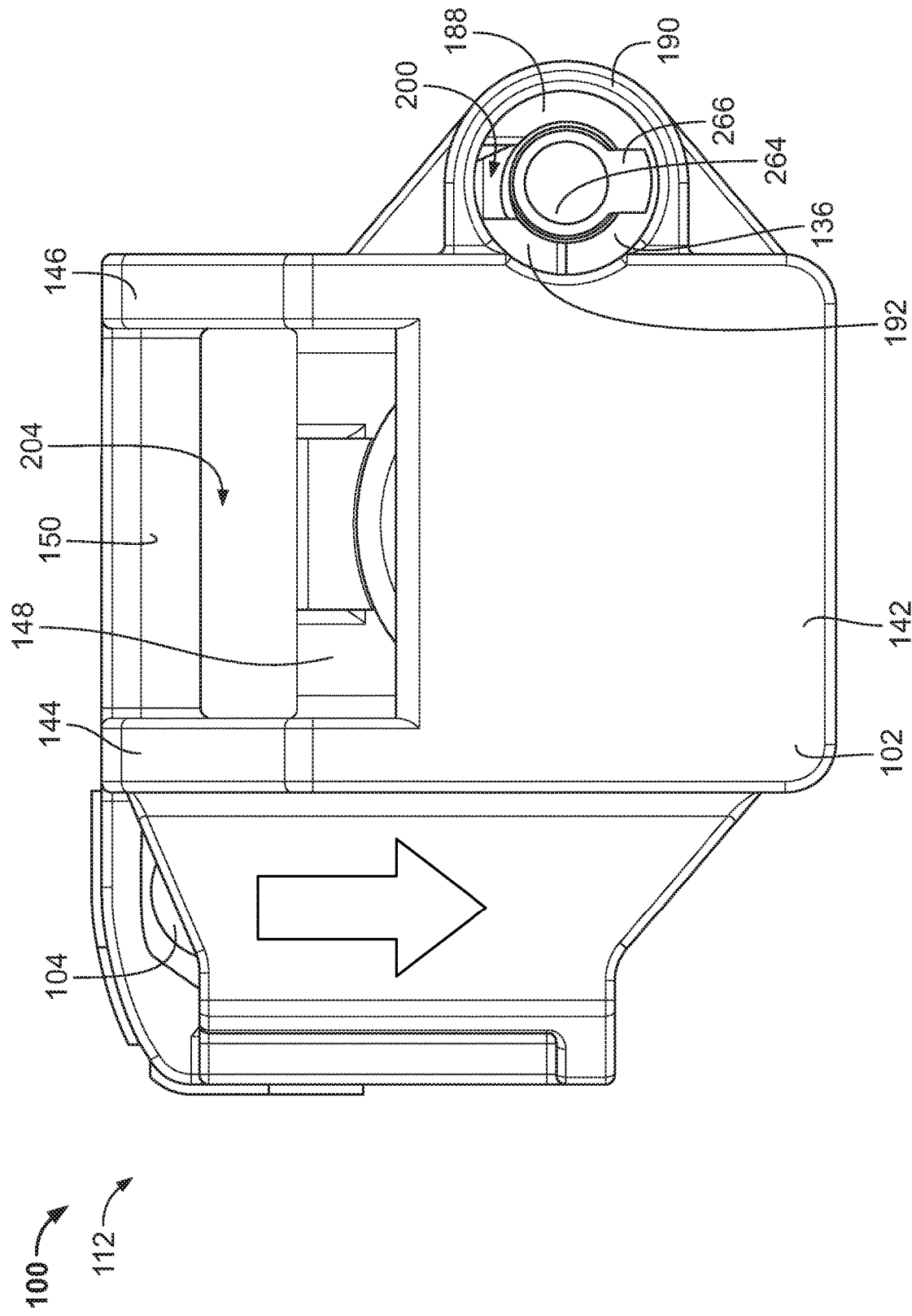
FIG. 17 is a top view of the first example fastener of FIGS. 1-7 and 13-16 in the closed state.

With reference to FIG. 15, in operation, as the latch clip 212 is pushed yet further into the latch receiver 130, the upper catch 246 slides past the upper shoulder 168 and the lower catch 248 slides past the lower shoulder 170. When the upper catch 246 slides past the upper shoulder 168 and the lower catch 248 slides past the lower shoulder 170, the first resilient wall 242 and the second resilient wall 244 resiliently snap away from the second stud receiver 210. When the first resilient wall 242 and the second resilient wall 244 resiliently snap away from the second stud receiver 210, the upper catch 246 snapably engages the upper shoulder 168, as shown in FIG. 19. The lower catch 248 snapably engages the lower shoulder 170 in the same manner as the upper catch 246 engages the upper shoulder 168, as shown in FIG. 15. Thus, the latch clip 212 is snapably retained in the latch receiver 130 when the first example fastener 100 is in the closed state 112.

Figure 21:
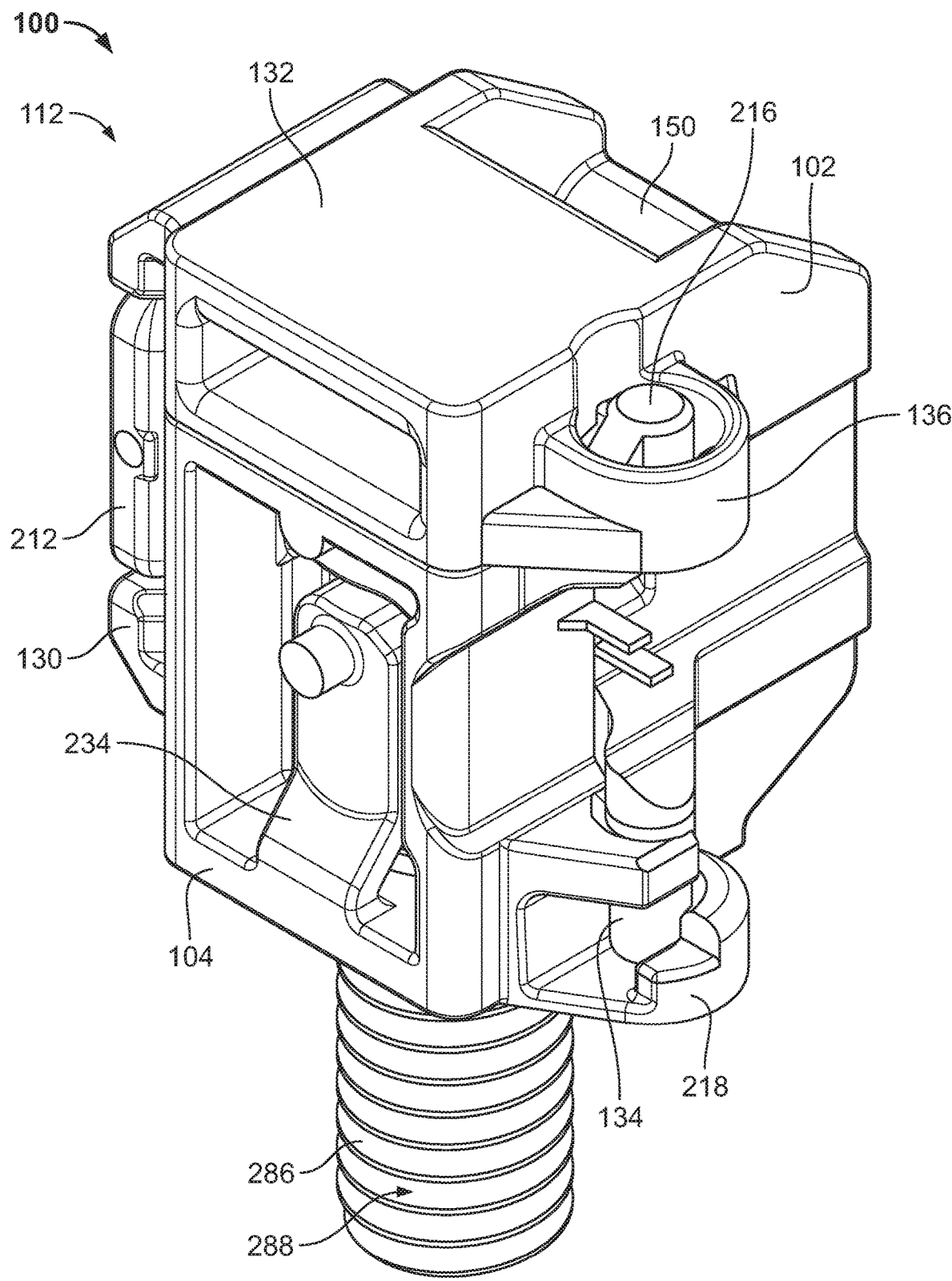
FIG. 21 is an isometric view of the first example fastener of FIGS. 1-7 and 13-20 assembled onto a stud.
Figure 22:
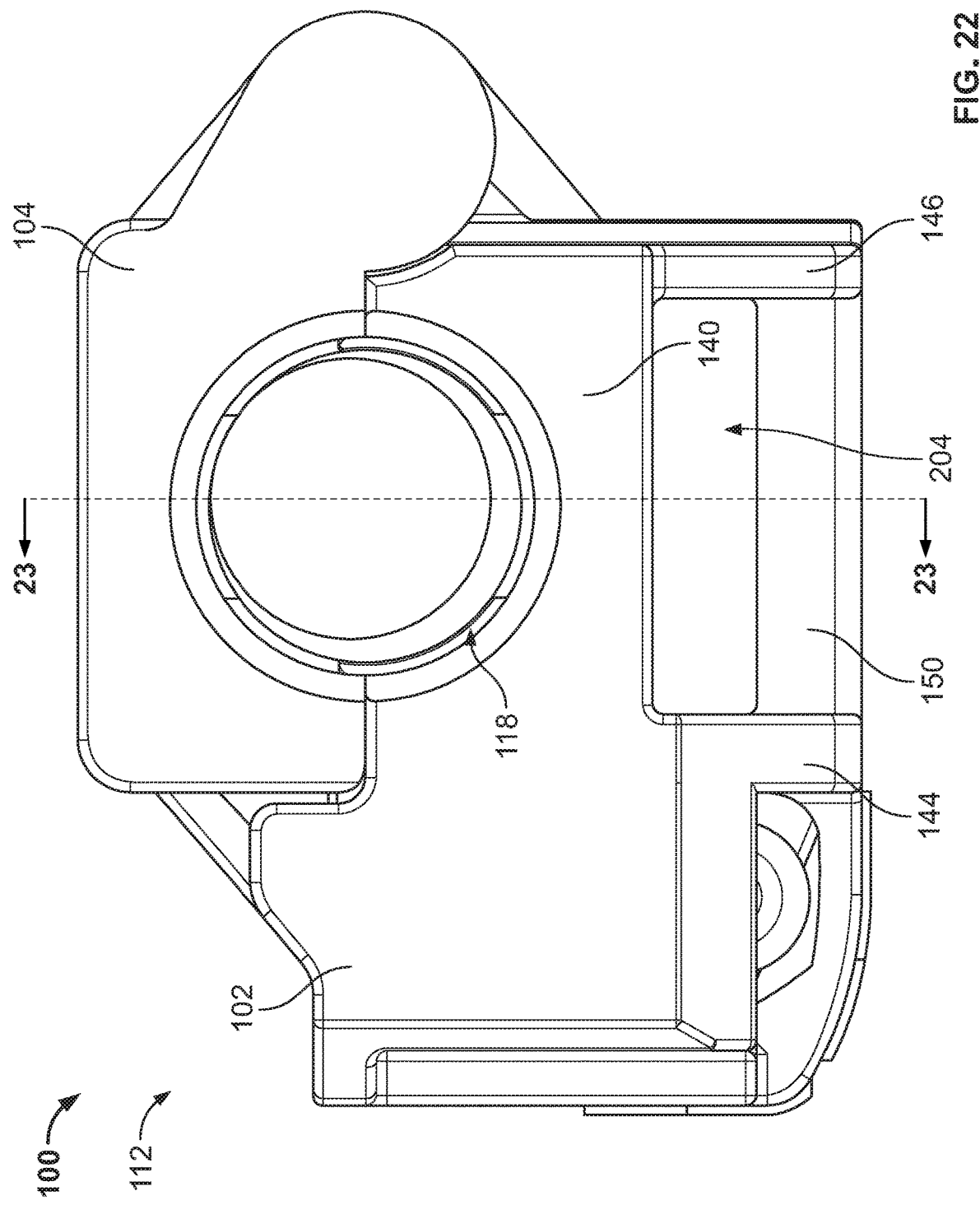
FIG. 22 is a bottom view of the first example fastener of FIGS. 1-7 and 13-21 assembled onto the stud of FIG. 21.
Figure 23:
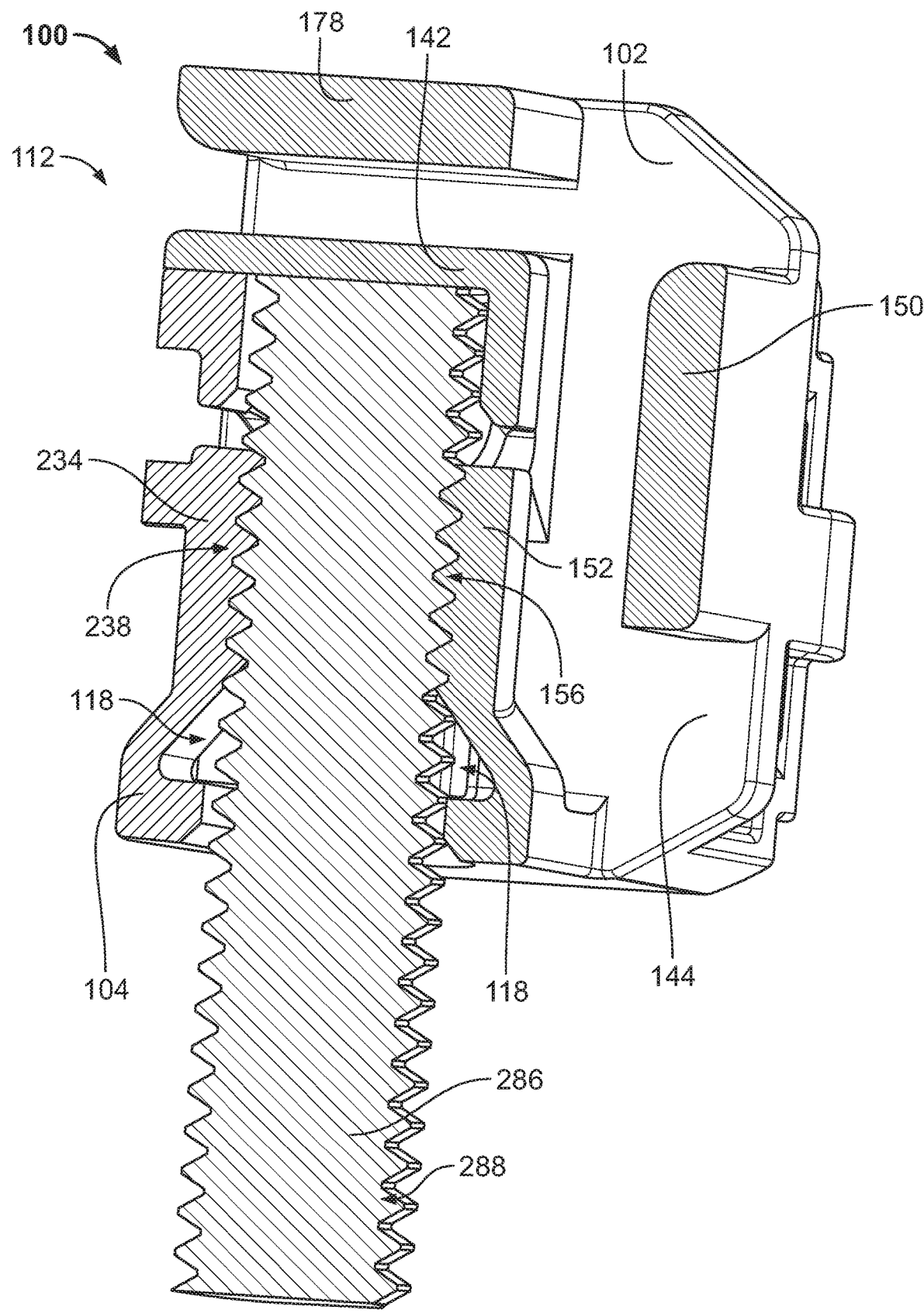
FIG. 23 is a cross-sectional view of the first example fastener of FIGS. 1-7 and 13-22 assembled onto the stud of FIGS. 22 and 23 taken along line 23-23 of FIG. 22.

With reference to FIG. 21, the first example fastener 100 is configured to engage a stud 286. The stud 286 includes external threads 288. With reference to FIG. 23, in operation, the first example fastener 100 receives the stud 286 via the stud cavity 118. When the stud 286 is inserted into the stud cavity 118, the first set of teeth 156 and the second set of the teeth 238 ratchetingly engage the external threads 288. More specifically, as the stud 286 is pushed into the stud cavity 118, the first resilient arm 152 and the second resilient arm 234 flex away from one another and snappingly return toward one another as the external threads 288 ratchetingly slide along the first set of teeth 156 and the second set of teeth 238. Further in operation, the stud 286 contacts the first upper wall 142. The first upper wall 142 provides a hard stop to the stud 286. Thus, the stud 286 is not pushed through the first example fastener 100.

With reference to FIG. 23, further in operation, if a force is applied to remove the stud 286 from the first example fastener 100, the external threads 288 pull against the first set of teeth 156 and the second set of teeth 238. When the external threads 288 pull against the first set of teeth 156 and the second set of teeth 238, the first resilient arm 152 and the second resilient arm 234 are pulled toward one another. Thus, pulling the stud 286 and the first example fastener 100 from one another tightens the first set of teeth 156 and the second set of teeth 238 against the external threads 288. Thus, the first example fastener 100 is securely retained on the stud 286.

With reference to FIG. 15, further in operation, a tool (e.g., a screwdriver) (not shown) may be inserted into the tool pocket 280 and pushed against the release wall 250 and the second resilient wall 244. When the tool is pushed against the release wall 250 and the second resilient wall 244, the first resilient wall 242 and the second resilient wall 244 flex inwardly toward the first stud receiver 128 and the second stud receiver 210. As the first resilient wall 242 and the second resilient wall 244 flex inwardly toward the first stud receiver 128 and the second stud receiver 210, the upper catch 246 is released from the upper shoulder 168 and the lower catch 248 is released from the lower shoulder 170. When the upper catch 246 is released from the upper shoulder 168 and the lower catch 248 is released from the lower shoulder 170, the clamp 104 is free to pivot away from the body 102. Thus, the clamp 104 releasably mates with the body 102. Further, with reference to FIG. 23, the stud 286 may thus be freed from the first set of teeth 156 and the second set of teeth 238 and released from the first example fastener 100. Additionally or alternatively, a finger of an operator may also be inserted into the tool pocket 280 and pushed against the release wall 250 and the second resilient wall 244 in the same manner as the tool to release the clamp 104 from the body 102.

Figure 24:
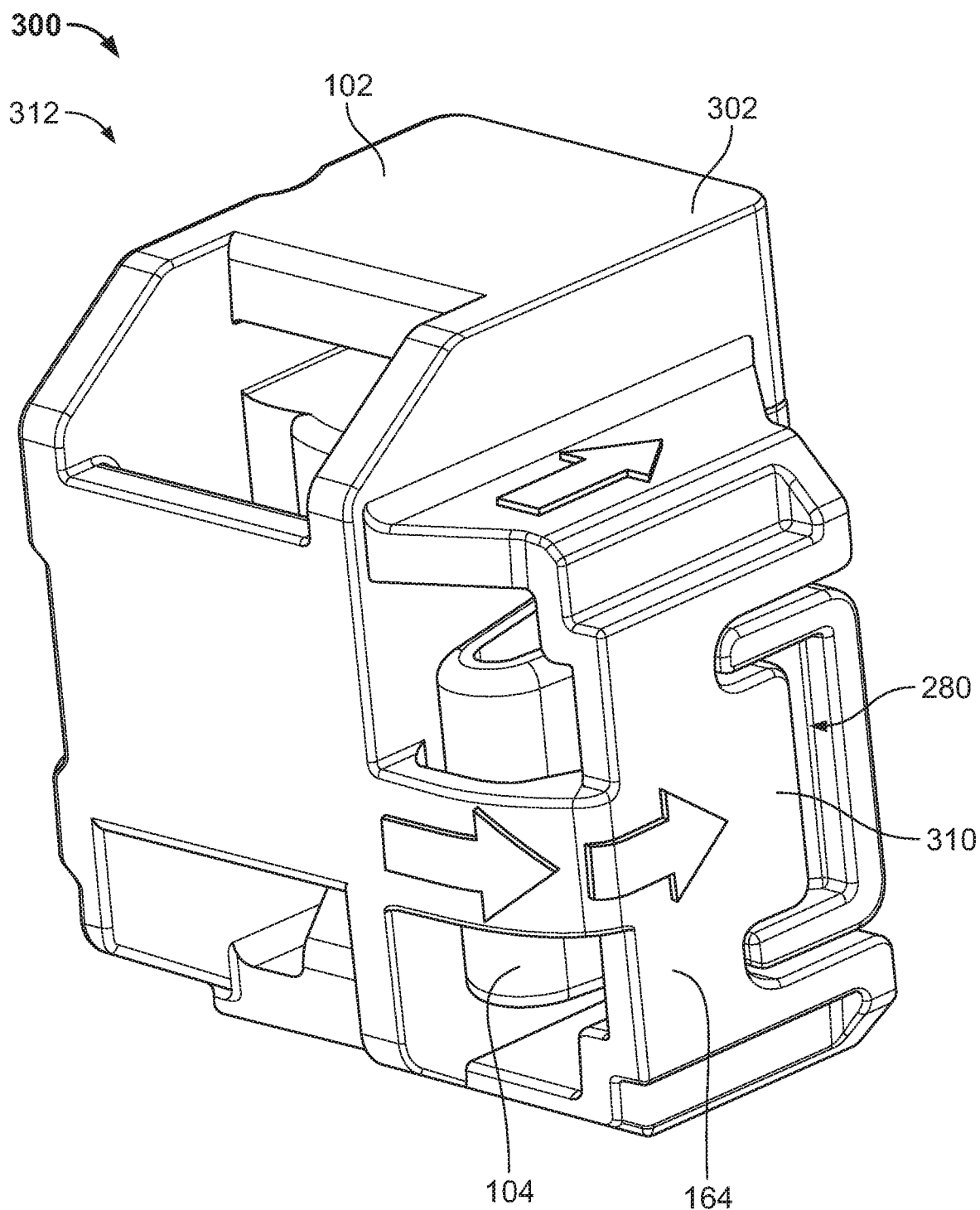
FIG. 24 is an isometric view of a second example fastener according to an embodiment of the present disclosure.

With reference to FIG. 24, a second example fastener 300 includes a body 302. The second example fastener 300 further includes the clamp 104 described above. The body 302 includes the body 102 of the first example fastener 100 describe above. The body 302 further includes a guard wall 310. The guard wall 310 is connected to and extends from the third side wall 164. When the second example fastener 300 is in a closed state 312, the guard wall 310 extends into the tool pocket 280. The guard wall 310 aids in preventing inadvertent release of the clamp 104 from the body 302.

Figure 25:
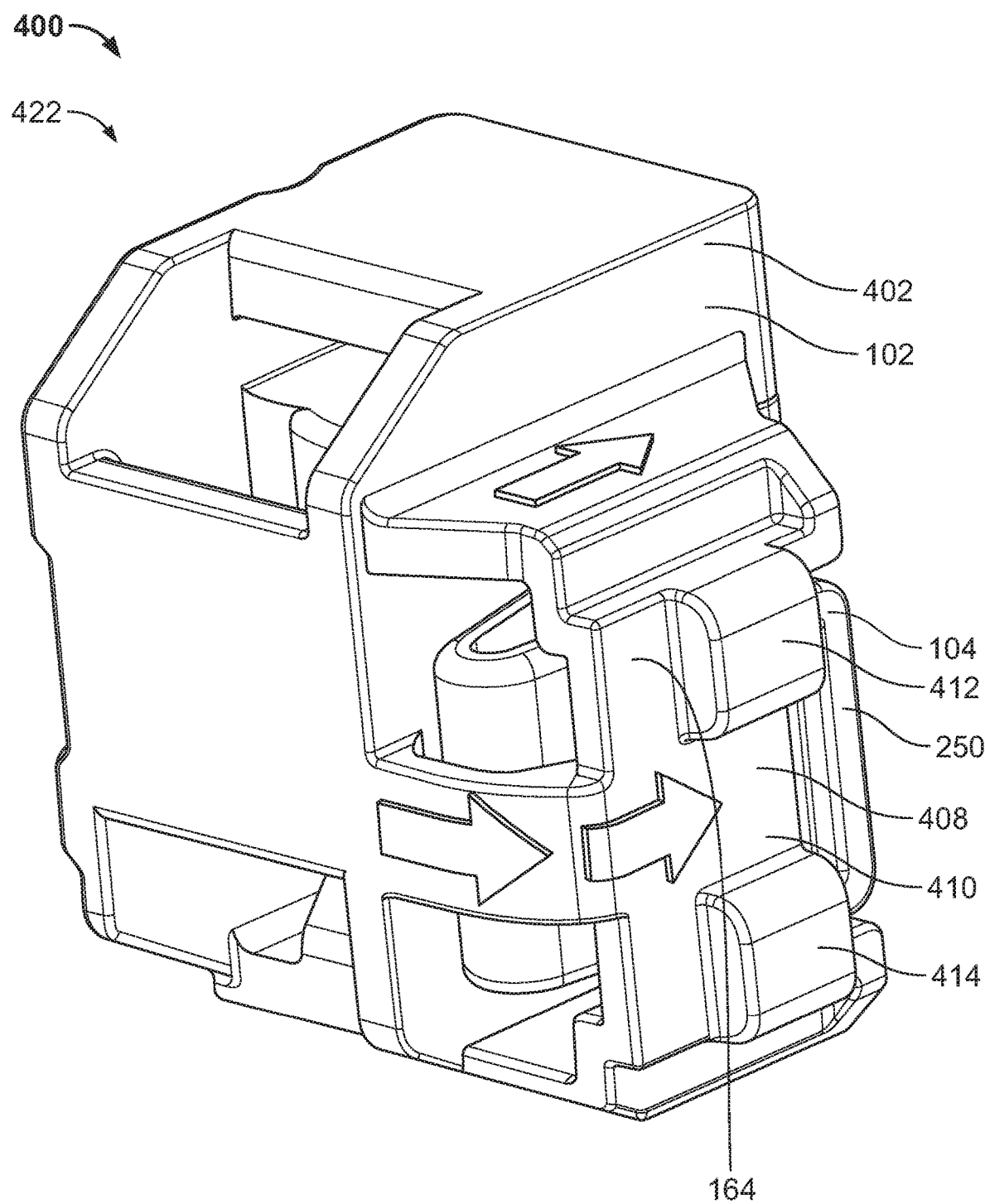
FIG. 25 is an isometric view of a third example fastener according to an embodiment of the present disclosure.
Figure 26:
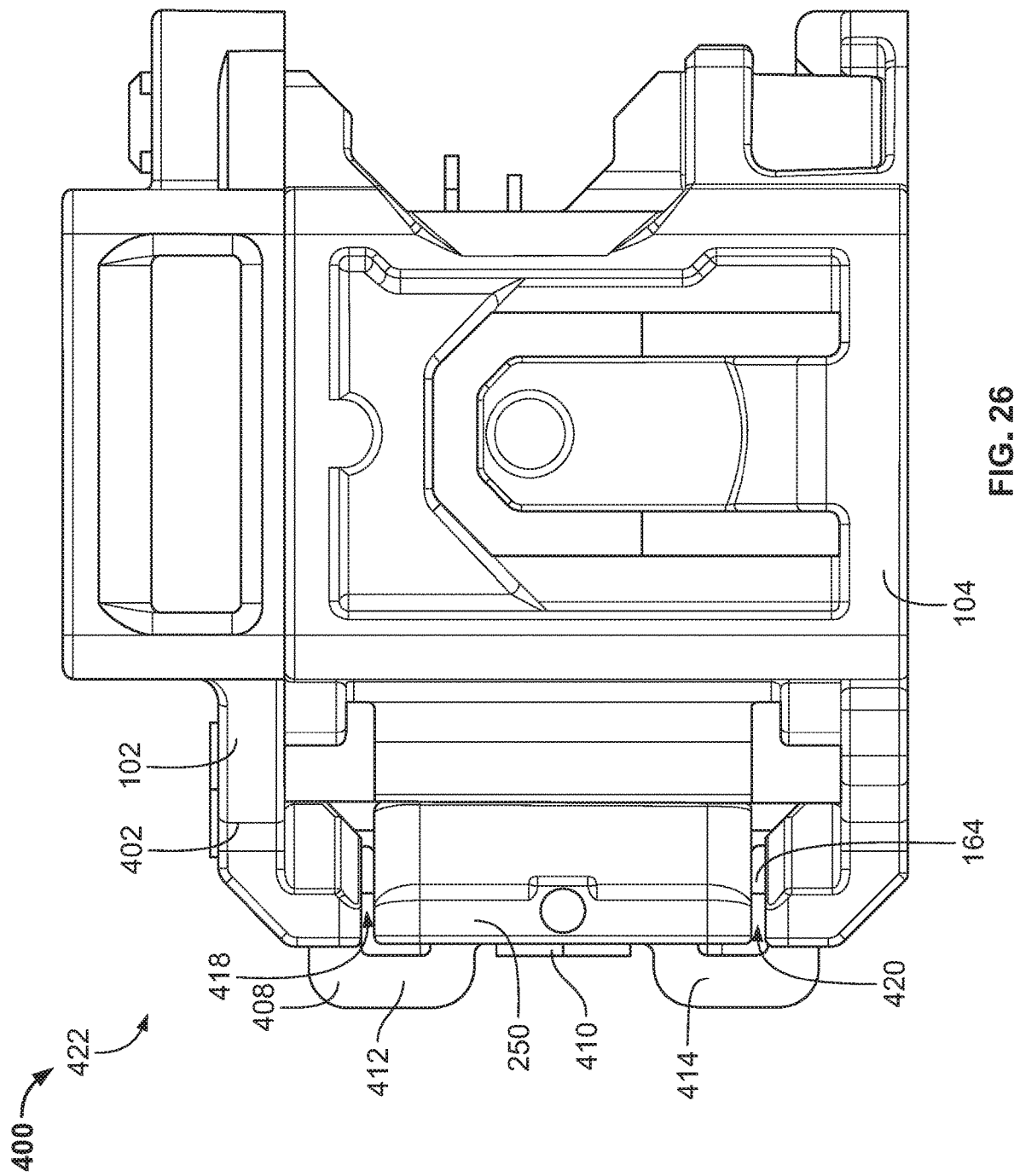
FIG. 26 is a front view of the third example fastener of FIG. 25.

With reference to FIGS. 25 and 26 a third example fastener 400 includes a body 402. The third example fastener 400 further includes the clamp 104 described above. The body 402 includes the body 102 of the first example fastener 100 described above. The body 402 further includes a release guard 408. The release guard 408 extends from and is connected the third side wall 164. The release guard 408 includes a guard wall 410, an upper guard loop 412 and a lower guard loop 414. With reference to FIG. 26, the upper guard loop 412 defines an upper channel 418. The lower guard loop 414 defines a lower channel 420. When the third example fastener 400 is in a closed state 422, the release wall 250 is received in the upper channel 418 and the lower channel 420. The release guard 408 aids in preventing inadvertent release of the clamp 104 from the body 402.

Figure 27:
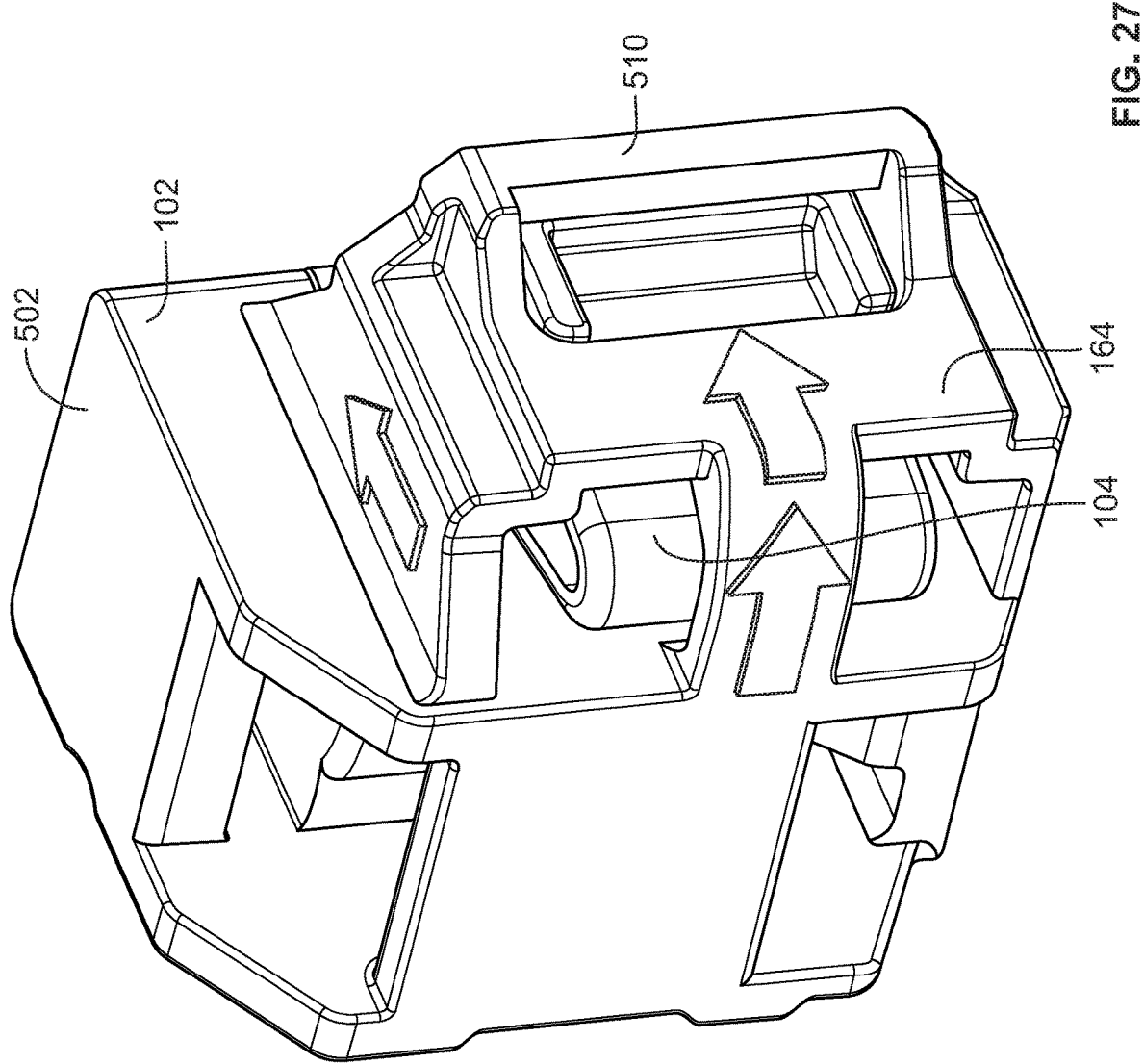
FIG. 27 is an isometric view of a fourth example fastener according to an embodiment of the present disclosure.

With reference to FIG. 27, a fourth example fastener 500 includes a body 502. The fourth example fastener 500 further includes the clamp 104 described above. The body 502 includes the body 102 of the first example fastener 100 described above. The body 502 further includes a guard loop 510. The guard loop 510 is connected to and extends outwardly from the third side wall 164. The guard loop 510 aids in preventing inadvertent release of the clamp 104 from the body 502.

Figure 28:
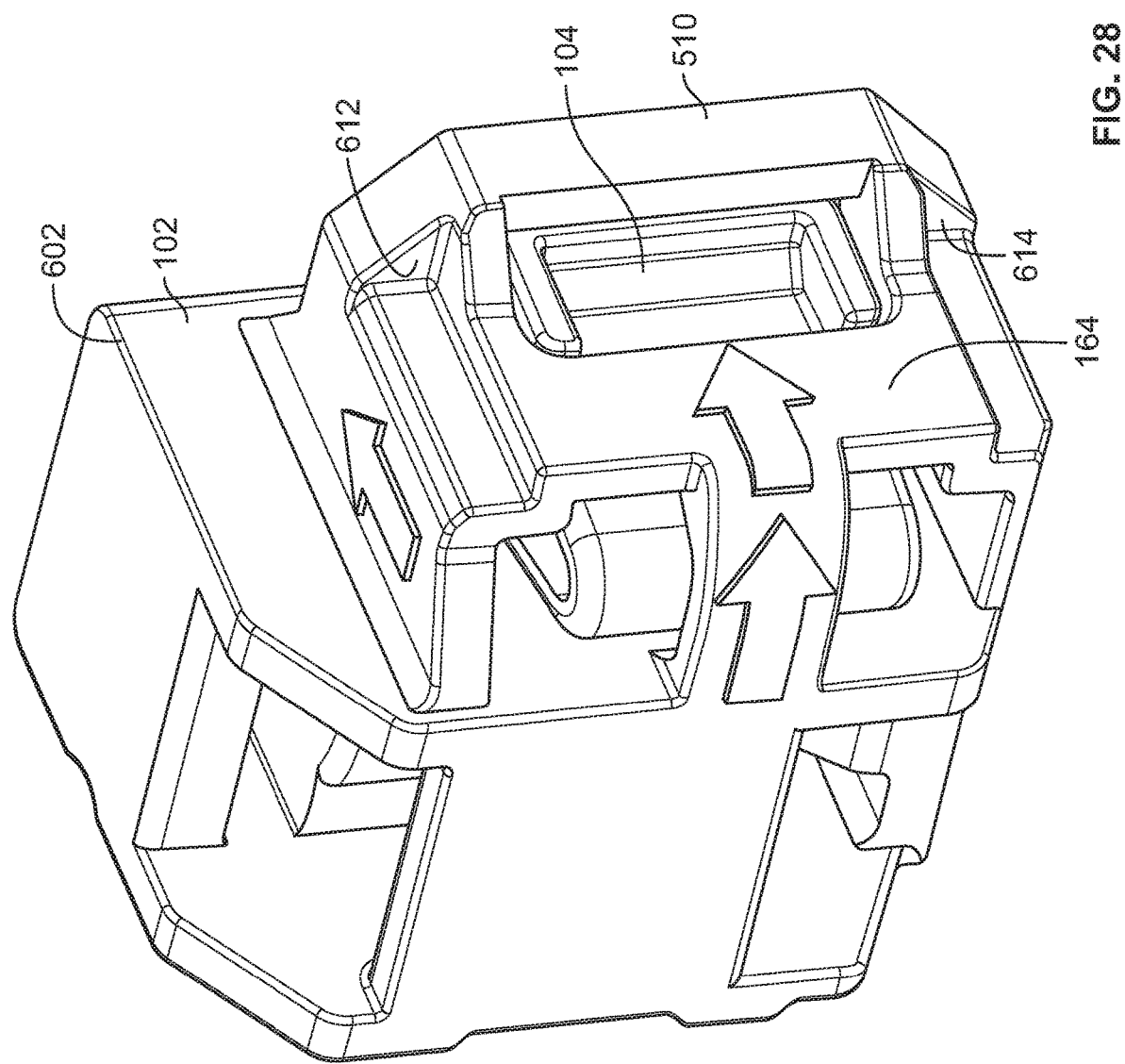
FIG. 28 is an isometric view of a fifth example fastener according to an embodiment of the present disclosure.

With reference to FIG. 28, a fifth example fastener 600 includes a body 602. The fifth example fastener 600 further includes the clamp 104 described above. The body 602 includes the body 102 of the first example fastener 100 described above. The body 602 further includes the guard loop 510 described above with reference to FIG. 27. The body 602 also includes an upper rib 612 and a lower rib 614. The upper rib 612 is connected to the second upper wall 162 and the guard loop 510. The lower rib 614 is connected to the second lower wall 160 and the guard loop 510. The upper rib 612 and the lower rib 614 provide support to and strengthen the guard loop 510.

Figure 39:
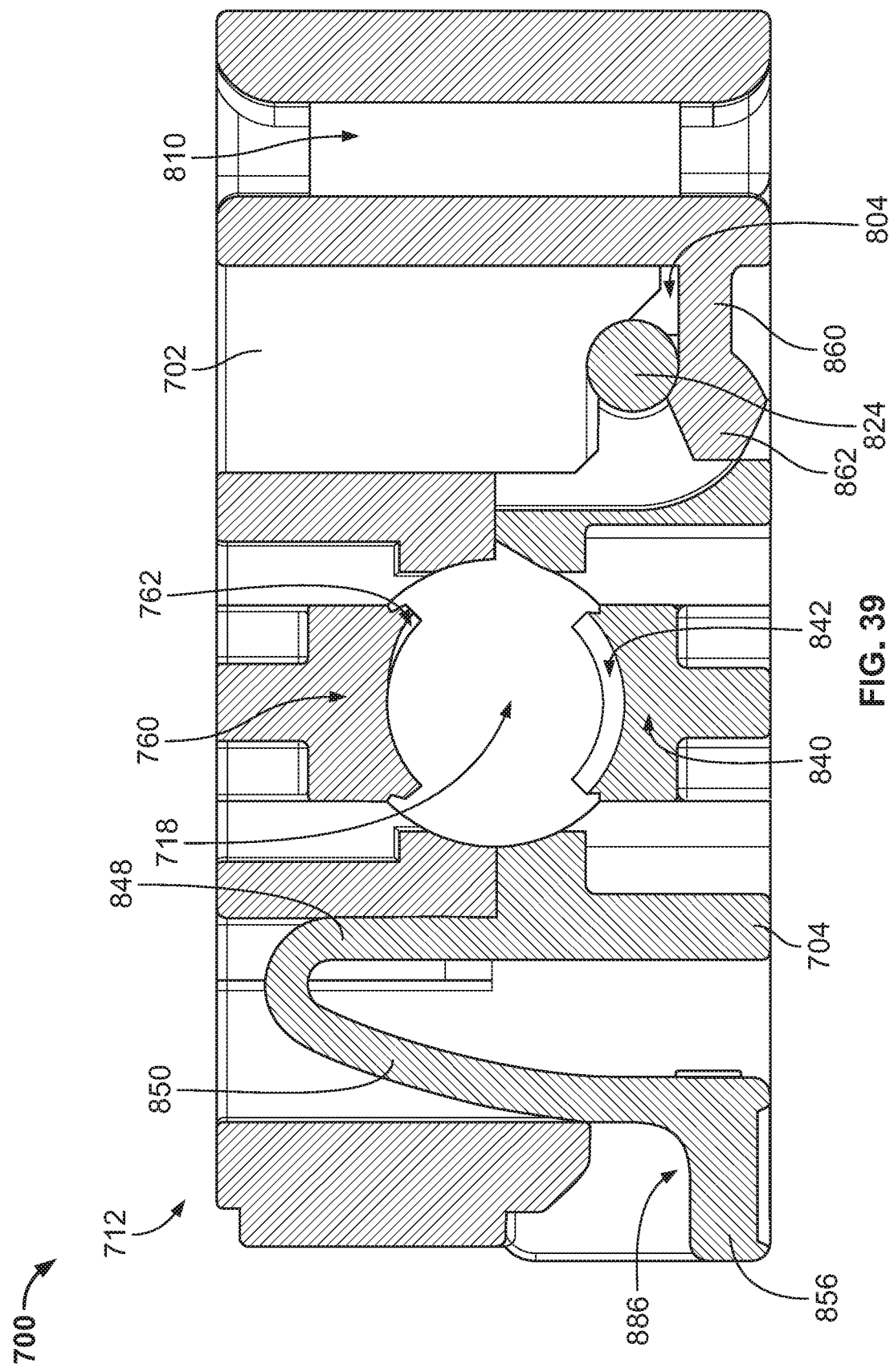
FIG. 39 is a cross-sectional view of the sixth example fastener of FIGS. 29-34 taken along line 39-39 of FIG. 31.
Figure 40:
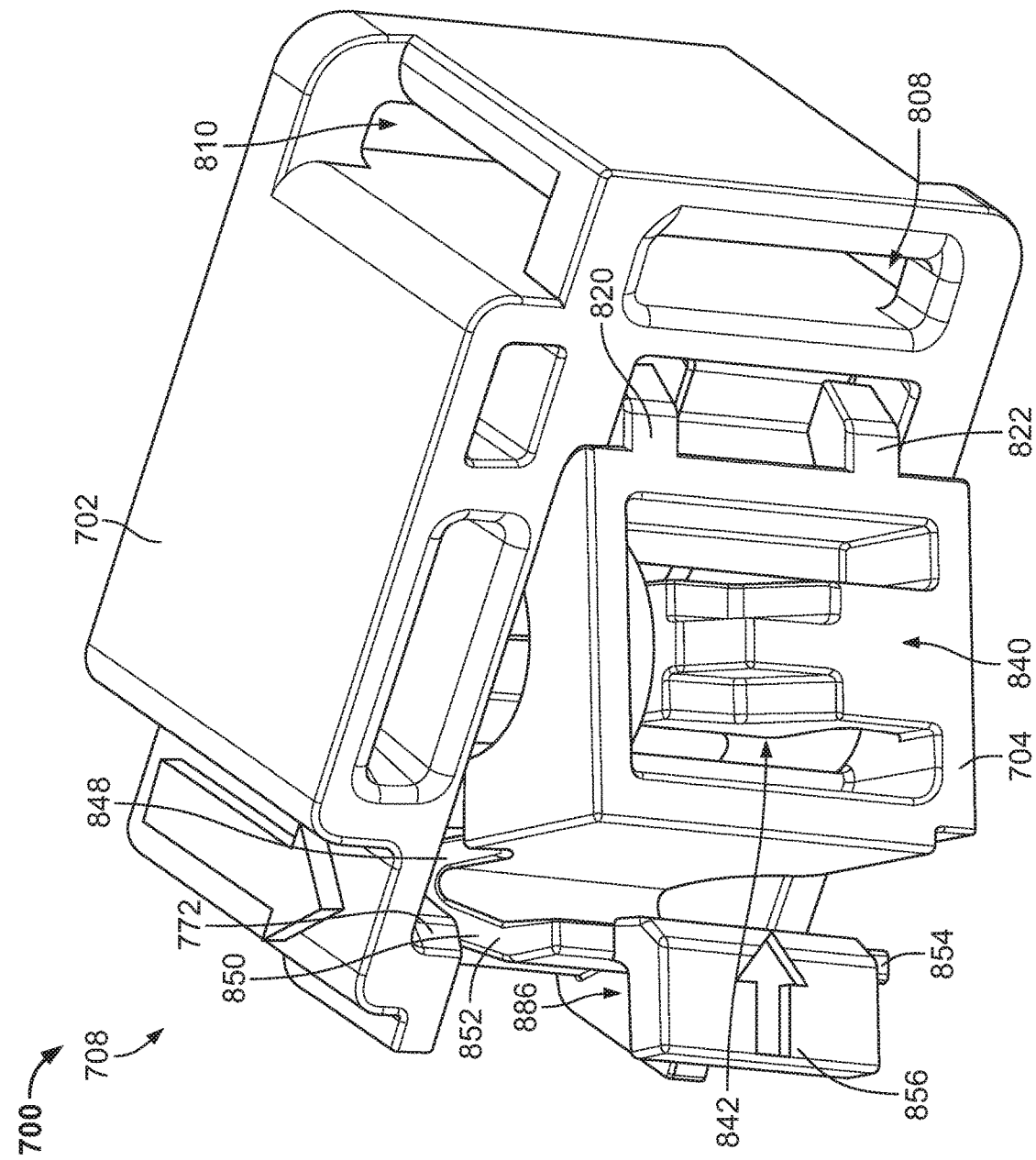
FIG. 40 is an isometric view of the sixth example fastener of FIGS. 29-34 and 39 in an intermediate state.

With reference to FIGS. 29-34, 39, and 40, a sixth example fastener 700 includes a body 702 and a clamp 704. With reference to FIG. 40, the sixth example fastener 700 is shown in an open state 708. With reference to FIGS. 29-34 and 39, the sixth example fastener 700 is shown in a closed state 712.

Figure 30:
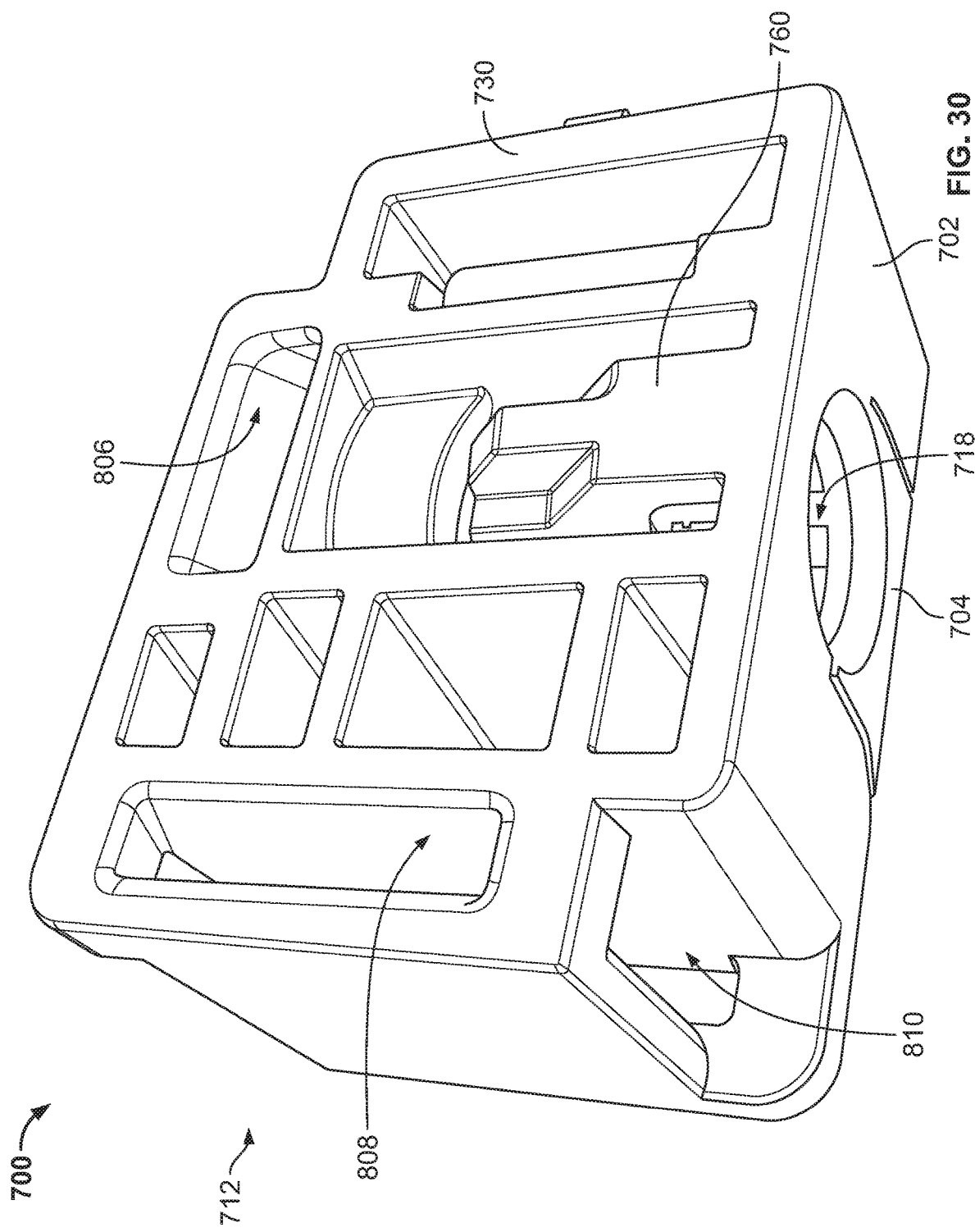
FIG. 30 is another isometric view of the sixth example fastener of FIG. 29 in the closed state.
Figure 34:
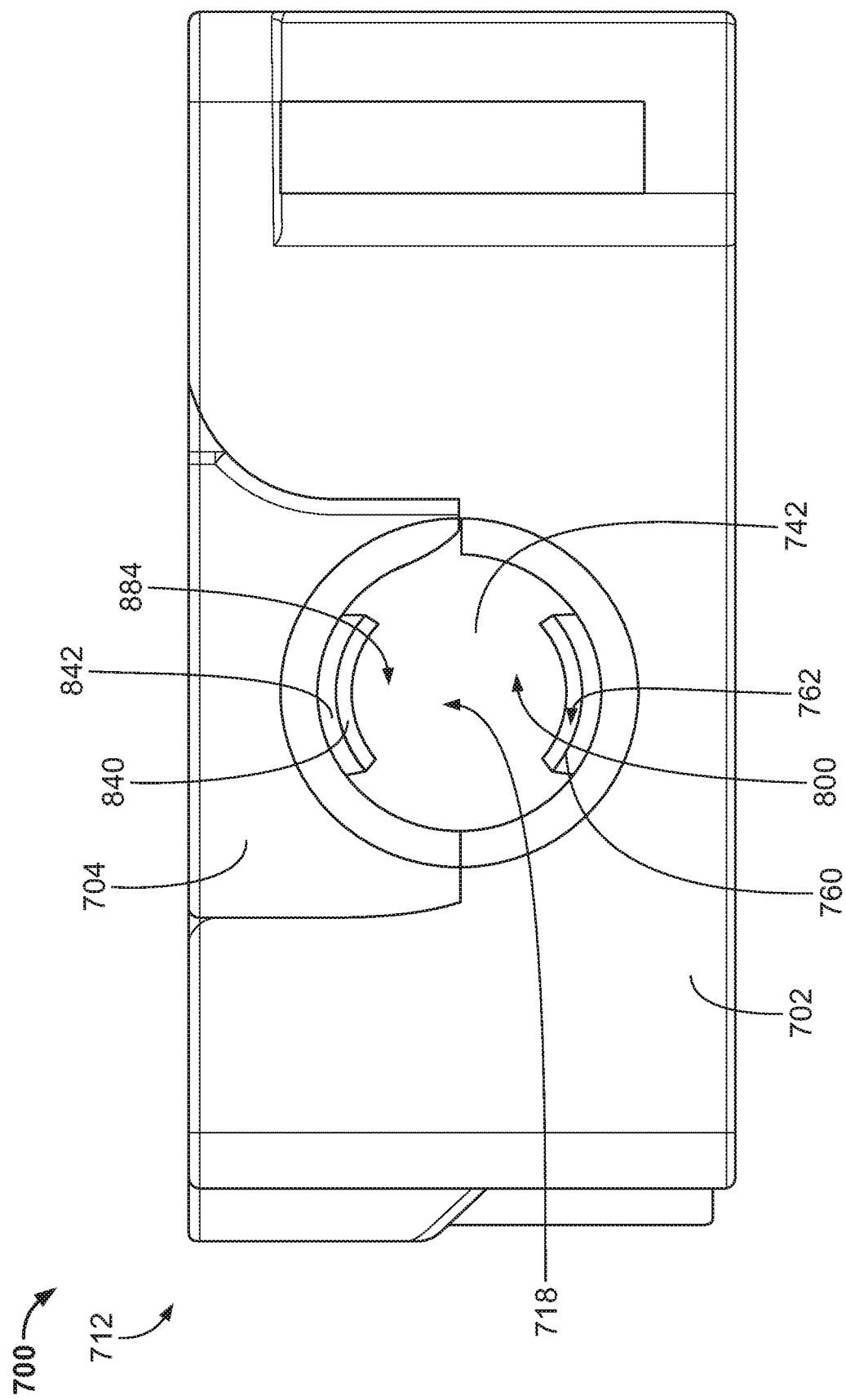
FIG. 34 is a bottom view of the sixth example fastener of FIGS. 29-33 in the closed state.

With reference to FIGS. 30, 34, and 39, the body 702 is pivotably connected to the clamp 704. The clamp 704 selectively latchably secures in the body 702. When the sixth example fastener 700 is in the closed state 712 with the clamp 704 latched in the body 702, the body 702 and the clamp 704 define a stud cavity 718.

Figure 29:
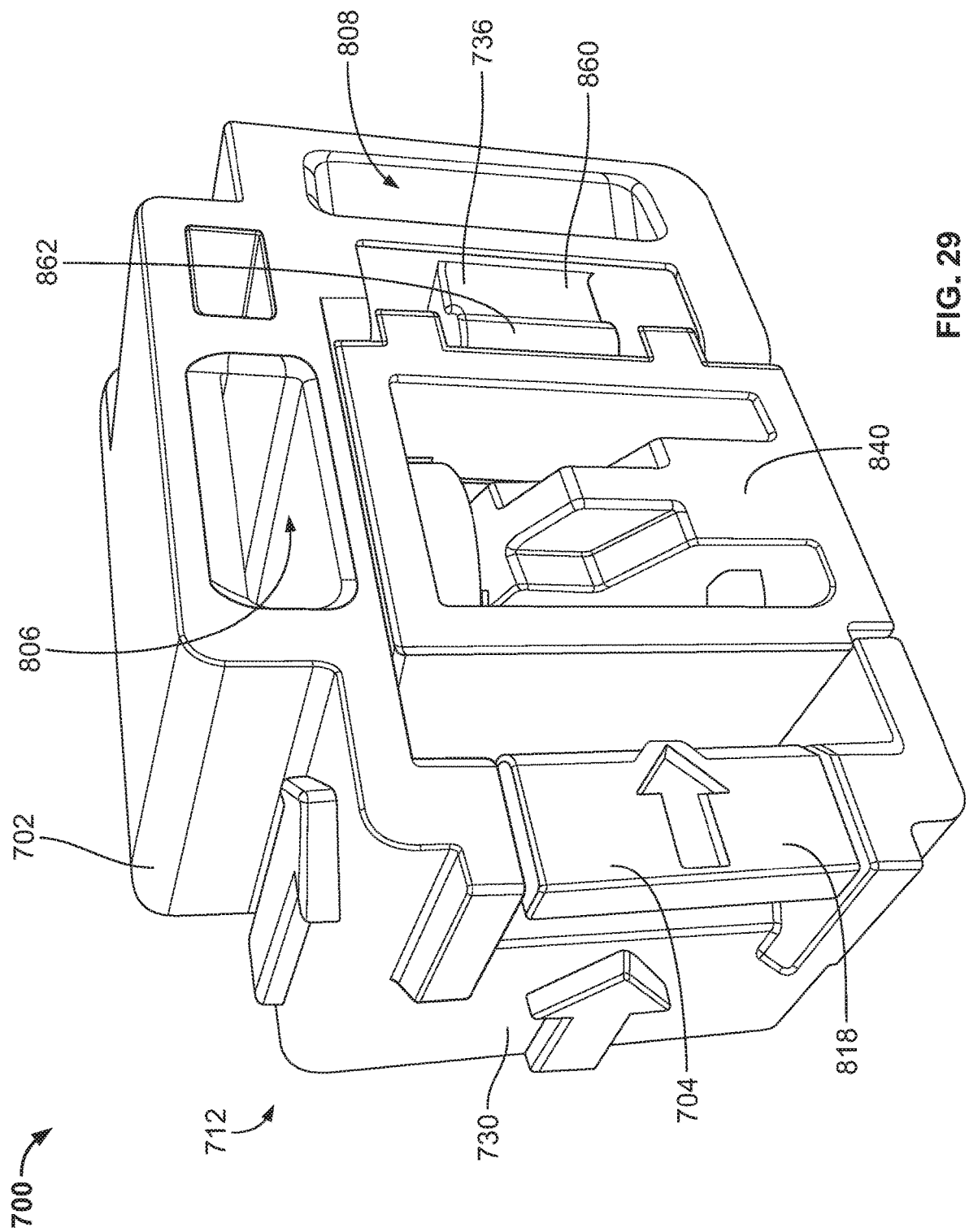
FIG. 29 is an isometric view of a sixth example fastener according to an embodiment of the present disclosure in a closed state.

With reference to FIG. 29, the sixth example fastener 700 may be made of a polymer plastic (e.g., polyamide (PA), polyoxymethylene (POM), Acrylonitrile butadiene styrene (ABS), etc.).

Figure 35:
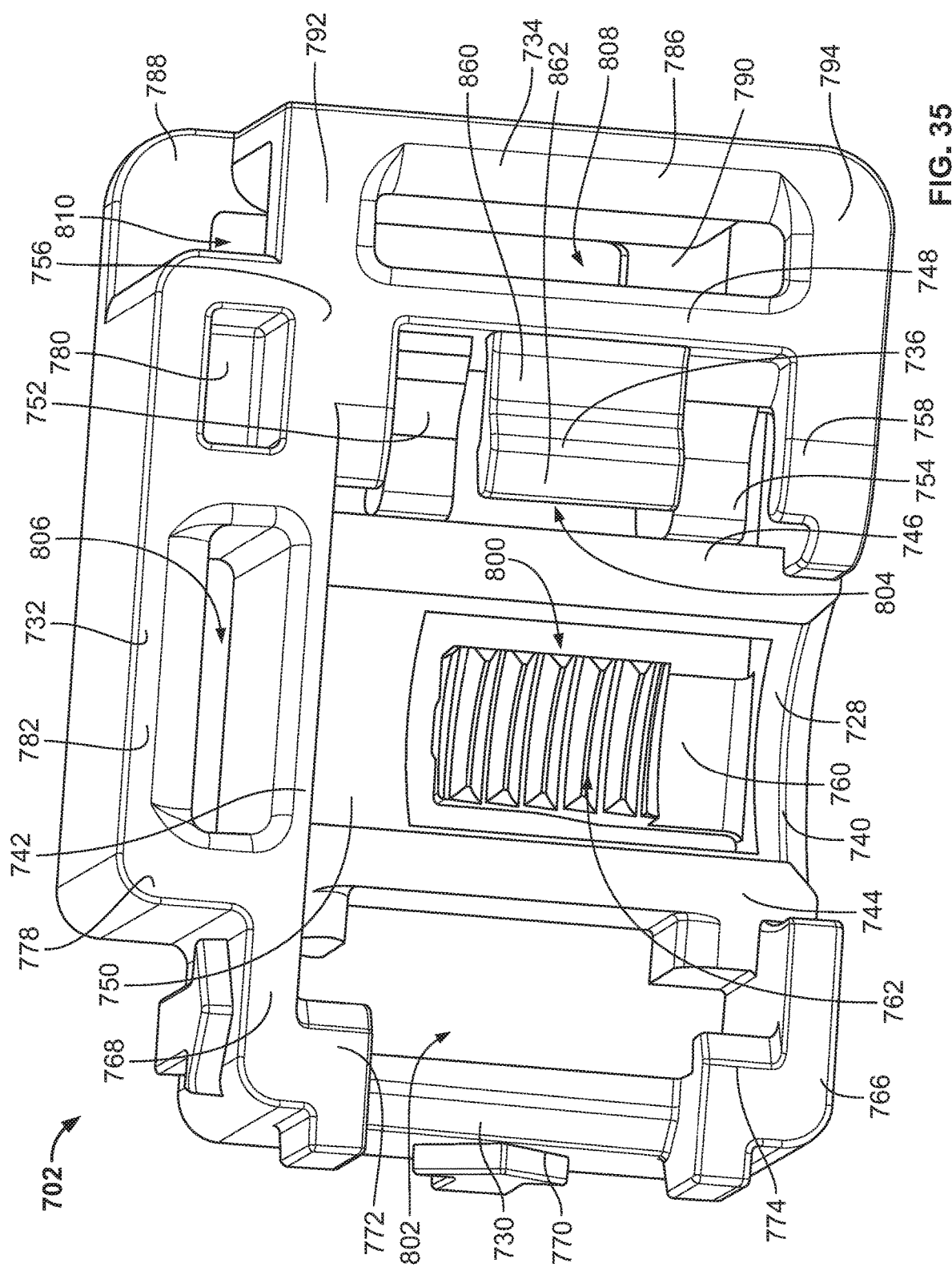
FIG. 35 is an isometric view of a body of the sixth example fastener of FIGS. 29-34.

With reference to FIG. 35, the body 702 includes a first stud receiver 728, a latch receiver 730, a first loop 732, a second loop 734 and a hinge tongue 736. The latch receiver 730, the first loop 732, the second loop 734, and the hinge tongue 736 are connected to the first stud receiver 728. The first stud receiver 728 is between the latch receiver 730 and the second loop 734. The first loop 732 is between the latch receiver 730 and the second loop 734.

With reference to FIG. 35, the first stud receiver 728 includes a first lower wall 740, a first upper wall 742, a first side wall 744, a second side wall 746, a third side wall 748, a first rear wall 750, a second rear wall 752, a third rear wall 754, a first shoulder 756, a second shoulder 758, and a first resilient arm 760. The first resilient arm 760 includes a first set of teeth 762. The first lower wall 740 is connected to the first side wall 744 and the second side wall 746. The first upper wall 742 is connected to the first side wall 744 and the second side wall 746. The first rear wall 750 is connected to the first side wall 744, the second side wall 746, and the first upper wall 742. The second rear wall 752 is connected to the second side wall 746 and the third side wall 748. The third rear wall 754 is connected to the second side wall 746 and the third side wall 748. The first resilient arm 760 is connected to and extends from the first lower wall 740 toward the first upper wall 742. The first set of teeth 762 extend inwardly. In other words, the first set of teeth extend away from the first rear wall 750.

With reference to FIG. 35, the latch receiver 730 includes a second lower wall 766, a second upper wall 768, a fourth side wall 770, a third shoulder 772, and a fourth shoulder 774. The second lower wall 766 is connected to and extends from the first lower wall 740. The second upper wall 768 is connected to and extends from the first upper wall 742. The fourth side wall 770 is connected to and between the second lower wall 766 and the second upper wall 768. The third shoulder 772 is connected to and extends from the second upper wall 768 and the fourth side wall 770. The fourth shoulder 774 is connected to and extends from the fourth side wall 770 and the second lower wall 766.

With reference to FIG. 35, the first loop 732 includes a fifth side wall 778, a first extension 780, and a third upper wall 782. The third upper wall 782 is connected to and between the fifth side wall 778 and the first extension 780. The first extension 780 is connected to and extends from the first upper wall 742. The fifth side wall 778 is connected to and extends from the first upper wall 742.

With reference to FIG. 35, the second loop 734 includes a sixth side wall 786, a fourth rear wall 788, a fifth rear wall 790, a first front wall 792, and a second front wall 794. The sixth side wall 786 is connected to the fourth rear wall 788, the fifth rear wall 790, the first front wall 792, and the second front wall 794. The fourth rear wall 788, the fifth rear wall 790, the first front wall 792, and the second front wall 794 are connected to and extend from the third side wall 748.

With reference to FIG. 35, the first stud receiver 728 defines a first stud pocket 800. More specifically, the first lower wall 740, the first upper wall 742, the first side wall 744, the second side wall 746, the first rear wall 750, and the first resilient arm 760 define the first stud pocket 800.

With reference to FIG. 35, the latch receiver 730 defines a latch pocket 802. More specifically, the second lower wall 766, the second upper wall 768, the fourth side wall 770, the third shoulder 772, and the fourth shoulder 774 define the latch pocket 802. The first side wall 744 further defines the latch pocket 802.

With reference to FIG. 35, the first stud receiver 728 defines a first a hinge pocket 804. More specifically, the hinge tongue 736, the first lower wall 740, the first upper wall 742, the third side wall 748, the second rear wall 752, the third rear wall 754, the first shoulder 756, and the second shoulder 758 define the hinge pocket.

Figure 36:
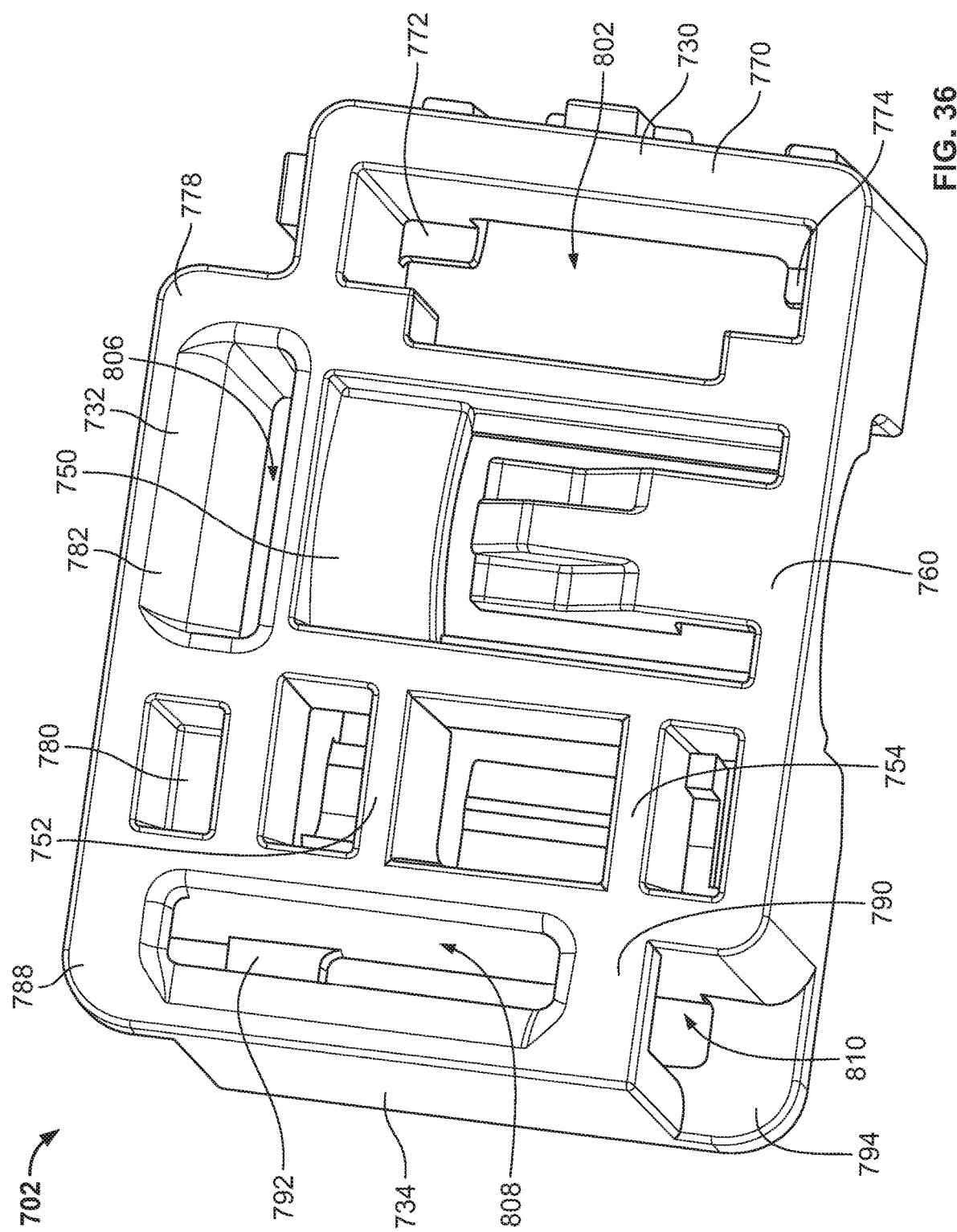
FIG. 36 is another isometric view of the body of FIG. 35.
Figure 37:
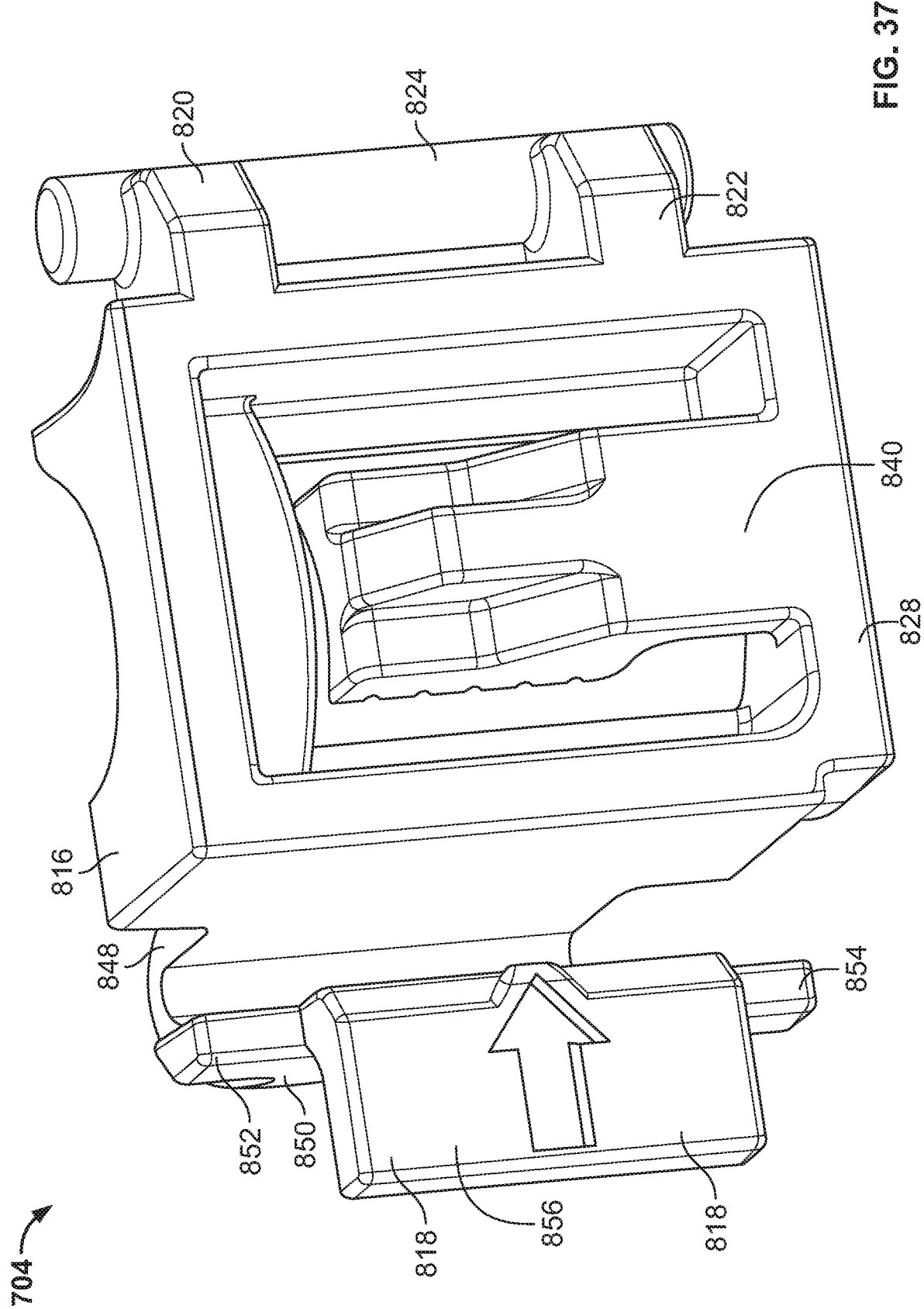
FIG. 37 is an isometric view of a clamp of the sixth example fastener of FIGS. 29-34.

With reference to FIGS. 35 and 36, the first loop 732 defines a first strap passage 806. More specifically, the fifth side wall 778, the first extension 780, and the third upper wall 782 define the first strap passage 806. The first upper wall 742 further defines the first strap passage 806.

With reference to FIGS. 35 and 36, the second loop 734 defines a second strap passage 808. More specifically, the sixth side wall 786, the fourth rear wall 788, the fifth rear wall 790, the first front wall 792, and the second front wall 794 define the second strap passage 808.

With reference to FIGS. 35 and 36, the second loop 734 also defines a third strap passage 810. More specifically, the sixth side wall 786, the fourth rear wall 788, the fifth rear wall 790, the first front wall 792, and the second front wall 794 define the third strap passage 810. Thus, the second strap passage 808 and the third strap passage 810 intersect one another.

Figure 38:
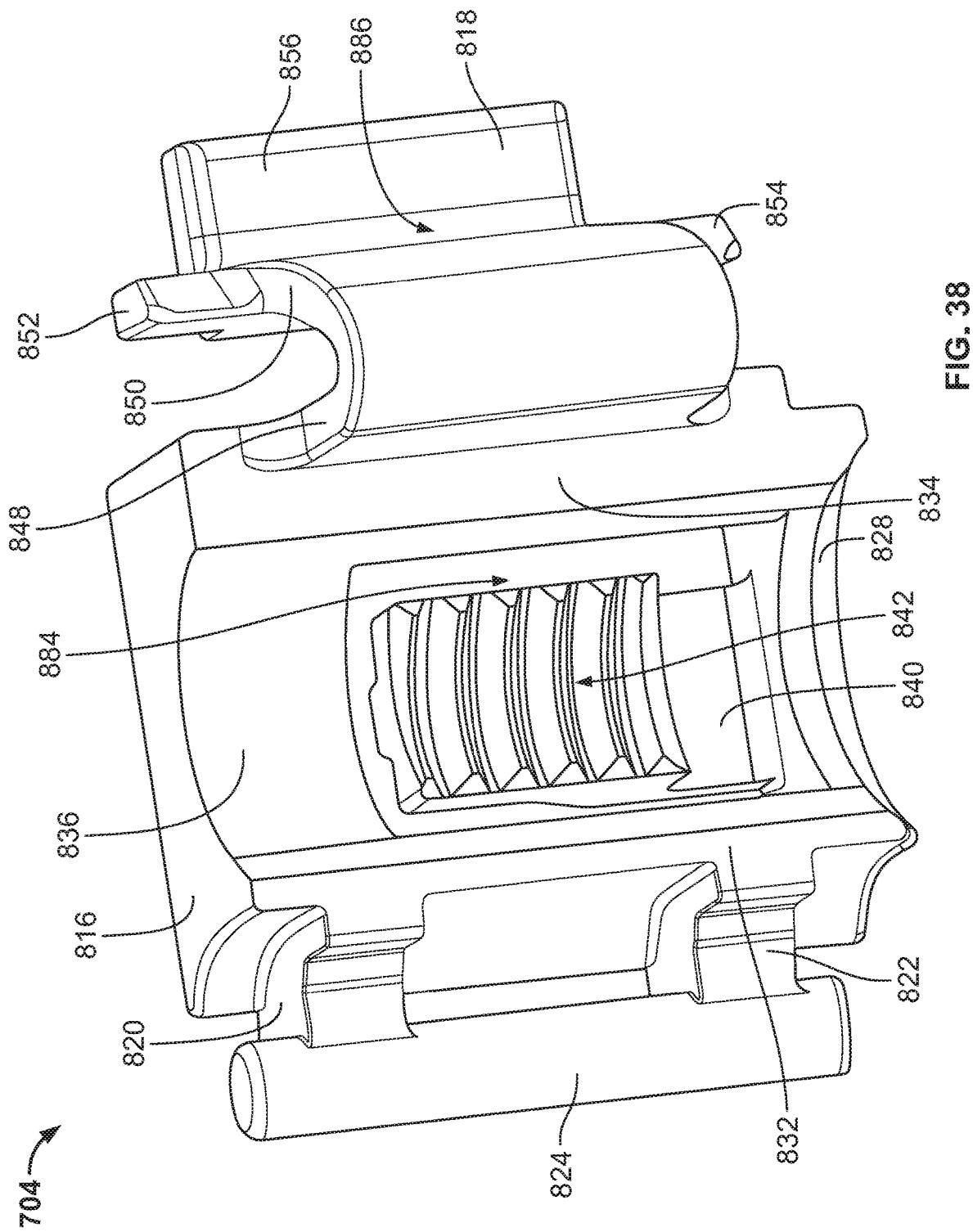
FIG. 38 is another isometric view of the clamp of FIG. 37.

With reference to FIG. 38, the clamp 704 includes a second stud receiver 816, a latch clip 818, an upper hinge arm 820, a lower hinge arm 822, and a hinge post 824. The latch clip 818, the upper hinge arm 820, and the lower hinge arm 822, are connected to and extend from the second stud receiver 816. The second stud receiver 816 is between the latch clip 818 and the upper hinge arm 820. The second stud receiver 816 is between the latch clip 818 and the lower hinge arm 822. The hinge post 824 is connected to and extends from the upper hinge arm 820 and the lower hinge arm 822.

With reference to FIG. 38, the second stud receiver 816 includes a third lower wall 828, a seventh side wall 832, an eighth side wall 834, a sixth rear wall 836, and a second resilient arm 840. The second resilient arm 840 includes a second set of teeth 842. The third lower wall 828 is connected to and between the seventh side wall 832 and the eighth side wall 834. The sixth rear wall 836 is connected to and between seventh side wall 832 and the eighth side wall 834. In some embodiments, the sixth rear wall 836 is curved. The upper hinge arm 820 and the lower hinge arm 822 are connected to and extends from the seventh side wall 832.

With reference to FIG. 38, the latch clip 818 includes a first resilient wall 848, a second resilient wall 850, an upper catch 852, a lower catch 854, and a release wall 856. The first resilient wall 848 is connected to the eighth side wall 834. The second resilient wall 850 is connected to the first resilient wall 848, the upper catch 852, the lower catch 854, and the release wall 856. The first resilient wall 848 and the second resilient wall 850 are transitionally connected to one another to form a rounded V shape, as shown in FIG. 39. With reference to FIG. 38, the upper catch 852 is opposite the lower catch 854. The release wall 856 is between the upper catch 852 and the lower catch 854. The upper catch 852 and the lower catch 854 are generally triangular. In other words, the upper catch 852 and the lower catch 854 are sloped relative to the second resilient wall 850 on one side.

With reference to FIG. 38, the hinge post 824 is generally cylindrical and extends parallel to the seventh side wall 832. The hinge post 824 extends beyond the upper hinge arm 820 and the lower hinge arm 822.

With reference to FIG. 35, the hinge tongue 736 includes a hinge wall 860 and a catch bulb 862. The catch bulb 862 is connected to and extends from the hinge wall 860. The hinge wall 860 is connected to and extends from the third side wall 748.

With reference to FIG. 38, the second stud receiver 816 defines a second stud pocket 884. More specifically, the third lower wall 828, the seventh side wall 832, the eighth side wall 834, the sixth rear wall 836, and the second resilient arm 840 define the second stud pocket 884. With reference to FIG. 34, when the clamp 704 is latched into the body 702 to place the first example fastener 700 in the closed state 712, the first stud pocket 800 and second stud pocket 884 are joined to form the stud cavity 718. Additionally, when the first example fastener 700 is in the closed state 712, the first set of teeth 762 is opposite the second set of teeth 842. In other words, when the first example fastener 700 is in the closed state 712, the first set of teeth 762 and the second set of teeth 842 face one another.

With reference to FIG. 38, the latch clip 818 defines a tool pocket 886. More specifically, the second resilient wall 850 and the release wall 856 define the tool pocket 886.

With reference to FIG. 39, the clamp 704 is pivotably engaged with the body 702. More specifically, the hinge post 824 is snapably inserted into the hinge pocket 804 to pivotably engage the hinge wall 860 and the catch bulb 862. Further, with reference to FIG. 32, the hinge post 824 is pivotably engaged with and stabilized by the second rear wall 752, the third rear wall 754, the first shoulder 756, and the second shoulder 758.

Figure 31:
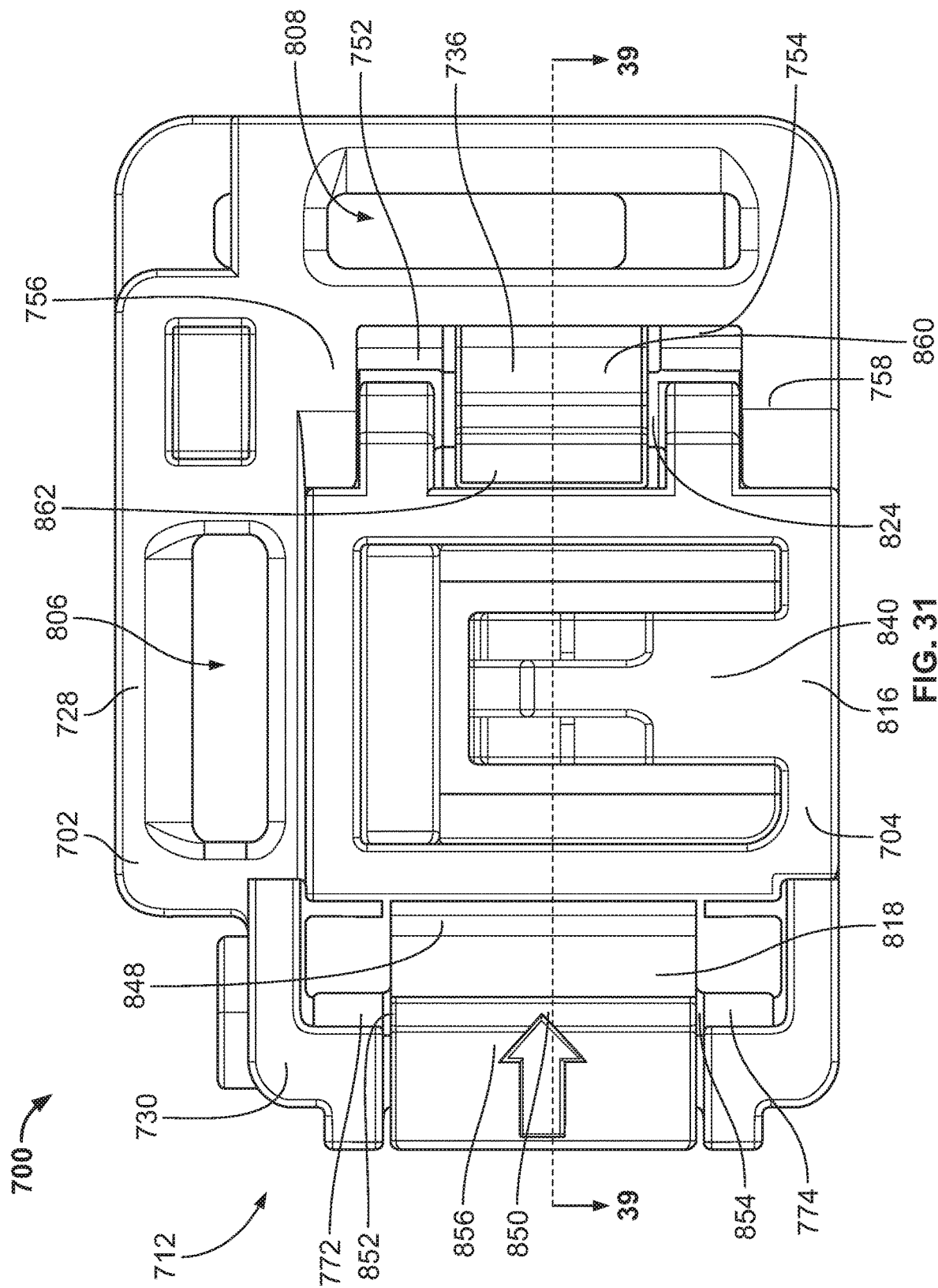
FIG. 31 is a front view of the sixth example fastener of FIGS. 29 and 31 in the closed state.

With reference to FIG. 31, in operation, when the clamp 704 is pivoted relative to the body 702 to place the first example fastener 700 in the closed state 712, the latch clip 818 is inserted into the latch receiver 730. As the latch clip 818 is pushed into the latch receiver 730, the upper catch 852 slides against the third shoulder 772 and the lower catch 854 slides against the fourth shoulder 774. Further, as the upper catch 852 slides against the third shoulder 772 and the lower catch 854 slides against the fourth shoulder 774, the second resilient wall 850 resiliently flexes toward the first resilient wall 848. Additionally, as the upper catch 852 slides against the third shoulder 772 and the lower catch 854 slides against the fourth shoulder 774, the first resilient wall 848 resiliently flexes toward the second stud receiver 816.

With reference to FIG. 31, in operation, as the latch clip 818 is pushed yet further into the latch receiver 730, the upper catch 852 slides past the third shoulder 772 and the lower catch 854 slides past the fourth shoulder 774. When the upper catch 852 slides past the third shoulder 772 and the lower catch 854 slides past the fourth shoulder 774, the first resilient wall 848 and the second resilient wall 850 resiliently snap away from the second stud receiver 816. When the first resilient wall 848 and the second resilient wall 850 resiliently snap away from the second stud receiver 816, upper catch 852 snapably engages the third shoulder 772. The lower catch 854 snapably engages the fourth shoulder 774 in the same manner as the upper catch 852 and the third shoulder 772. Thus, the latch clip 818 is snapably retained in the latch receiver 730 when the first example fastener 700 is in the closed state 712.

With reference to FIG. 39, the sixth example fastener 700 is configured to engage an externally threaded stud (not shown). In operation, the sixth example fastener 700 receives the stud via the stud cavity 718. When the stud is inserted into the stud cavity 718, the first set of teeth 762 and the second set of the teeth 842 ratchetingly engage the stud. More specifically, as the stud is pushed into the stud cavity 718, the first resilient arm 760 and the second resilient arm 840 flex away from one another and snappingly return toward one another as the stud ratchetingly slides along the first set of teeth 762 and the second set of teeth 842. With reference to FIG. 34, further in operation, the stud contacts the first upper wall 742. The first upper wall 742 provides a hard stop to the stud. Thus, the stud is not pushed through the sixth example fastener 700.

With reference to FIG. 39, further in operation, if a force is applied to remove the stud (not shown) from the sixth example fastener 700, the stud pulls against the first set of teeth 762 and the second set of teeth 842. When the stud pulls against the first set of teeth 762 and the second set of teeth 842, the first resilient arm 760 and the second resilient arm 840 are pulled toward one another. Thus, pulling the stud and the sixth example fastener 700 from one another tightens the first set of teeth 762 and the second set of teeth 842 against the stud. Thus, the sixth example fastener 700 is securely retained on the stud.

Figure 32:
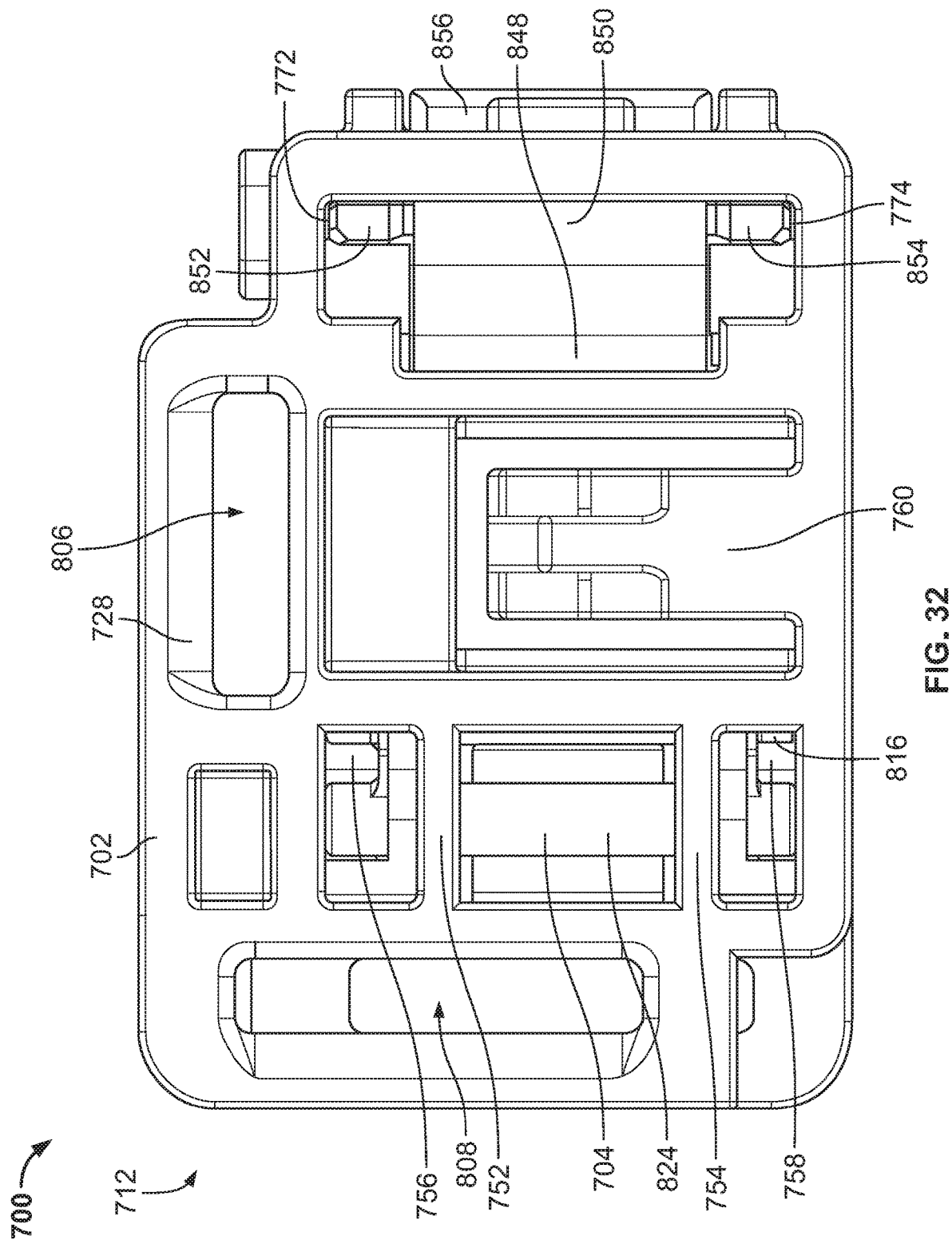
FIG. 32 is a rear view of the sixth example fastener of FIGS. 29-31 in the closed state.
Figure 33:
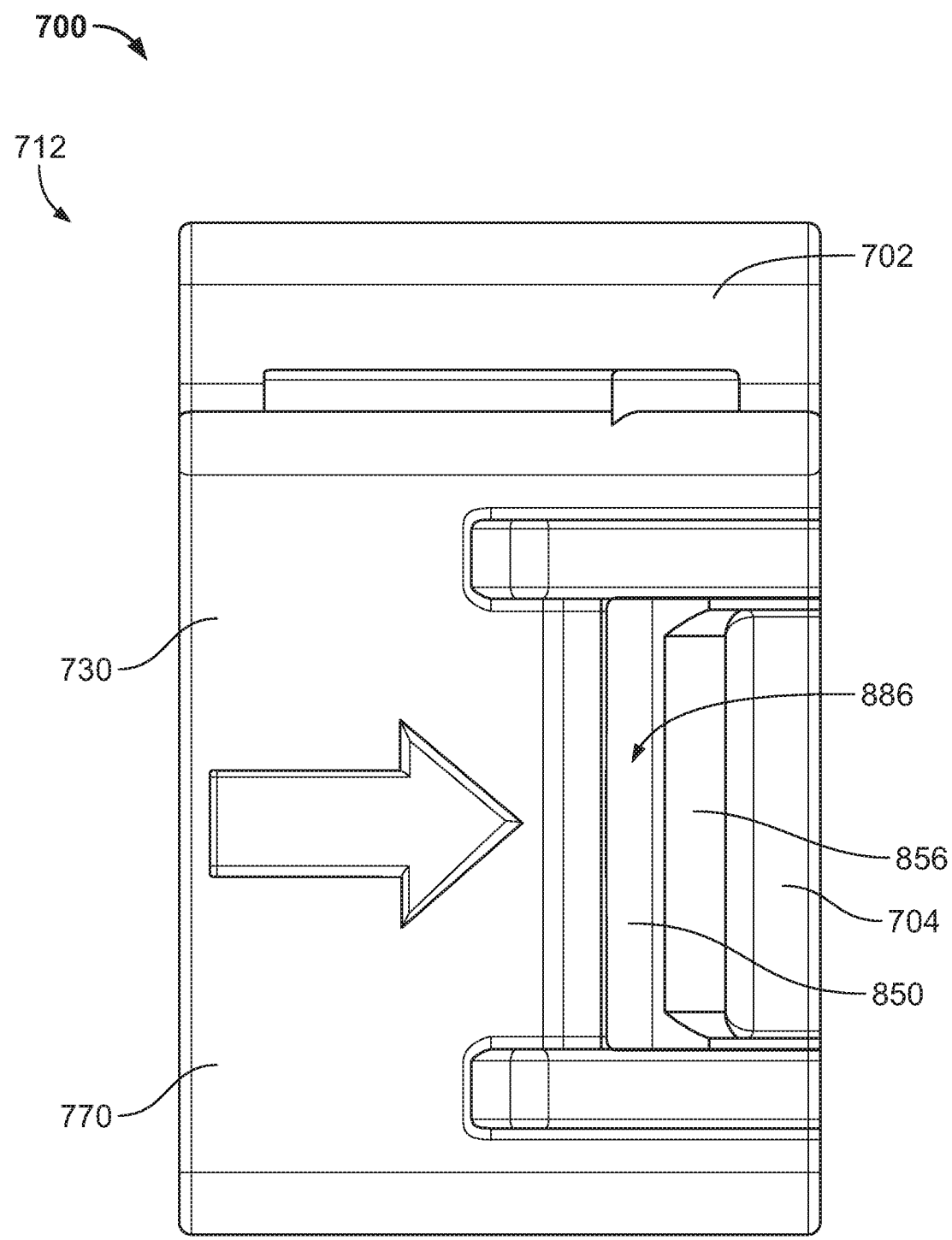
FIG. 33 is a side view of the sixth example fastener of FIGS. 29-32 in the closed state.

With reference to FIGS. 33 and 39, further in operation, a tool (e.g., a screwdriver) (not shown) may be inserted into the tool pocket 886 and pushed against the release wall 856 and the second resilient wall 850. With reference to FIG. 32, when the tool is pushed against the release wall 856 and the second resilient wall 850, the first resilient wall 848 and the second resilient wall 850 flex inwardly toward the first stud receiver 728 and the second stud receiver 816. With reference to FIG. 31, as the first resilient wall 848 and the second resilient wall 850 flex inwardly toward the first stud receiver 728 and the second stud receiver 816, the upper catch 852 is released from the third shoulder 772 and the lower catch 854 is released from the fourth shoulder 774. When the upper catch 852 is released from the third shoulder 772 and the lower catch 854 is released from the fourth shoulder 774, the clamp 704 is free to pivot away from the body 702. Thus, the clamp 704 releasably mates with the body 702. Further, with reference to FIG. 40, the stud may thus be freed from the body 702 and the clamp 704 and released from the sixth example fastener 700. Additionally or alternatively, a finger of an operator may also be inserted into the tool pocket 886 and pushed against the release wall 856 and the second resilient wall 850 in the same manner as the tool to release the clamp 704 from the body 702.

Figure 54:
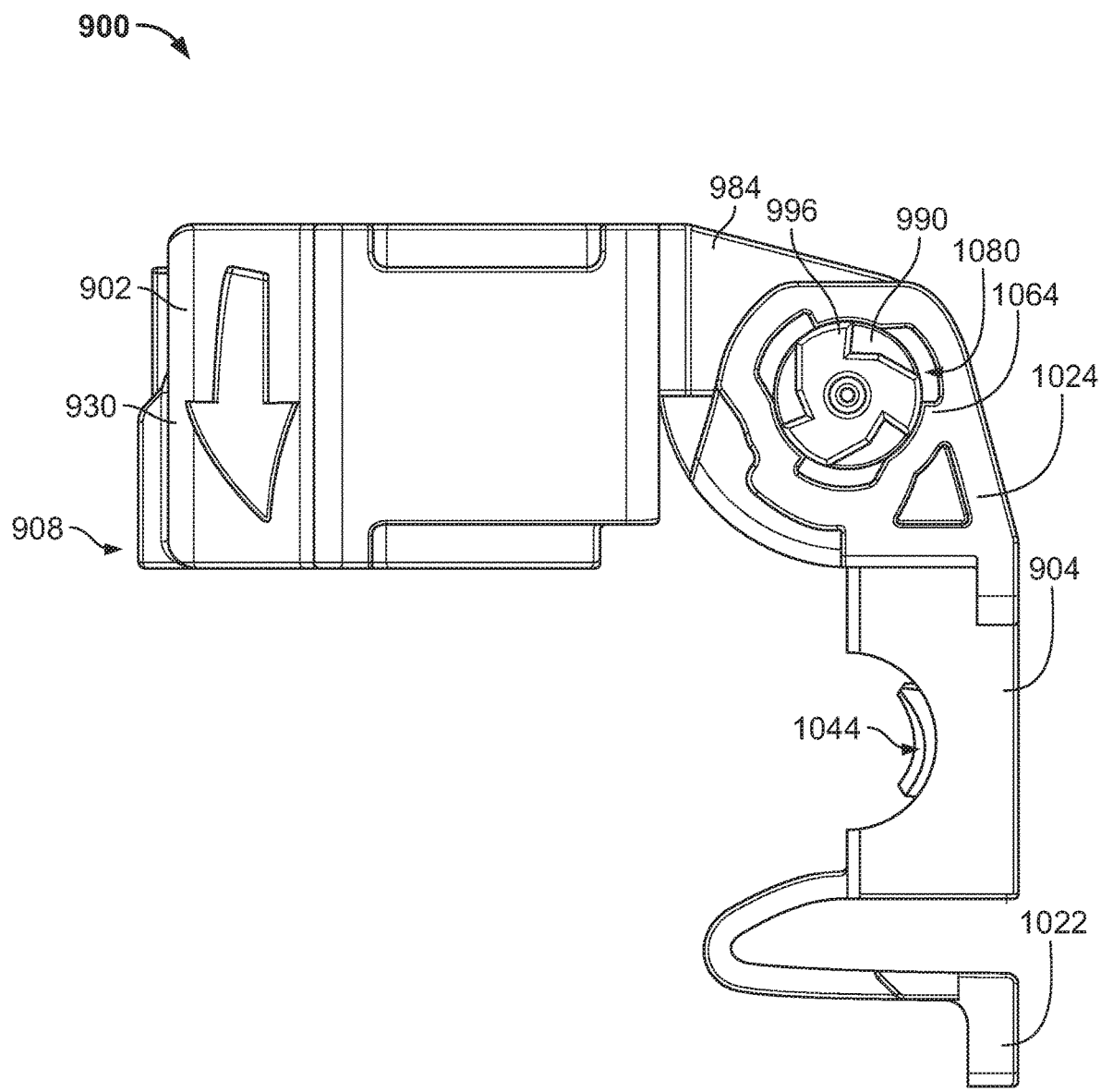
FIG. 54 is a top view of the seventh example fastener of FIGS. 41-49 in an intermediate state.
Figure 55:
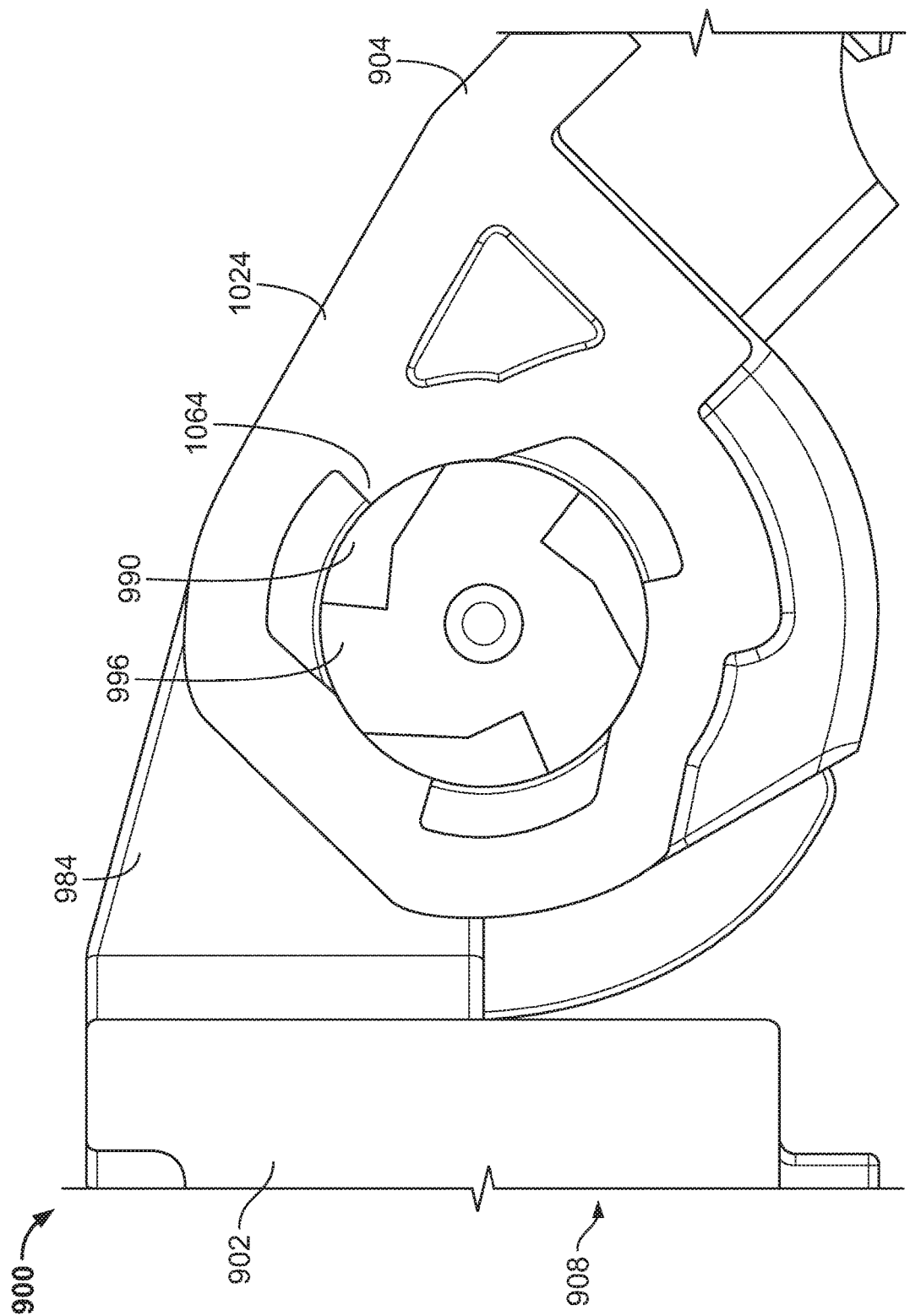
FIG. 55 is an enlarged partial top view of the seventh example fastener of FIGS. 41-49 and 54 in the intermediate state.

With reference to FIGS. 41-49 and 55-62, a seventh example fastener 900 includes a body 902 and a clamp 904. With reference to FIGS. 54 and 55, the seventh example fastener 900 is shown in an open state 908. With reference to FIGS. 57, 58, 61, and 62 the seventh example fastener 900 is shown in a released state 910. With reference to FIGS. 41, 42, 43, 56, 59, and 60 the seventh example fastener 900 is shown in a closed state 912. With reference to FIGS. 44-49, the seventh example fastener 900 is shown in an as-molded state 914.

Figure 56:
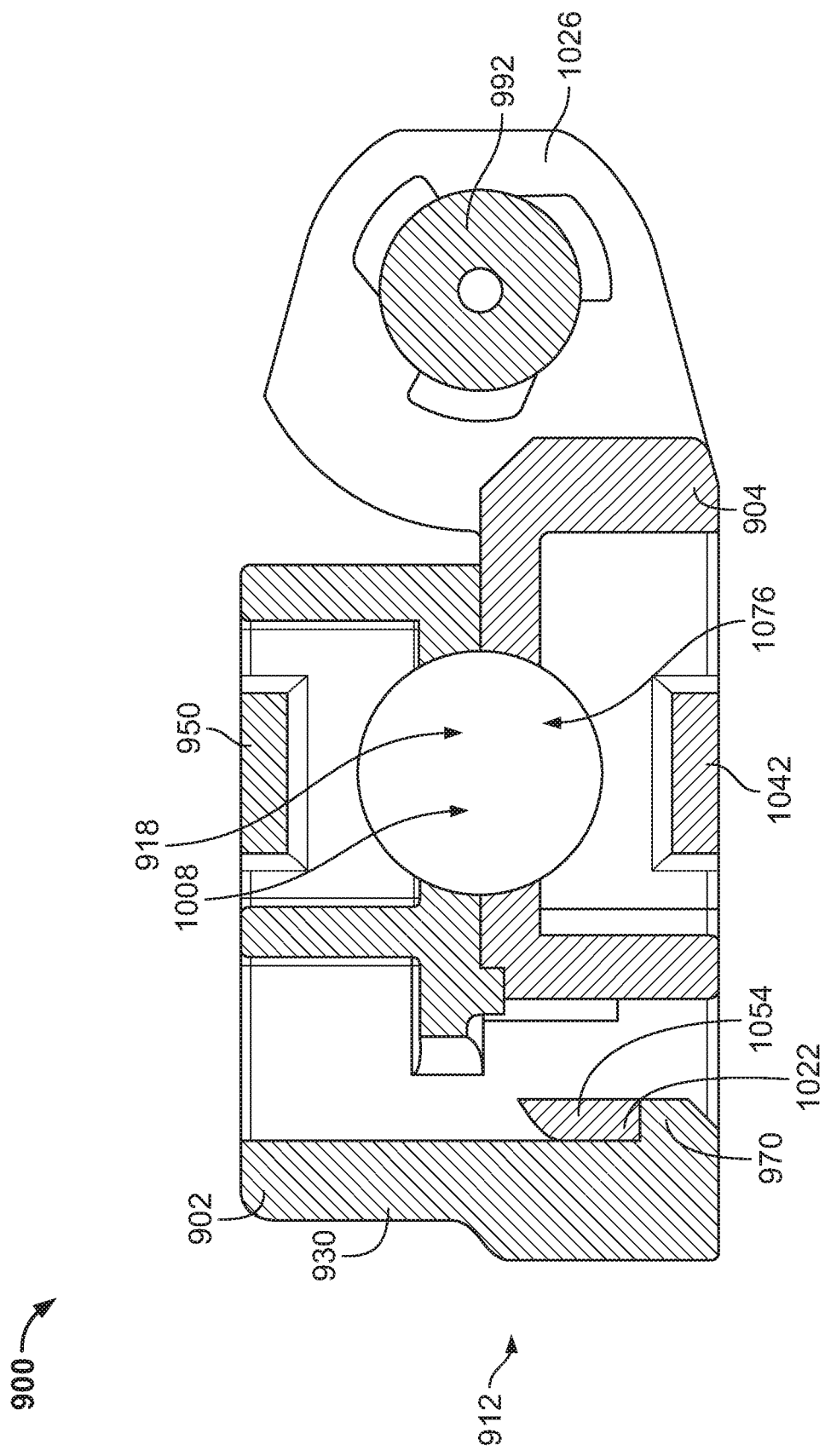
FIG. 56 a cross-sectional view of the seventh example fastener of FIGS. 41-49, 54, and 55 taken along line 56-56 of FIG. 43.

With reference to FIG. 54, the body 902 is pivotably connected to the clamp 904. With reference to FIG. 56, the clamp 904 selectively latchably secures in the body 902. When the seventh example fastener 900 is in the closed state 912 with the clamp 904 latched in the body 902, the body 902 and the clamp 904 define a stud cavity 918.

Figure 41:
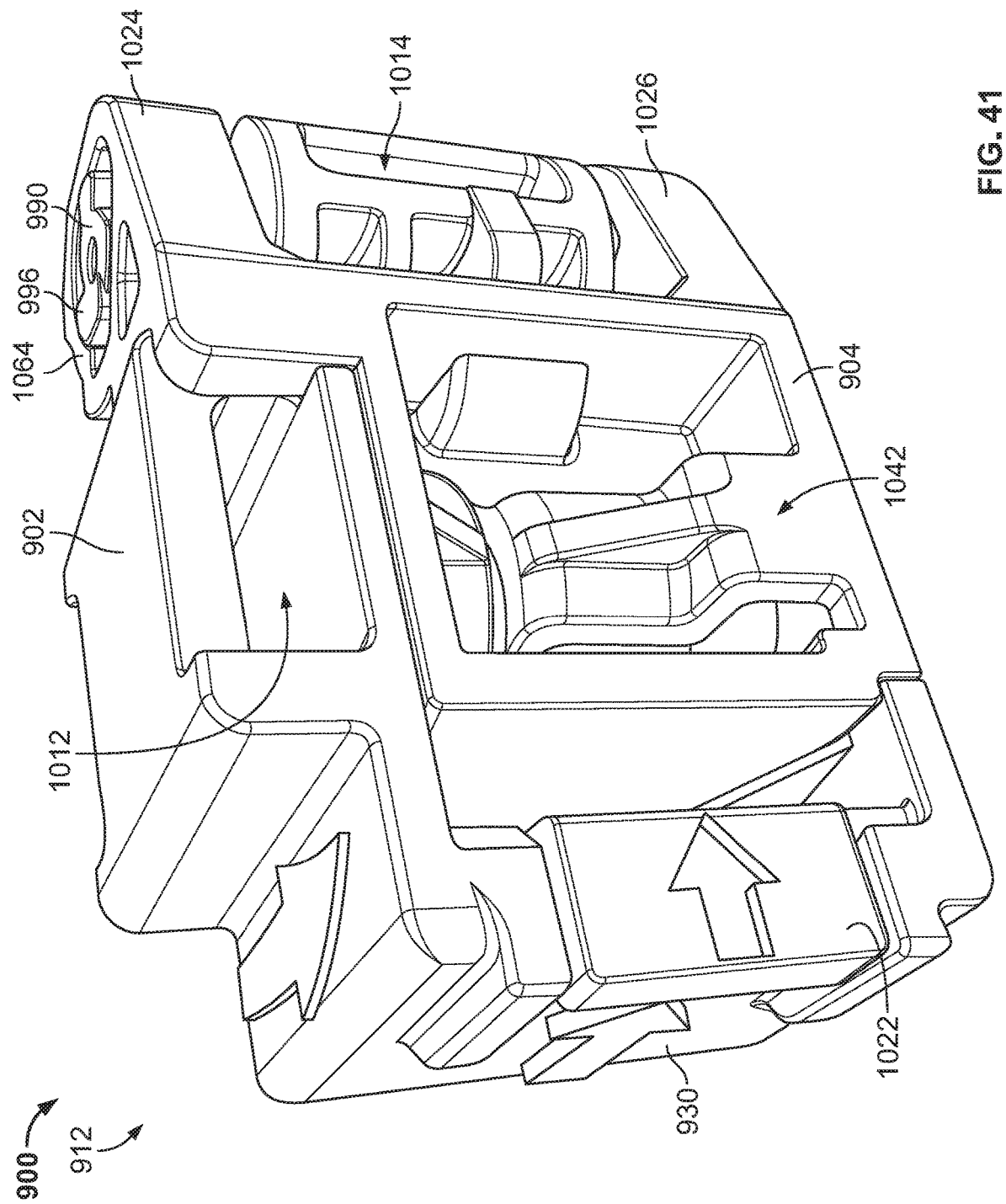
FIG. 41 is an isometric view of a seventh example fastener according to an embodiment of the present disclosure in a closed state.

With reference to FIG. 41, the seventh example fastener 900 may be made of a polymer plastic (e.g., polyamide (PA), polyoxymethylene (POM), Acrylonitrile butadiene styrene (ABS), etc.).

Figure 50:
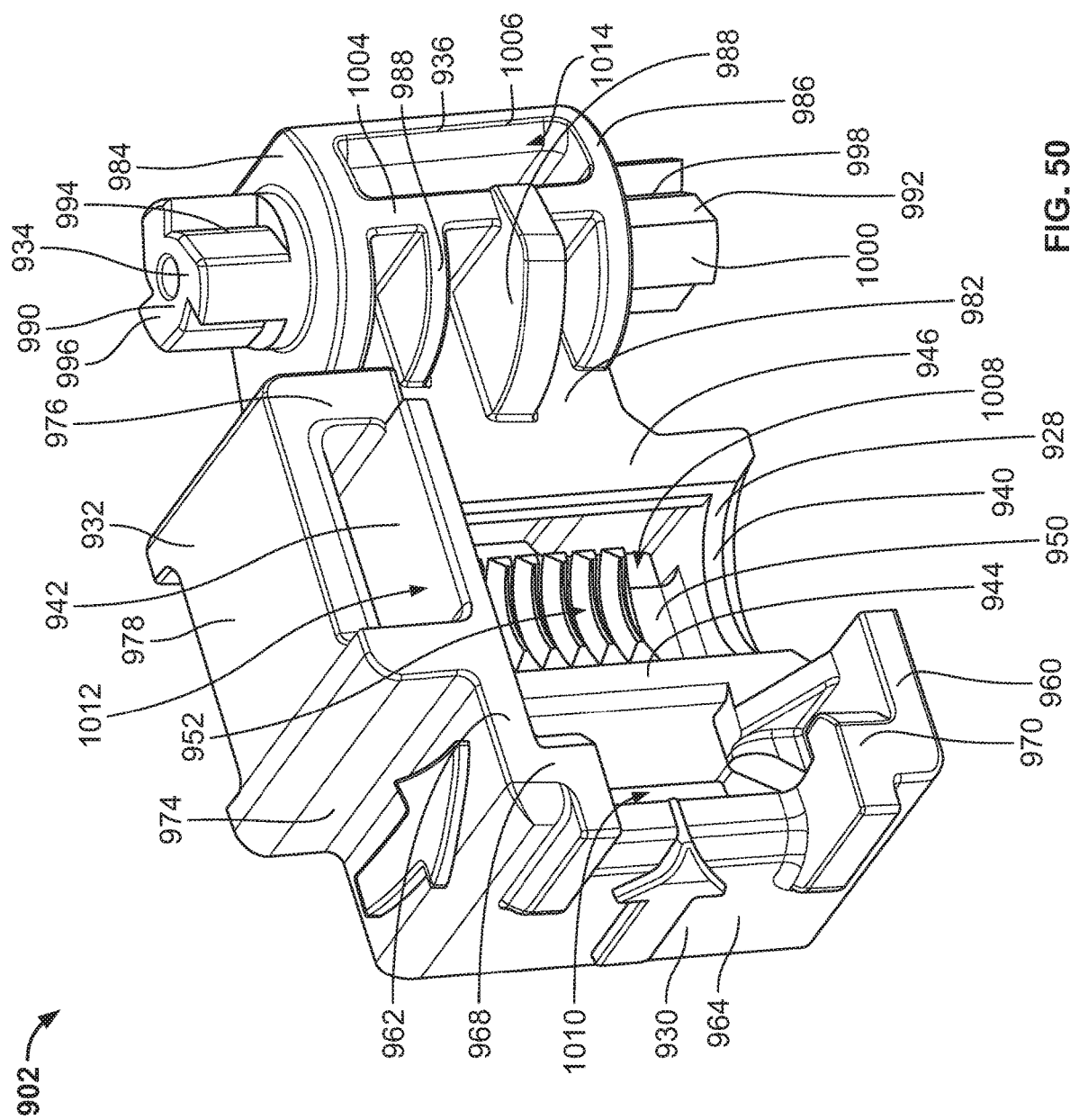
FIG. 50 is an isometric view of a body of the seventh example fastener of FIGS. 41-49.

With reference to FIG. 50, the body 902 includes a first stud receiver 928, a latch receiver 930, a first loop 932, a hinge post 934 and a second loop 936. The latch receiver 930, the first loop 932, and the hinge post 934 are connected to the first stud receiver 928. The second loop 936 is connected to the hinge post 934. The first stud receiver 928 is between the latch receiver 930 and the hinge post 934. The hinge post 934 is between the first stud receiver 928 and the second loop 936. The first loop 932 is connected to the first stud receiver between the latch receiver 930 and the hinge post 934.

Figure 51:
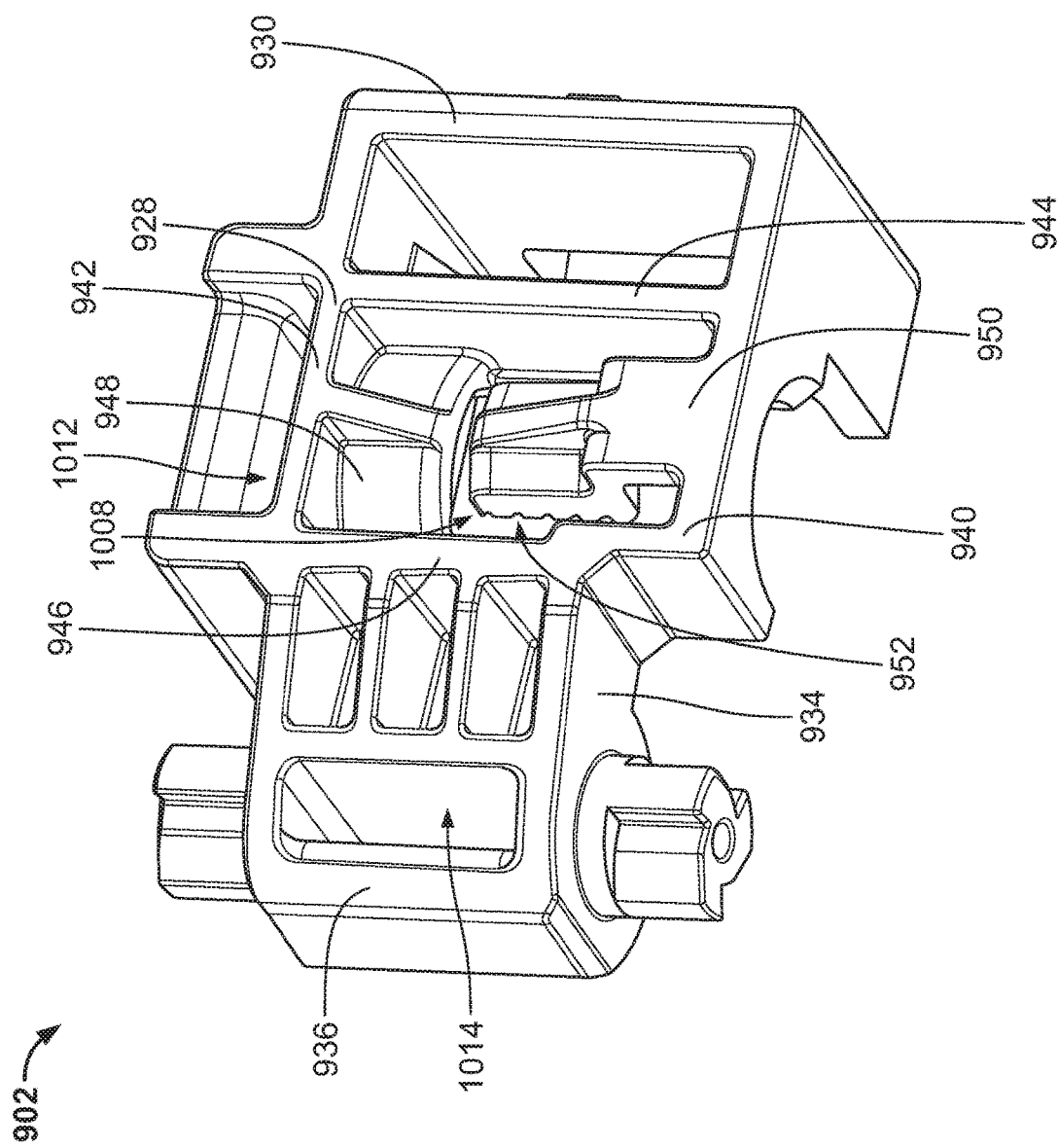
FIG. 51 is another isometric view of the body of FIG. 50.

With reference to FIG. 50, the first stud receiver 928 includes a first lower wall 940, a first upper wall 942, a first side wall 944, and a second side wall 946. With reference to FIG. 51, the first stud receiver 928 further includes a first rear wall 948. With reference to FIG. 50, the first stud receiver 928 further includes a first resilient arm 950. The first resilient arm 950 includes a first set of teeth 952. The first lower wall 940 is connected to the first side wall 944 and the second side wall 946. The first upper wall 942 is connected to the first side wall 944 and the second side wall 946. With reference to FIG. 51, the first rear wall 948 is connected to the first side wall 944, the second side wall 946, and the first upper wall 942. The first resilient arm 950 is connected to and extends from the first lower wall 940 toward the first upper wall 942. The first set of teeth 952 extend inwardly. In other words, the first set of teeth 952 extend away from the first rear wall 948.

With reference to FIG. 50, the latch receiver 930 includes a second lower wall 960, a second upper wall 962, a third side wall 964, an upper shoulder 968, and a lower shoulder 970. The second lower wall 960 is connected to and extends from the first lower wall 940. The second upper wall 962 is connected to and extends from the first upper wall 942. The third side wall 964 is connected to and between the second lower wall 960 and the second upper wall 962. The upper shoulder 968 is connected to and extends from the second upper wall 962 and the third side wall 964. The lower shoulder 970 is connected to and extends from the third side wall 964 and the second lower wall 960.

With reference to FIG. 50, the first loop 932 includes a fourth side wall 974, a fifth side wall 976, and a third upper wall 978. The third upper wall 978 is connected to and between the fourth side wall 974 and the fifth side wall 976. The fourth side wall 974 is connected to and extends from the first upper wall 942. The fifth side wall 976 is connected to and extends from the first upper wall 942.

With reference to FIG. 50, the hinge post 934 includes a hinge wall 982, a fourth upper wall 984, a third lower wall 986, a support ribs 988, an upper drum 990, and a lower drum 992. The upper drum 990 includes an upper pin 994 and upper barbs 996. The lower drum 992 includes a lower pin 998 and lower barbs 1000. The hinge post 934 further includes a sixth side wall 1004. The hinge wall 982 is connected to and extends from the second side wall 946. The fourth upper wall 984 is connected to and extends from the hinge wall 982. The third lower wall 986 is connected to and extends from the hinge wall 982. The support ribs 988 are connected to and extend from the hinge wall 982 and the sixth side wall 1004. The support ribs 988 are between the fourth upper wall 984 and the third lower wall 986.

With reference to FIG. 50, the second loop 936 includes a seventh side wall 1006. The seventh side wall 1006 is connected to and between the fourth upper wall 984 and the third lower wall 986.

With reference to FIG. 50, the upper drum 990 is connected to and extends from the fourth upper wall 984. More specifically, the upper pin 994 and the upper barbs 996 extend from the fourth upper wall 984. The upper barbs 996 extend radially from the upper pin 994. The lower drum 992 is connected to and extends from the third lower wall 986. The lower pin 998 and the lower barbs 1000 extend from the third lower wall 986. The lower barbs 1000 extend radially from the lower pin 998.

With reference to FIG. 50, the first stud receiver 928 defines a first stud pocket 1008. More specifically, the first lower wall 940, the first upper wall 942, the first side wall 944, and the second side wall 946 define the first stud pocket 1008. With reference to FIG. 51, the first rear wall 948 further defines the first stud pocket 1008.

With reference to FIG. 50, the latch receiver 930 defines a latch pocket 1010. More specifically, the second lower wall 960, the second upper wall 962, the third side wall 964, the upper shoulder 968, and the lower shoulder 970 define the latch pocket 1010.

With reference to FIG. 50, the first loop 932 defines a first strap passage 1012. More specifically, the fourth side wall 974, the fifth side wall 976, and the third upper wall 978 define the first strap passage 1012. The first upper wall 942 further defines the first strap passage 1012.

With reference to FIG. 50, the second loop 936 defines a second strap passage 1014. More specifically, the seventh side wall 1006 defines the second strap passage 1014. The fourth upper wall 984, the third lower wall 986, and the sixth side wall 1004 further define the second strap passage 1014.

Figure 53:
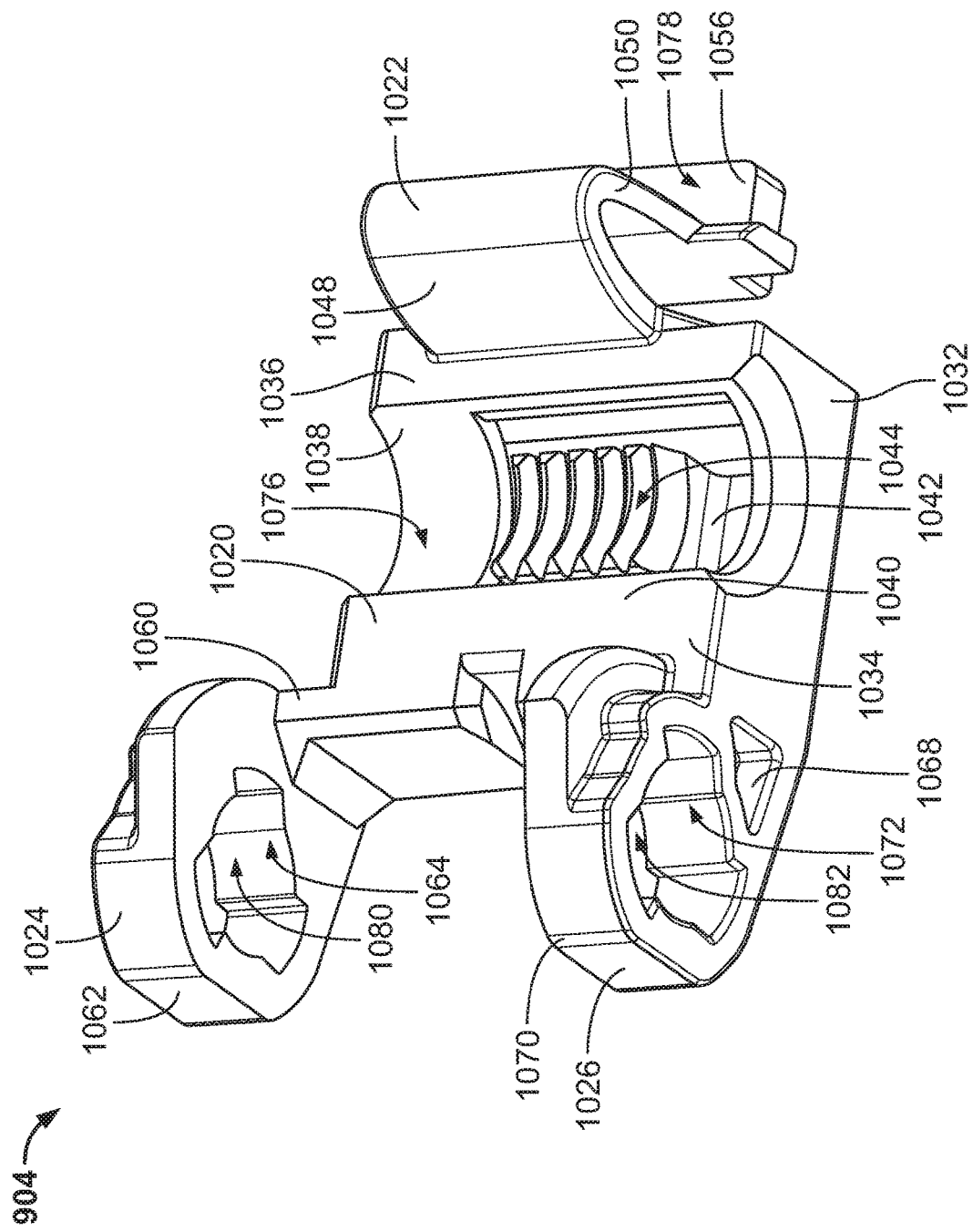
FIG. 53 is another isometric view of the clamp of FIG. 52.

With reference to FIG. 53, the clamp 904 includes a second stud receiver 1020, a latch clip 1022, an upper hinge receiver 1024, and a lower hinge receiver 1026. The latch clip 1022, the upper hinge receiver 1024, and the lower hinge receiver 1026 are connected to and extend from the second stud receiver 1020. The second stud receiver 1020 is between the latch clip 1022 and the upper hinge receiver 1024. The second stud receiver 1020 is between the latch clip 1022 and the lower hinge receiver 1026.

With reference to FIG. 53, the second stud receiver 1020 includes a fourth lower wall 1032, an eighth side wall 1034, a ninth side wall 1036, a third rear wall 1038, a front wall 1040, and a second resilient arm 1042. The second resilient arm 1042 includes a second set of teeth 1044. The fourth lower wall 1032 is connected to and between the eighth side wall 1034 and the ninth side wall 1036. The third rear wall 1038 is connected to and between eighth side wall 1034 and the ninth side wall 1036. In some embodiments, the third rear wall 1038 is curved. The front wall 1040 is connected to and extends from the eighth side wall 1034, the fourth lower wall 1032, and the third rear wall 1038. The upper hinge receiver 1024 and the lower hinge receiver 1026 are connected to and extend from the eighth side wall 1034.

Figure 52:
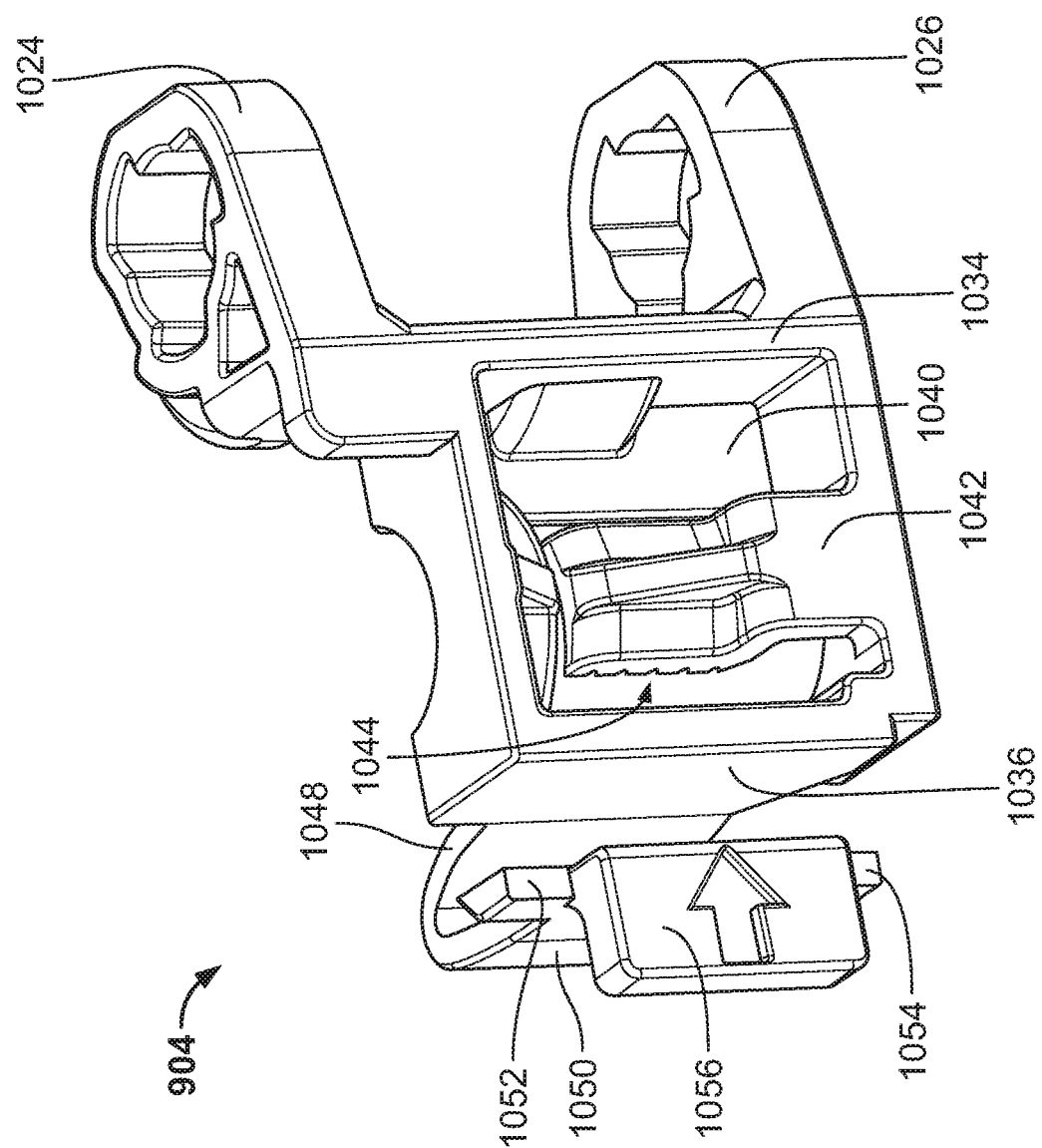
FIG. 52 is an isometric view of a clamp of the seventh example fastener of FIGS. 41-49.

With reference to FIG. 52, the latch clip 1022 includes a first resilient wall 1048, a second resilient wall 1050, an upper catch 1052, a lower catch 1054, and a release wall 1056. The first resilient wall 1048 is connected to the ninth side wall 1036. The second resilient wall 1050 is connected to the first resilient wall 1048, the upper catch 1052, the lower catch 1054, and the release wall 1056. The first resilient wall 1048 and the second resilient wall 1050 are transitionally connected to one another to form a rounded V shape. With reference to FIG. 52, the upper catch 1052 is opposite the lower catch 1054. The release wall 1056 is between the upper catch 1052 and the lower catch 1054. The upper catch 1052 and the lower catch 1054 are generally triangular. In other words, the upper catch 1052 and the lower catch 1054 are sloped relative to the second resilient wall 1050 on one side.

With reference to FIG. 53, the upper hinge receiver 1024, includes an upper hinge arm 1060, an upper annular wall 1062, and an upper set of pawls 1064. The upper hinge arm 1060 is connected to the eighth side wall 1034 and the upper annular wall 1062. The upper set of pawls 1064 extend radially inwardly from the upper annular wall 1062.

With reference to FIG. 53, the lower hinge receiver 1026 includes a lower hinge arm 1068, a lower annular wall 1070, and a lower set of pawls 1072. The lower hinge arm 1068 is connected to the eighth side wall 1034 and the lower annular wall 1070. The lower set of pawls 1072 extend radially inwardly from the lower annular wall 1070.

Figure 42:
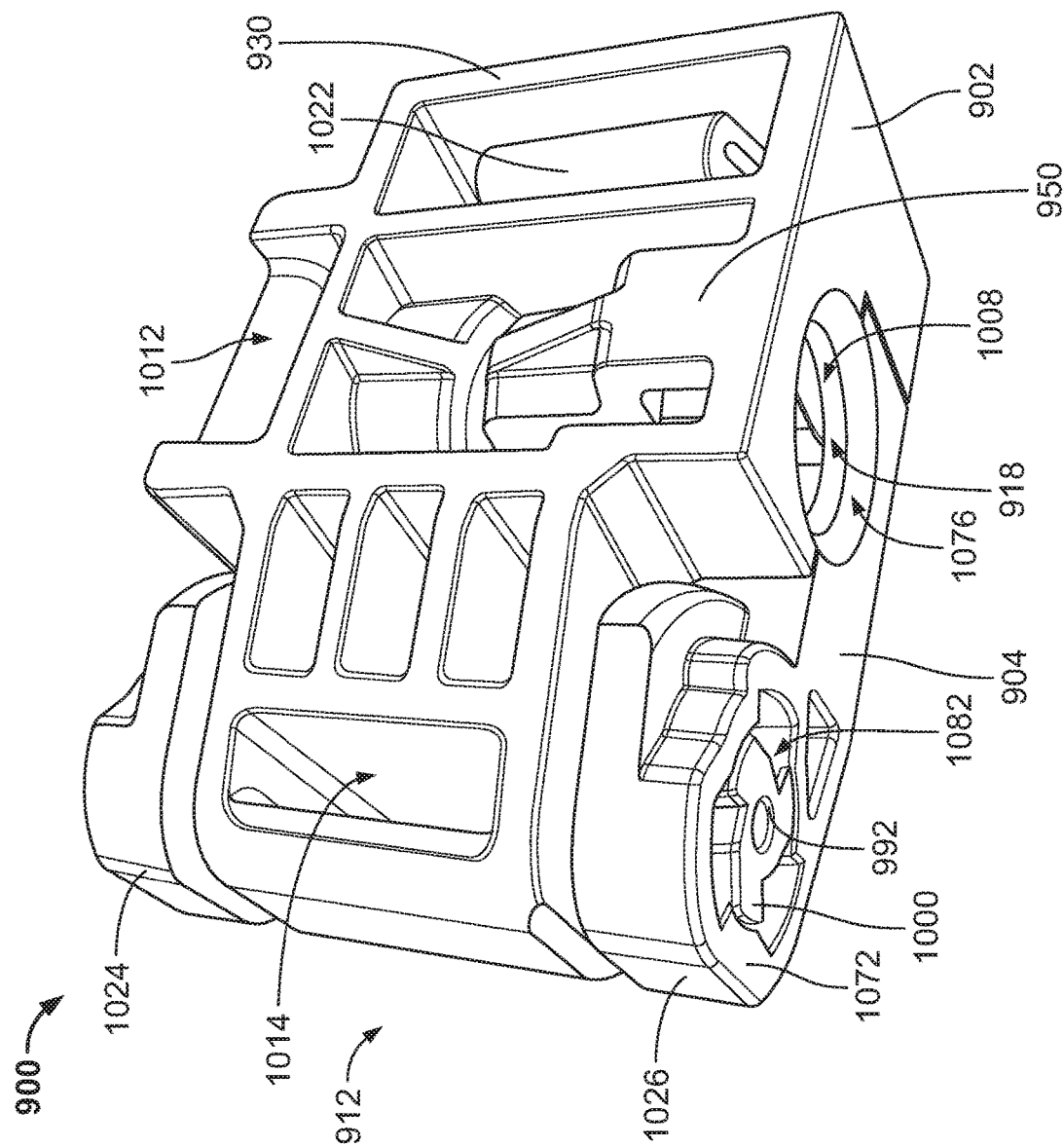
FIG. 42 is another isometric view of the seventh example fastener of FIG. 41 in the closed state.

With reference to FIG. 53, the second stud receiver 1020 defines a second stud pocket 1076. More specifically, the fourth lower wall 1032, the eighth side wall 1034, the ninth side wall 1036, the third rear wall 1038, and the front wall 1040 define the second stud pocket 1076. With reference to FIG. 42, when the clamp 904 is latched into the body 902 to place the first example fastener 900 in the closed state 912, the first stud pocket 1008 and second stud pocket 1076 are joined to form the stud cavity 918. Additionally, with reference to FIG. 56, when the first example fastener 900 is in the closed state 912, the first resilient arm 950 is opposite the second resilient arm 1042. In other words, when the first example fastener 900 is in the closed state 912, the first resilient arm 950 and the second resilient arm 1042 face one another.

With reference to FIG. 53, the latch clip 1022 defines a tool pocket 1078. More specifically, the second resilient wall 1050 and the release wall 1056 define the tool pocket 1078.

With reference to FIG. 53, the upper hinge receiver 1024 defines an upper hinge opening 1080. More specifically, the upper annular wall 1062 and the upper set of pawls 1064 define the upper hinge opening 1080.

With reference to FIG. 53, the lower hinge receiver 1026 defines a lower hinge opening 1082. More specifically, the lower annular wall 1070 and the lower set of pawls 1072 define the lower hinge opening 1082.

With reference to FIGS. 54 and 55, the clamp 904 is pivotably engaged with the body 902. More specifically, the upper drum 990 is pivotably disposed in the upper hinge receiver 1024 via the upper hinge opening 1080. The upper barbs 996 are slidably and rotatably engaged with the upper set of pawls 1064. When the seventh example fastener 900 is in the open state 908, the upper drum 990 is centered in the upper hinge opening 1080 of the upper hinge receiver 1024. In other words, when the seventh example fastener 900 moves from the open state 908 (shown in FIG. 54) to the closed state 912 (shown in FIG. 41), the upper hinge receiver 1024 tends to move into concentricity with the upper drum 990 via the upper barbs 996 and the upper set of pawls 1064, which facilitates closing the clamp 904 into the body 902. With reference to FIG. 42, the lower drum 992 is pivotably disposed in the lower hinge receiver 1026 via the lower hinge opening 1082. The lower barbs 1000 are slidably and rotatably engaged with the lower set of pawls 1072. When the seventh example fastener 900 is in the closed state 912, the lower drum 992 is centered in the lower hinge opening 1082 of the lower hinge receiver 1026. Additionally, when the seventh example fastener 900 is in the open state 908, the lower drum 992 is centered in the lower hinge opening 1082 of the lower hinge receiver 1026 (not shown). In other words, when the seventh example fastener 900 moves from the open state 908 (shown in FIG. 54) to the closed state 912 (shown in FIG. 42), the lower hinge receiver 1026 tends to move into concentricity with the lower drum 992 via the lower barbs 1000 and the lower set of pawls 1072, which further facilitates closing the clamp 904 into the body 902.

Figure 44:
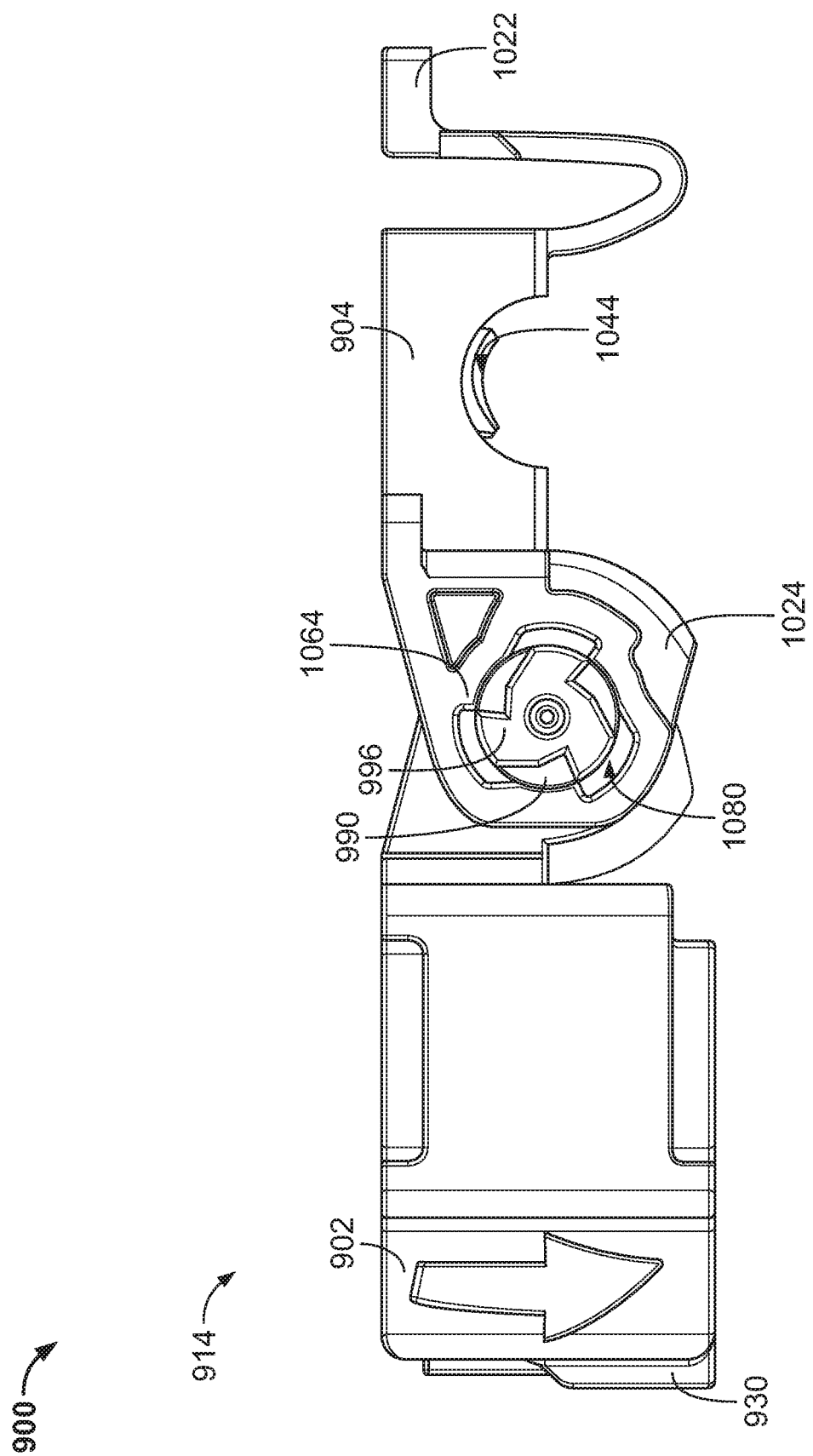
FIG. 44 is a top view of the seventh example fastener of FIGS. 41, 42, and 43 in an open state.
Figure 45:
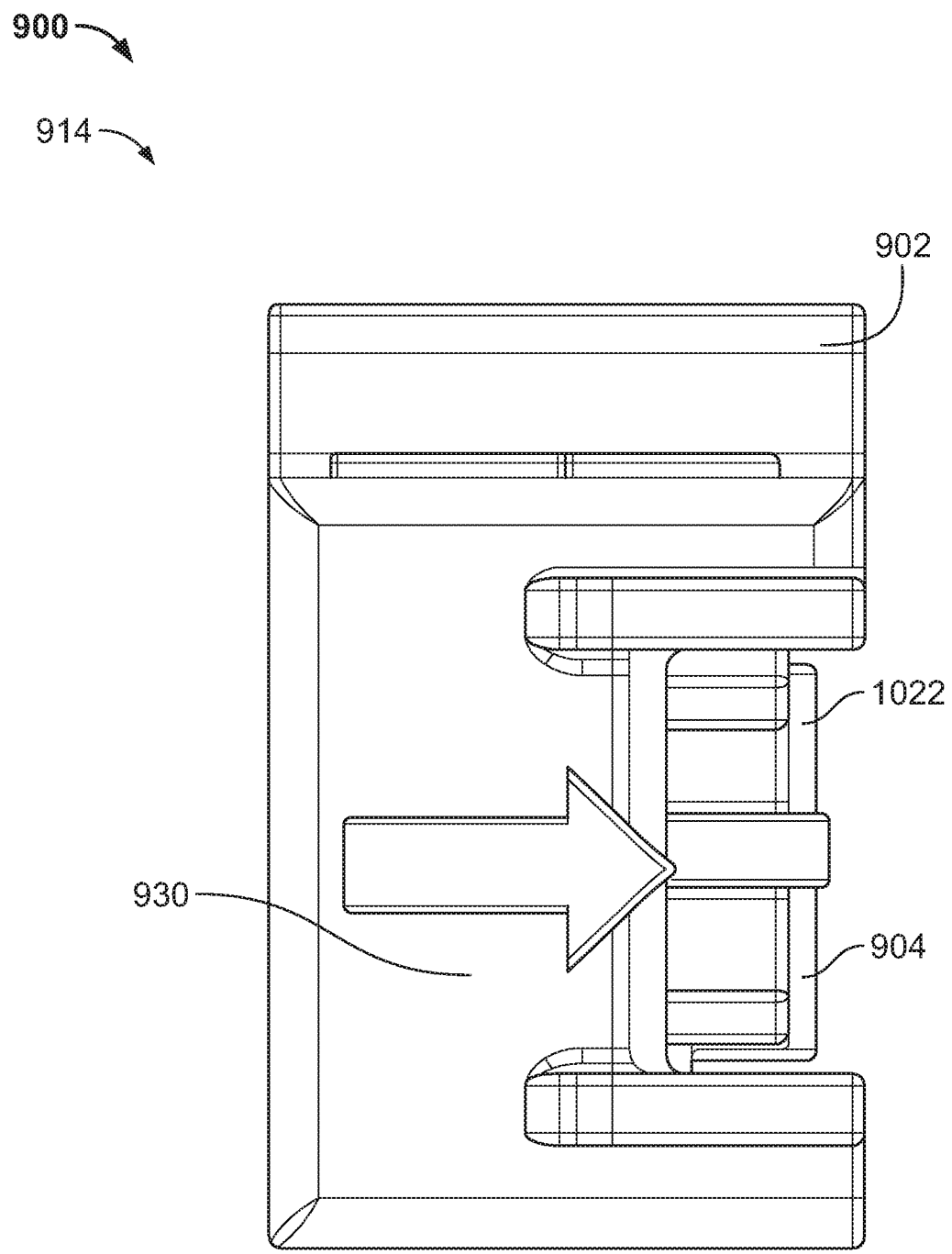
FIG. 45 is a side view of the seventh example fastener of FIGS. 41-44 in the open state.
Figure 46:
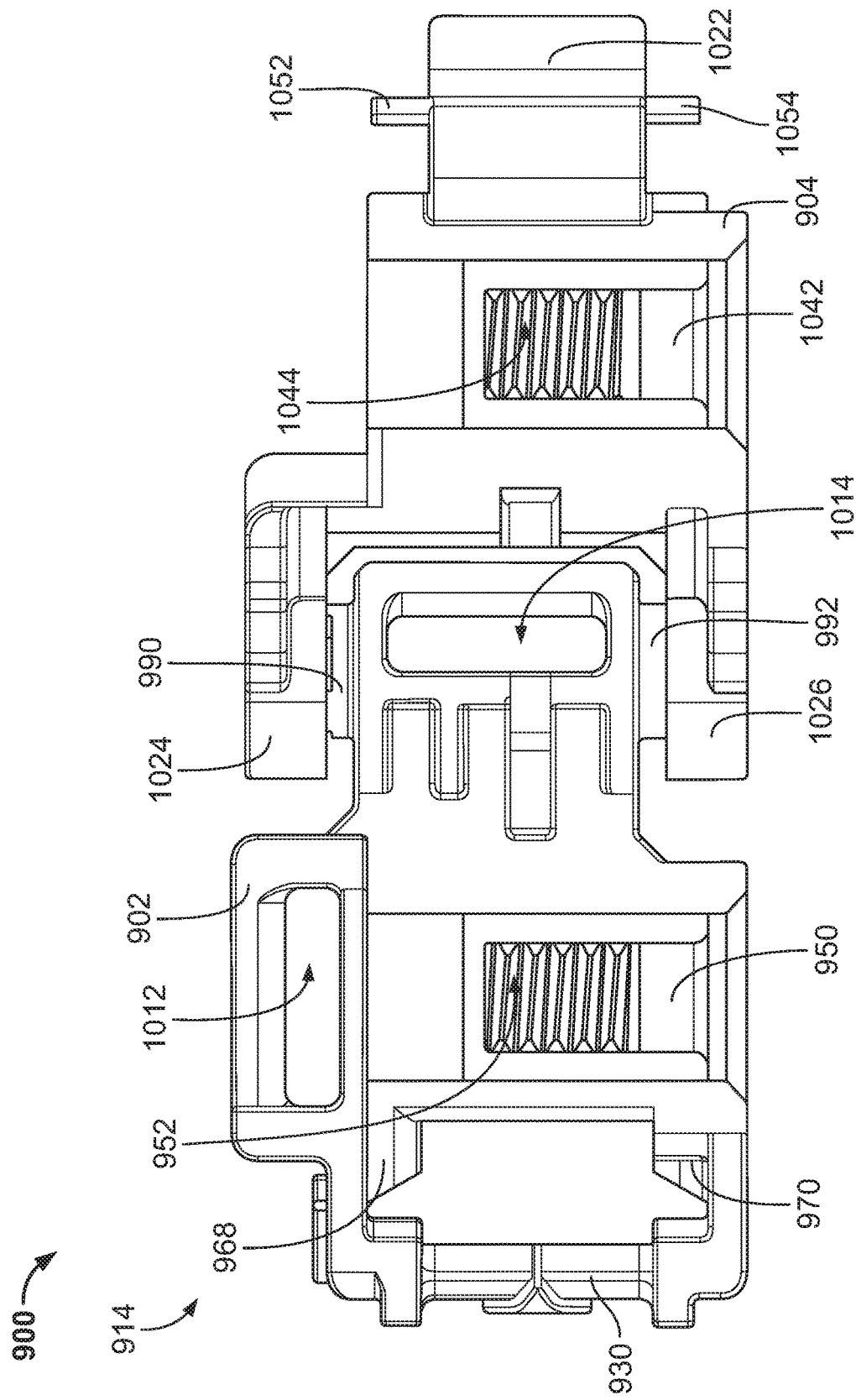
FIG. 46 is a front view of the seventh example fastener of FIGS. 41-45 in the open state.
Figure 47:
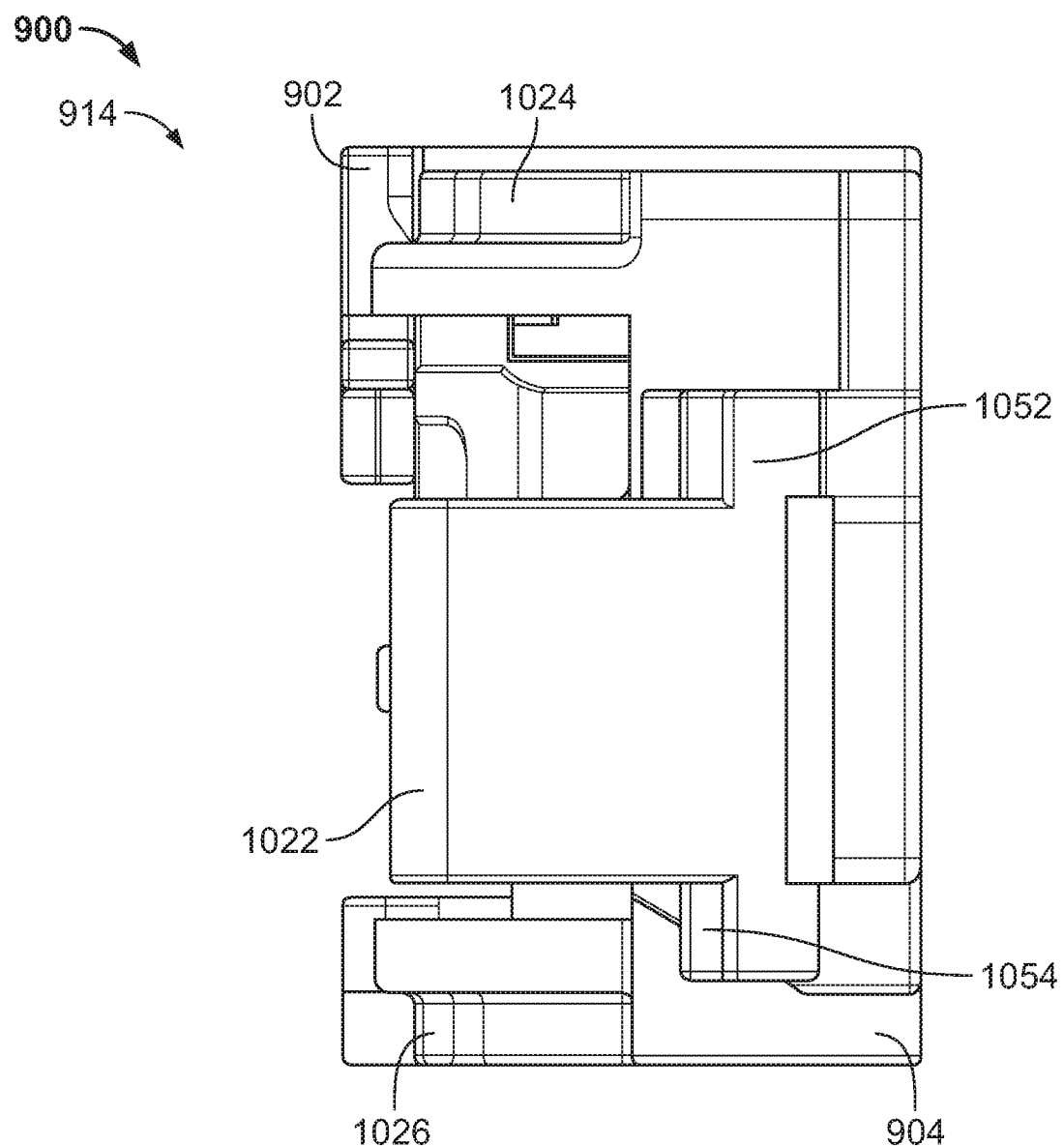
FIG. 47 is another side view of the seventh example fastener of FIGS. 41-46 in the open state.
Figure 48:
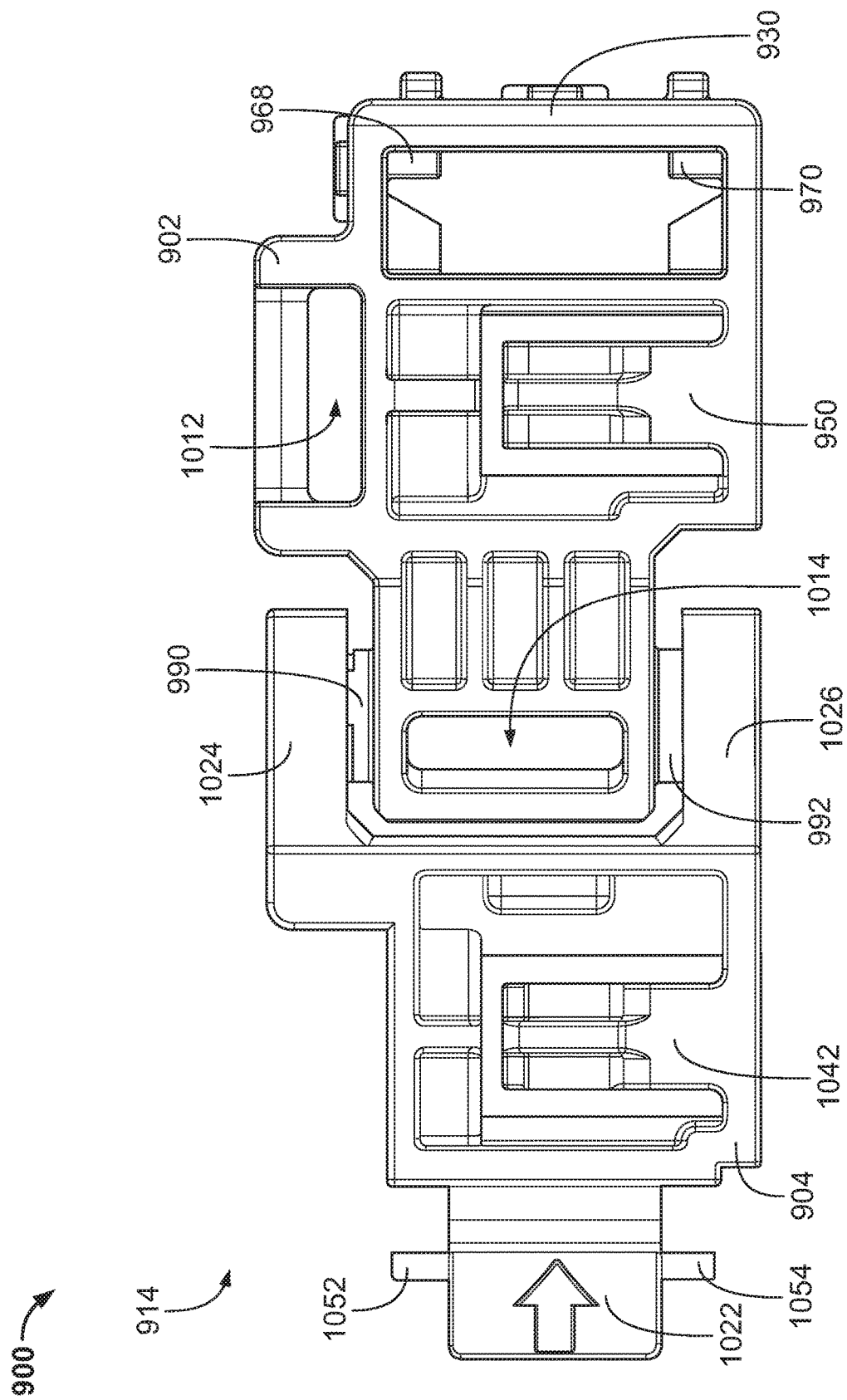
FIG. 48 is a rear view of the seventh example fastener of FIGS. 41-47 in the open state.
Figure 49:
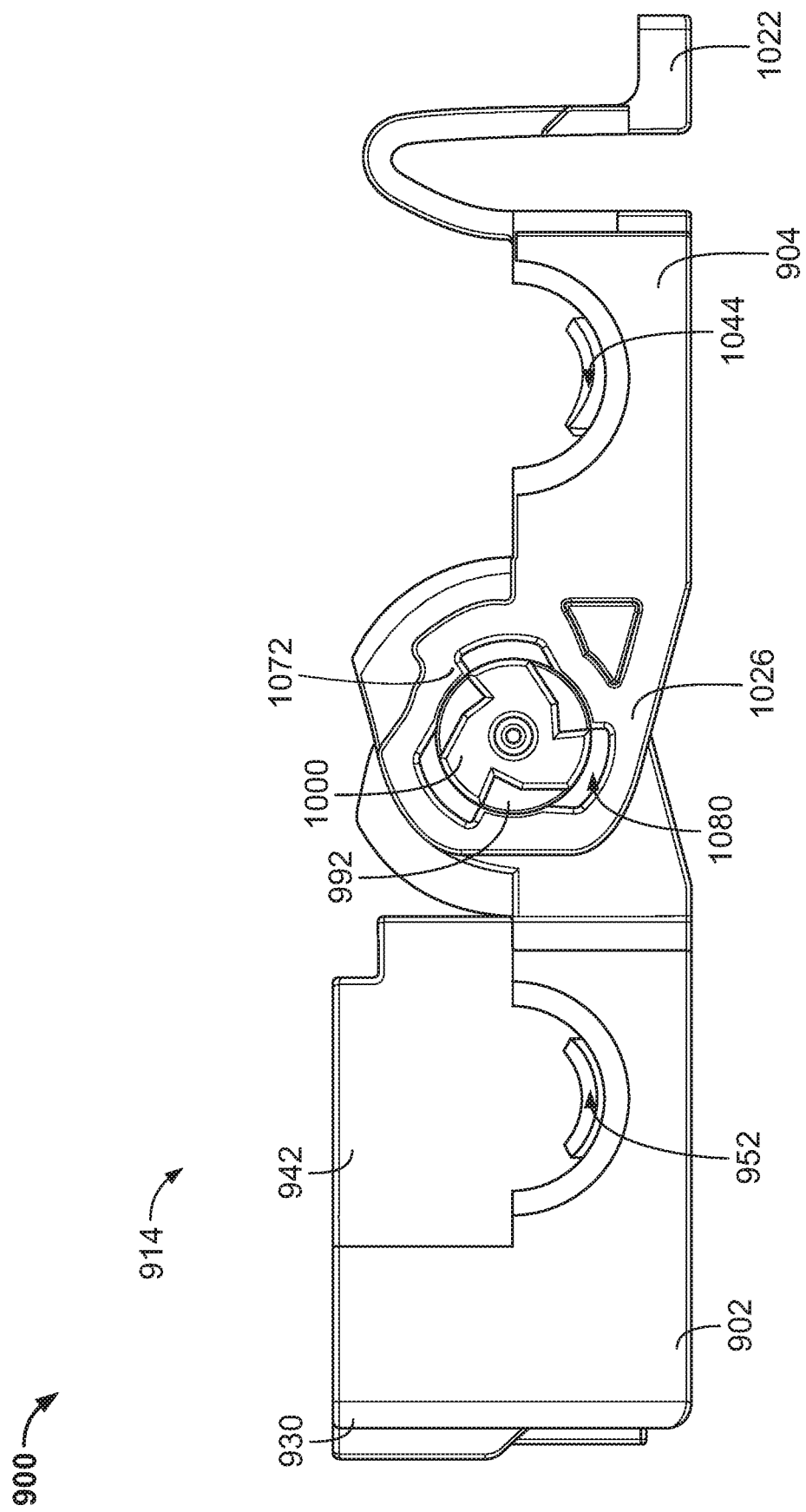
FIG. 49 is a bottom view of the seventh example fastener of FIGS. 41-48 in the open state.

With reference to FIG. 44, when the seventh example fastener 900 is in the as-molded state 914, the upper barbs 996 are connected to the upper set of pawls 1064. With reference to FIG. 49, when the seventh example fastener 900 is in the as-molded state 914, the lower barbs 1000 are connected to the lower set of pawls 1072.

With reference to FIG. 44, in operation, when the clamp 904 is pivoted relative to the body 902 in the as-molded state 914, the upper barbs 996 are disconnected from (e.g. broken away from) the upper set of pawls 1064. With reference to FIG. 49, when the clamp 904 is pivoted relative to the body 902 in the as-molded state 914, the lower barbs 1000 are disconnected from (e.g. broken away from) the lower set of pawls 1072.

Figure 43:
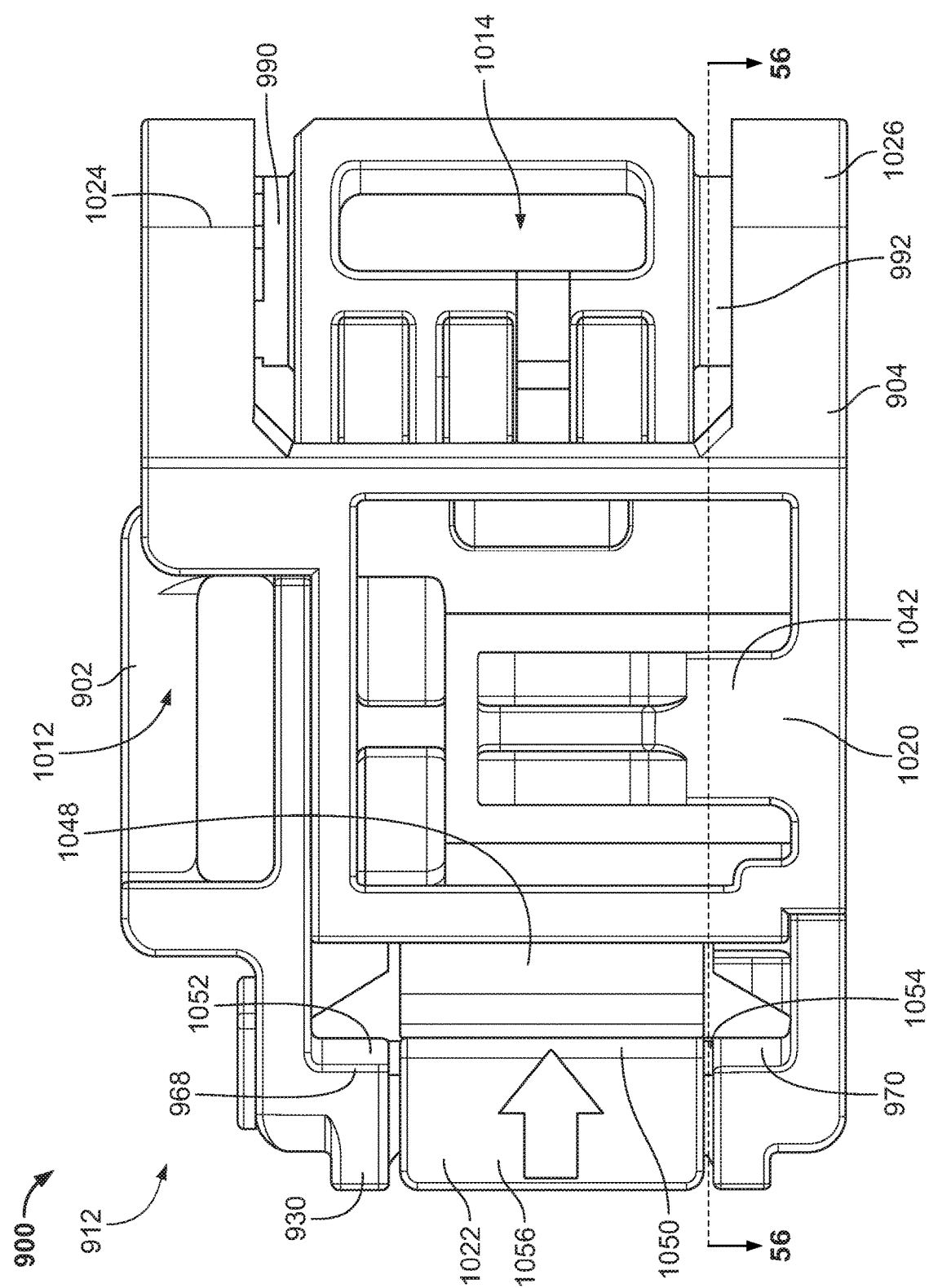
FIG. 43 is a front view of the seventh example fastener of FIGS. 41 and 42 in the closed state.

With reference to FIG. 56, in operation, when the clamp 904 is pivoted relative to the body 902 to place the seventh example fastener 900 in the closed state 912, the latch clip 1022 is inserted into the latch receiver 930. As the latch clip 1022 is pushed into the latch receiver 930, the lower catch 1054 slides against the lower shoulder 970. With reference to FIG. 43, as the latch clip 1022 is pushed into the latch receiver 930, the upper catch 1052 slides against the upper shoulder 968. Further, as the upper catch 1052 slides against the upper shoulder 968 and the lower catch 1054 slides against the lower shoulder 970, the second resilient wall 1050 resiliently flexes toward the first resilient wall 1048. Additionally, as the upper catch 1052 slides against the upper shoulder 968 and the lower catch 1054 slides against the lower shoulder 970, the first resilient wall 1048 resiliently flexes toward the second stud receiver 1020.

With reference to FIG. 43, in operation, as the latch clip 1022 is pushed yet further into the latch receiver 930, the upper catch 1052 slides past the upper shoulder 968 and the lower catch 1054 slides past the lower shoulder 970. When the upper catch 1052 slides past the upper shoulder 968 and the lower catch 1054 slides past the lower shoulder 970, the first resilient wall 1048 and the second resilient wall 1050 resiliently snap away from the second stud receiver 1020. When the first resilient wall 1048 and the second resilient wall 1050 resiliently snap away from the second stud receiver 1020, the upper catch 1052 snapably engages the upper shoulder 968. The lower catch 1054 snapably engages the lower shoulder 970 in the same manner as the upper catch 1052 and the upper shoulder 968. Thus, the latch clip 1022 is snapably retained in the latch receiver 930 when the seventh example fastener 900 is in the closed state 912.

Figure 59:
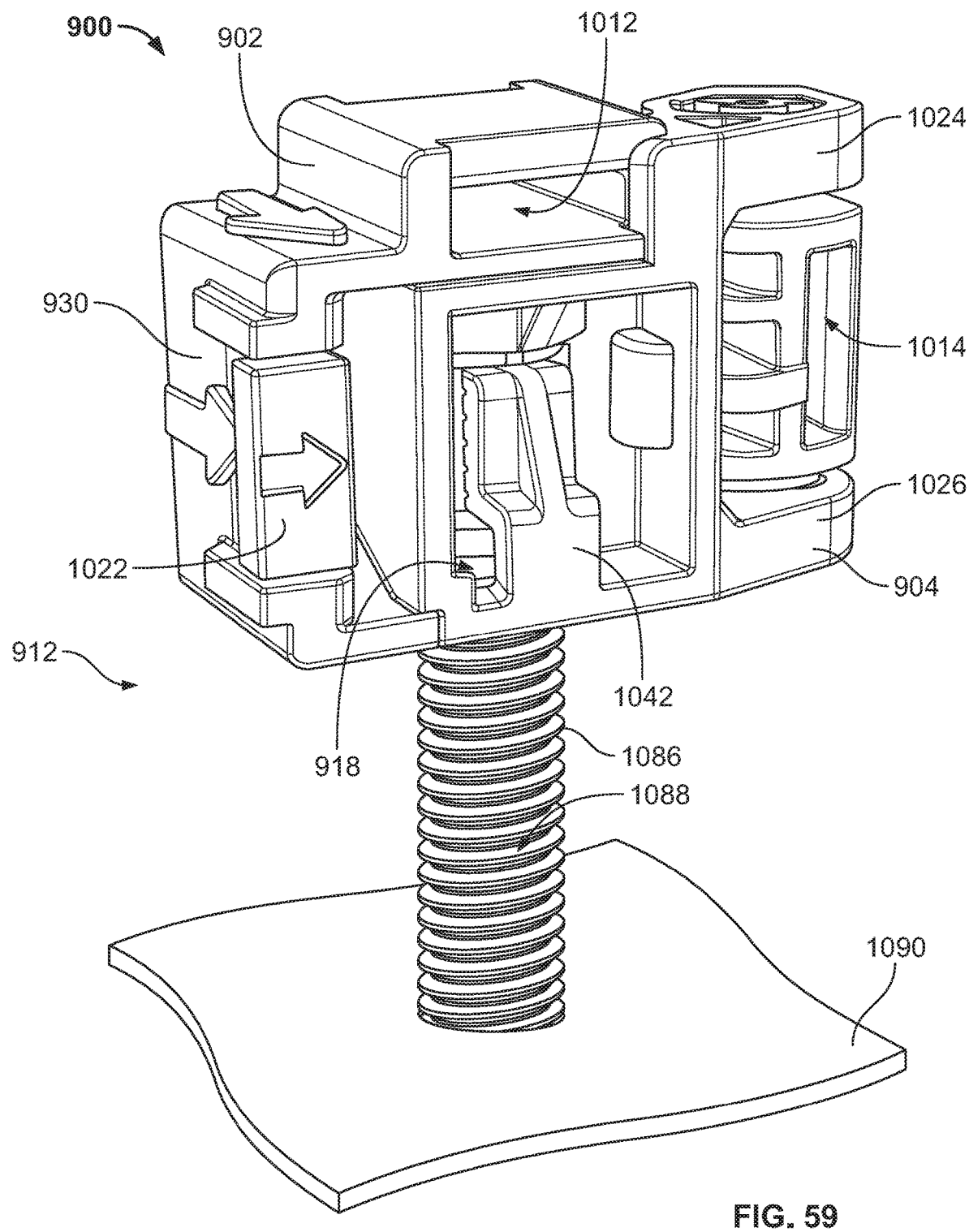
FIG. 59 is an isometric view of the seventh example fastener of FIGS. 41-49 and 54-58 in the closed stated and positioned over a stud.
Figure 60:
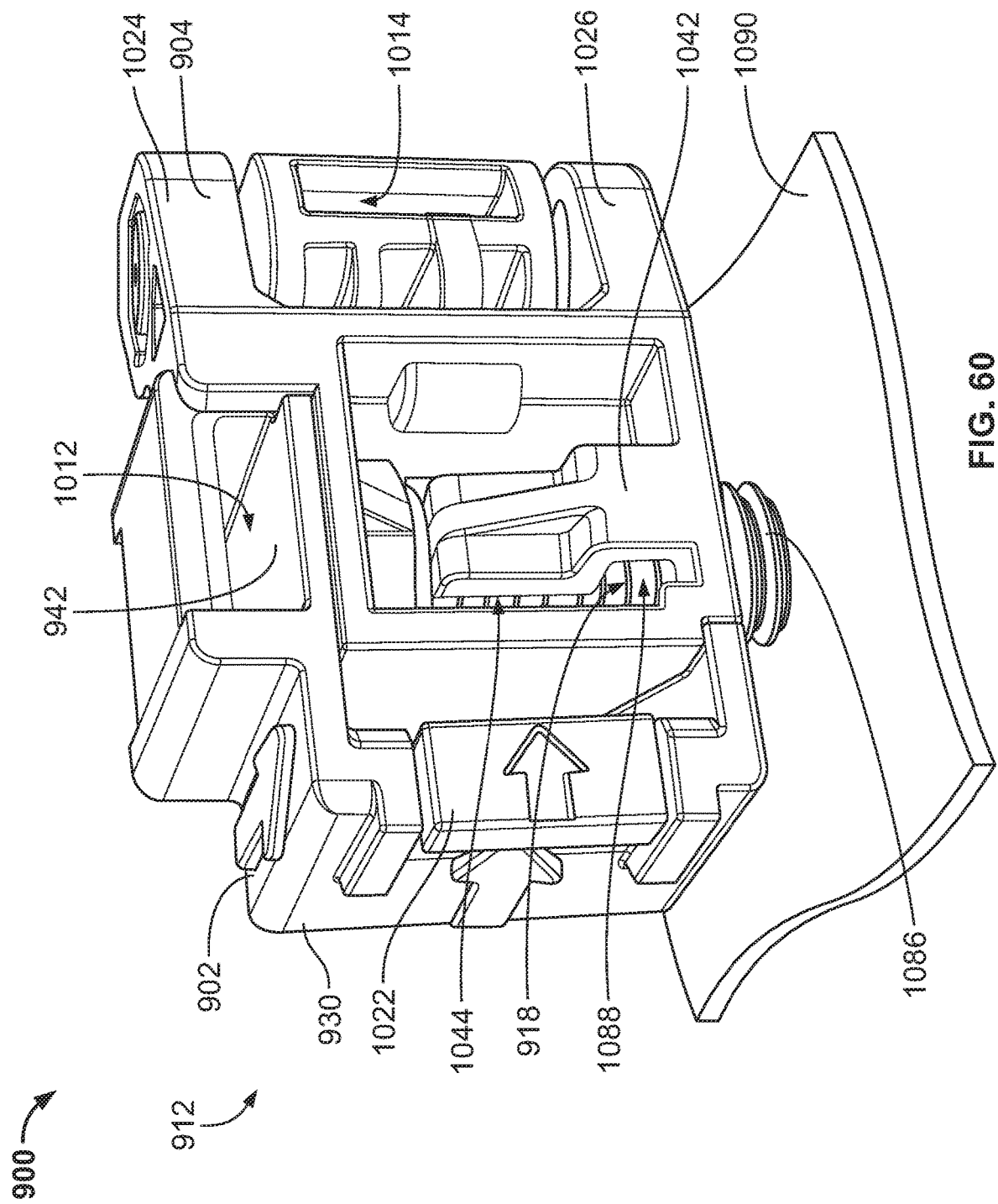
FIG. 60 is an isometric view of the seventh example fastener of FIGS. 41-49 and 54-59 in the closed state and assembled onto the stud of FIG. 59.

With reference to FIG. 59, the seventh example fastener 900 is configured to engage a stud 1086. The stud 1086 includes external threads 1088. In the example of FIG. 59, the stud 1086 is connected to a panel 1090. With reference to FIG. 60, in operation, the seventh example fastener 900 receives the stud 1086 via the stud cavity 918. When the stud 1086 is inserted into the stud cavity 918, the second set of the teeth 1044 ratchetingly engage the external threads 1088. Additionally, when the stud 1086 is inserted into the stud cavity 918 the first set of teeth 952 ratchetingly engage the external threads 1088 (not shown). More specifically, as the stud 1086 is pushed into the stud cavity 918, the second resilient arm 1042 flexes away from the stud 1086 and snappingly returns toward the stud 1086 as the external threads 1088 ratchetingly slide along the second set of teeth 1044. Similarly, as the stud 1086 is pushed into the stud cavity 918, the first resilient arm 950 flexes away from the stud 1086 and snappingly returns toward the stud 1086 as the external threads 1088 ratchetingly slide along the first set of teeth 952 (not shown). Further in operation, the stud 1086 contacts the first upper wall 942. The first upper wall 942 provides a hard stop to the stud 1086. Thus, the stud 1086 is not pushed through the seventh example fastener 900.

With reference to FIG. 60, further in operation, if a force is applied to remove the stud (not shown) from the seventh example fastener 900, the stud pulls against the second set of teeth 1044 and the first set of teeth 952 (not shown). When the stud pulls against the first set of teeth 952 and the second set of teeth 1044, the second resilient arm 1042 and the first resilient arm 950 (not shown) are pulled toward one another. Thus, pulling the stud 1086 and the seventh example fastener 900 from one another tightens the first set of teeth 952 and the second set of teeth 1044 against the external threads 1088. Thus, the sixth example fastener 900 is securely retained on the stud 1086.

Figure 61:
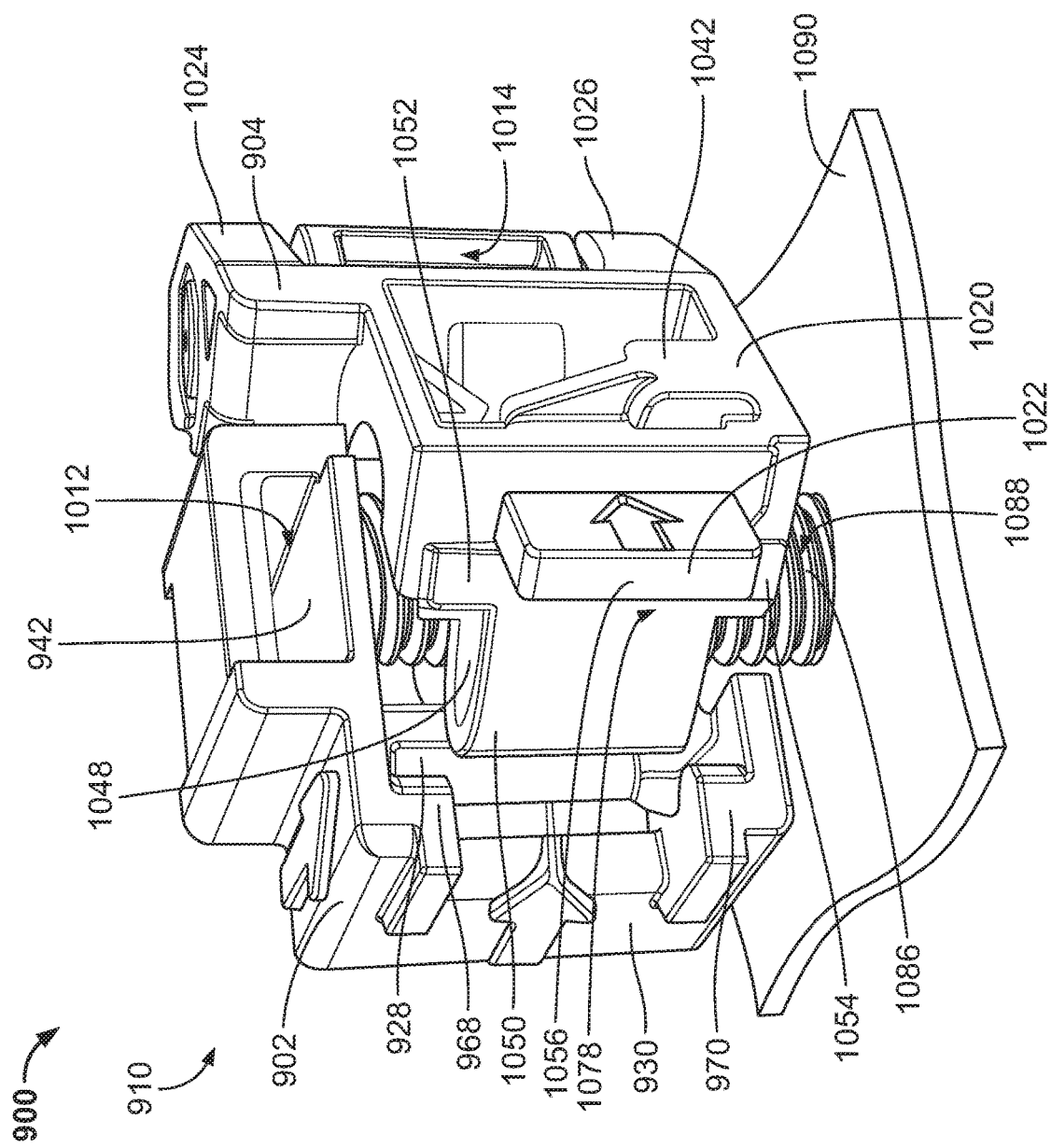
FIG. 61 is an isometric view of the seventh example fastener of FIGS. 41-49 and 54-60 in the released state about the stud of FIGS. 59 and 60.
Figure 62:
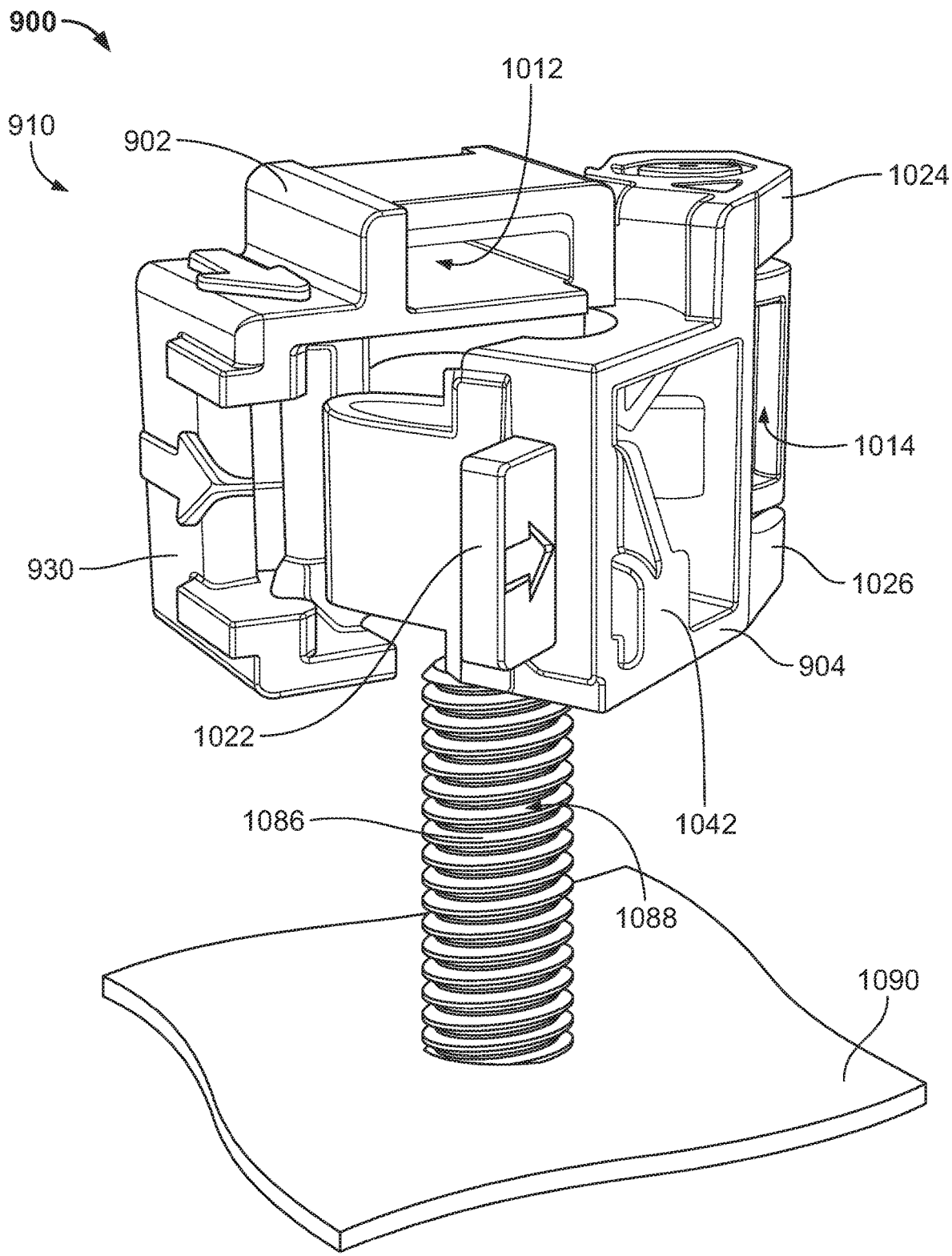
FIG. 62 is an isometric view of the seventh example fastener of FIGS. 41-49 and 54-61 in the released state and removed from the stud of FIGS. 59, 60, and 61.

With reference to FIGS. 61 and 62, further in operation, a tool (e.g., a screwdriver) (not shown) may be inserted into the tool pocket 1078 and pushed against the release wall 1056 and the second resilient wall 1050. When the tool is pushed against the release wall 1056 and the second resilient wall 1050, the first resilient wall 1048 and the second resilient wall 1050 flex inwardly toward the first stud receiver 928 and the second stud receiver 1020. As the first resilient wall 1048 and the second resilient wall 1050 flex inwardly toward the first stud receiver 928 and the second stud receiver 1020, the upper catch 1052 is released from the upper shoulder 968 and the lower catch 1054 is released from the lower shoulder 970. When the upper catch 1052 is released from the upper shoulder 968 and the lower catch 1054 is released from the lower shoulder 970, the clamp 904 is free to pivot away from the body 902. When the clamp 904 pivots away from the body 902, the seventh example fastener 900 is placed in the released state 910. Thus, the clamp 904 releasably mates with the body 902. Further, with reference to FIG. 62, the stud may thus be freed from the body 902 and the clamp 904 and released from the seventh example fastener 900. Additionally or alternatively, a finger of an operator may also be inserted into the tool pocket 1078 and pushed against the release wall 1056 and the second resilient wall 1050 in the same manner as the tool to release the clamp 904 from the body 902.

Figure 57:
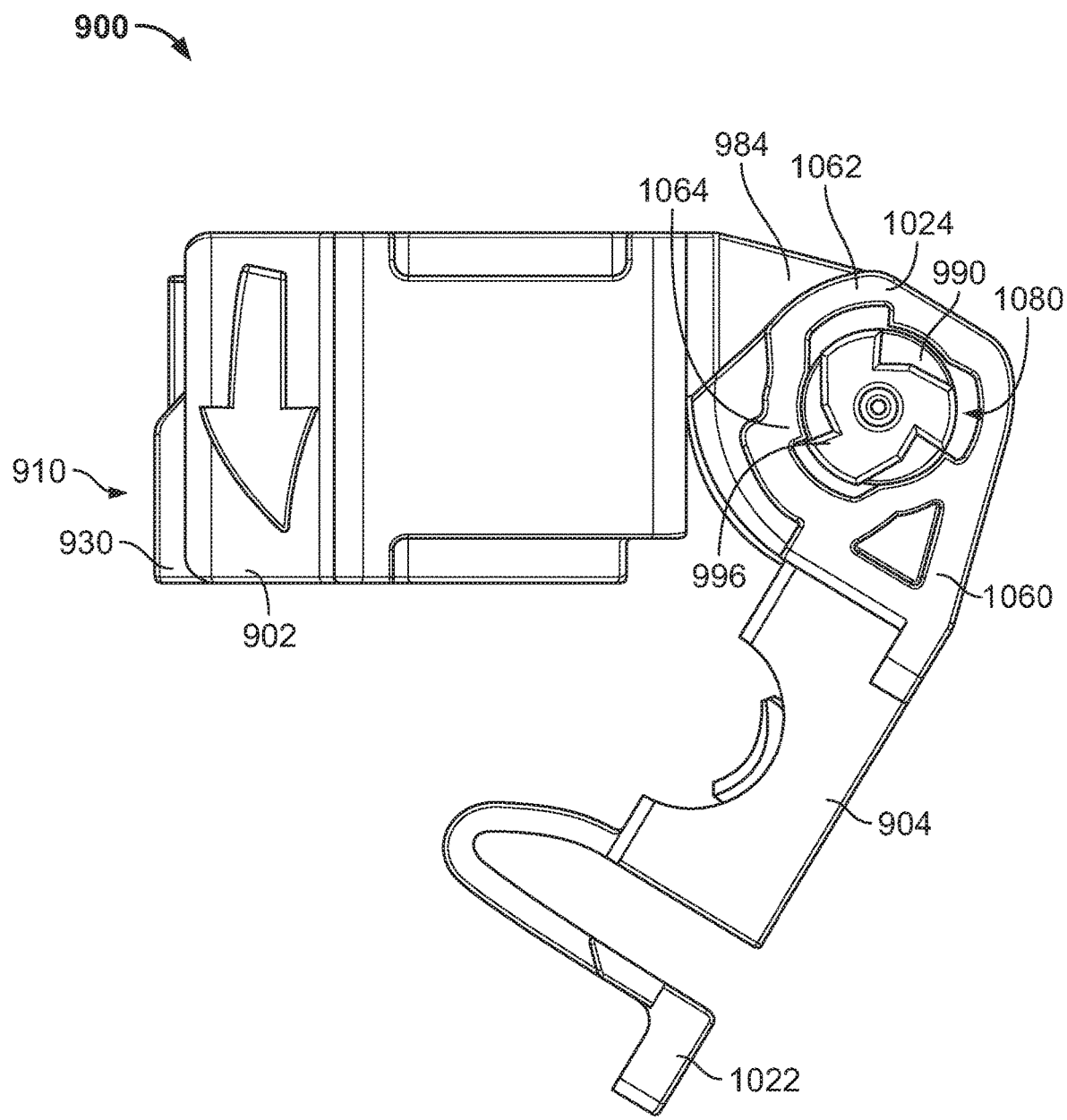
FIG. 57 is a top view of the seventh example fastener of FIGS. 41-49 and 54-56 in a released state.
Figure 58:
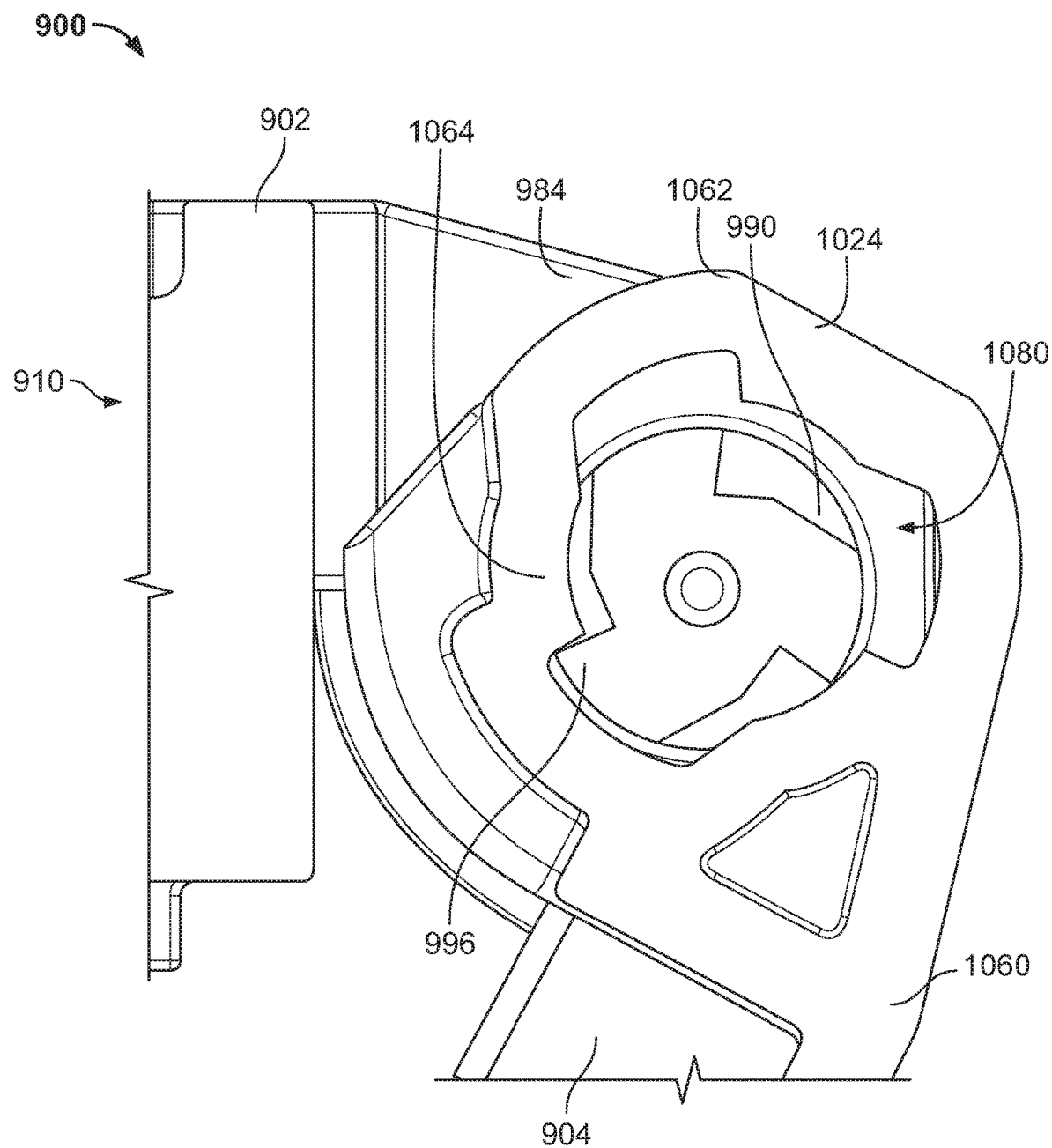
FIG. 58 is an enlarged partial top view of the seventh example fastener of FIGS. 41-49 and 54-57 in the released state.

With reference to FIGS. 57 and 58, when the seventh example fastener 900 is in the released state 910, the clamp 904 is ratchetingly engaged with the body 902. More specifically, the fourth upper wall 984 is slidably engaged with the upper hinge receiver 1024. Thus, the upper drum 990 is offset relative to (e.g., off-center, askew, oblique, etc.) the upper hinge receiver 1024 in the upper hinge opening 1080. Because the upper drum 990 is offset relative to the upper hinge receiver 1024, one or more of the upper barbs 996 ratchetingly engages with the upper set of pawls 1064. In other words, when the seventh example fastener 900 is in the released state 910, the upper hinge receiver 1024 tends to move out of concentricity with the upper drum 990, which restricts the opening angle of the clamp 904 relative to the body 902. Additionally, when the seventh example fastener 900 is in the released state 910, the third lower wall 986, the lower hinge receiver 1026, the lower drum 992, the lower barbs 1000, and the lower set of pawls 1072 engage with one another via the lower hinge opening 1082 (not shown) in the same manner as to the fourth upper wall 984, the upper hinge receiver 1024, the upper drum 990, the upper barbs 996, and the upper set of pawls 1064 engage with one another via the upper hinge opening 1080.

Embodiments of the present disclosure provide fasteners that are reusable and have features that facilitate operators in quickly assembling the fastener onto a stud and easily removing the fastener from the stud. The fasteners includes a body and a clamp that pivot relative to one another. The body and the clamp snapably releasably mate with one another. The body includes a first toothed resilient arm and defines a first stud pocket, a latch pocket, and a loop. The clamp includes a second toothed resilient arm and a latch and defines a second stud pocket. In a closed state, the fastener may be pushed onto a threaded stud to secure the toothed resilient arms onto the stud. Further, one or more tie straps may be inserted through the loop to secure a component to the fastener. Thus, the component may be engaged with the stud via the tie strap and the fastener. Additionally, the clamp may be released from the body to free the stud from the fastener. The clamp may further be relatched with the body and the fastener reengaged with the stud.

From the foregoing, it will be appreciated that the above example fasteners 100, 300, 400, 500, 600, 700, 900 include a body and a clamp that are pivotably engaged and releasably mate with one another. Additionally, it will be appreciated that the above example fasteners 100, 300, 400, 500, 600, 700, 900 also have at least one tie strap loop. Because the body releasably mates with the clamp and includes at least one tie strap loop, the fasteners 100, 300, 400, 500, 600, 700, 900 may be reused, remain attached to a component via a tie strap, and/or repositioned onto studs (e.g., of a vehicle), which may prevent assembly line stoppages, reduce scrap, and/or improve manufacturing efficiency. Thus, the above-disclosed example fasteners 100, 300, 400, 500, 600, 700, 900 conserve resources and may improve manufacturing efficiency as compared to existing fasteners.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

Variations and modifications of the foregoing are within the scope of the present disclosure. It is understood that the embodiments disclosed and defined herein extend to all alternative combinations of two or more of the individual features mentioned or evident from the text and/or drawings. All of these different combinations constitute various alternative aspects of the present disclosure. The claims are to be construed to include alternative embodiments to the extent permitted by the prior art.

To the extent used in the appended claims, the terms "including" and "in which" are used as the plain-English equivalents of the respective terms "comprising" and "wherein." Moreover, to the extent used in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Various features of the disclosure are set forth in the following claims.

What is claimed is:

1. A fastener, comprising:
    a body including a first hinge post molded with the body and a first resilient arm having a first set of teeth; and
    a clamp including a second hinge post that is pivotably engaged with the body at the first hinge post and the second hinge post, the clamp further including a second resilient arm having a second set of teeth,
    wherein the first set of teeth face the clamp, or the second set of teeth face the body, when the clamp is in a closed state relative to the body,
    wherein the first set of teeth and the second set of teeth are configured to engage a stud, and
    wherein the first set of teeth and the second set of teeth are configured to ratchetingly engage the stud when the clamp is in a closed state relative to the body.

2. The fastener of claim 1, wherein the clamp releasably mates with the body.

3. The fastener of claim 2, wherein:
    the body includes a latch receiver,
    the clamp includes a latch clip, and
    the latch clip snapably engages the latch receiver.

4. The fastener of claim 3, wherein the latch clip defines a tool pocket configured to receive a tool to flex the latch clip to release the latch clip from the latch receiver.

5. The fastener of claim 1, wherein the first set of teeth face the clamp when the clamp is in a closed state relative to the body.

6. The fastener of claim 1, wherein the first resilient arm is opposite the second resilient arm when the clamp is in a closed state relative to the body.

7. The fastener of claim 2, wherein the clamp includes a side wall and a latch clip, wherein the latch clip includes a first resilient wall in connection with the side wall.

8. The fastener of claim 7, wherein the latch clip further includes a second resilient wall that transitionally connects to the first resilient wall, wherein the second resilient wall is disposed laterally outward from the first resilient wall.

9. The fastener of claim 8, wherein:
    the first set of teeth face the second set of teeth when the clamp is in a closed state relative to the body.

10. The fastener of claim 1, wherein:
    the body further includes a loop, and
    the loop defines a tie strap passage.

11. The fastener of claim 1, wherein the second set of teeth face the body when the clamp is in a closed state relative to the body.

12. The fastener of claim 1, wherein the body and the clamp define a stud cavity when the clamp is in a closed state relative to the body.

13. The fastener of claim 1, wherein:
    the clamp includes a hinge socket, and
    the first hinge post is pivotably engaged with the hinge socket.

14. The fastener of claim 1, wherein:
    the body includes a hinge tongue,
    the body defines a hinge pocket, and
    the second hinge post is disposed in the hinge pocket and pivotably engages the hinge tongue.

15. The fastener of claim 13, wherein
    the first hinge post includes a snap lip,
    the hinge socket includes a pin hook, and
    the snap lip engages the pin hook to retain the first hinge post within the hinge socket.

16. A fastener retaining a stud, comprising:
    a clamp including a hinge post and a first resilient arm having a first set of teeth; and
    a body pivotably engaged with the clamp at the hinge post and having an upper wall and a loop that defines a tie strap passage, and
    a stud with a first threaded surface and a second surface that is orthogonal to the first threaded surface,
    wherein the first set of teeth face the body when the clamp is in a closed state relative to the body,
    wherein the first set of teeth is configured to engage the first threaded surface and the upper wall is configured to engage the second surface, and
    wherein when the stud is engaged with the first set of teeth the upper wall is between the loop and the stud.

17. The fastener of claim 16, wherein the clamp releasably mates with the body.

18. The fastener of claim 16, wherein the body includes a second resilient arm having a second set of teeth.

19. A fastener configured to be retained upon a stud, the fastener comprising:
    a body including a first stabilizer and a first resilient arm having a first retention feature; and
    a clamp configured to move toward the body along an axis to break the first stabilizer from the body before being pivotably engaged with the body around the axis and including a second resilient arm having a second retention feature,
    wherein the clamp is configured to be pivoted into a closed position with respect to the body such that the first and second features engage with the stud to provide for retention of the fastener on the stud, and wherein the clamp is further configured to be pivoted into an opened position with respect to the body such that the fastener may be removed from the stud.

* * * * *